US006265426B1

(12) United States Patent
Alanine et al.

(10) Patent No.: US 6,265,426 B1
(45) Date of Patent: Jul. 24, 2001

(54) TRIAZOLE DERIVATIVES

(75) Inventors: Alexander Alanine, Riedisheim (FR); Bernd Büttelmann, Schopfheim (DE); Marie-Paule Heitz Neidhart, Hagenthal le Bas (FR); Georg Jaeschke, Basel (CH); Emmanuel Pinard, Linsdorf (FR); René Wyler, Zürich (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/619,518

(22) Filed: Jul. 19, 2000

(30) Foreign Application Priority Data

Jul. 21, 1999 (EP) .................................................. 99114313

(51) Int. Cl.$^7$ .................... C07D 249/14; A61K 31/4196; A61P 25/00
(52) U.S. Cl. .................... 514/383; 548/266.2; 548/267.2
(58) Field of Search .............................. 548/267.2, 334.5, 548/335.2, 266.2; 514/383

(56) References Cited

FOREIGN PATENT DOCUMENTS

| 1579352 | 11/1980 | (EP) . |
| DE 19643037 | 4/1998 | (EP) . |
| WO 99/01128 | 1/1999 | (WO) . |
| WO 99/54314 | 10/1999 | (WO) . |

OTHER PUBLICATIONS

Abstract corresponding to DE 19643037.

Abstract corresponding to WO 99/54314.

*Primary Examiner*—Joseph K. McKane
*Assistant Examiner*—Andrea M D'Souza
(74) *Attorney, Agent, or Firm*—George W. Johnston; William H. Epstein

(57) ABSTRACT

The present invention relates to triazole and imidazole derivatives of formula I and to their pharmaceutically acceptable acid addition salts. These compounds are NMDA receptor subtype blockers and are useful for the treatment of diseases related to the NMDA receptor.

14 Claims, No Drawings

TRIAZOLE DERIVATIVES

This application claims priority to European Patent Office (EPO) 99114313.2 Jul. 21, 1999.

BACKGROUND OF THE INVENTION

Under pathological conditions of acute and chronic forms of neurodegeneration overactivation of NMDA receptors is a key event for triggering neuronal cell death. NMDA receptors are composed of members from two subunit families, namely NR-1 (8 different splice variants) and NR-2 (A to D) originating from different genes. Members from the two subunit families show a distinct distribution in different brain areas. Heteromeric combinations of NR-1 members with different NR-2 subunits result in NMDA receptors displaying different pharmacological properties. Therapeutic indications for NMDA receptor subtype specific blockers include acute forms of neurodegeneration caused, e.g., by stroke or brain trauma; chronic forms of neurodegeneration such as Alzheimer's disease, Parkinson's disease, Huntington's disease or ALS (amyotrophic lateral sclerosis); neurodegeneration associated with bacterial or viral infections and associated with diseases such as schizophrenia, anxiety and depression and acute/chronic pain.

SUMMARY OF THE INVENTION

The compounds of the present invention are NMDA (N-methyl-D-aspartate)-receptor-subtype selective blockers. NMDA receptors have a key function in modulating neuronal activity and plasticity which makes them key players in mediating processes underlying development of CNS including learning and memory formation and function. However when overactive, NMDA receptors contribute to neurodegeneration. Therefore compounds which block NMDA receptor activation are therapeutically important. The compounds of this invention are NMDA receptor blockers, thus have activity in reducing neurodegeneration related to NMDA activity. Conditions such as stroke or brain trauma, Alzheimer's disease, Parkinson's disease, Huntington's disease or ALS (amyotrophic lateral sclerosis), bacterial or viral infections, and schizophrenia, anxiety, depression and acute/chronic pain can all result in NMDA mediated neurodegeneration which neurodegeration can be prevented or treated by compounds of this invention.

The present invention relates to compounds of the formula

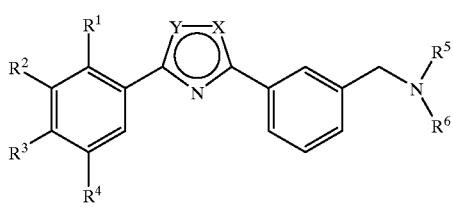

I wherein
$R^1$ $R^4$ signify independently hydrogen, —$CF_3$, —$OCF_3$, $OCHF_2$, —$OCH_2F$, lower alkyl, lower alkoxy, halogen, hydroxy, phenyl, benzyl, amino, nitro, pyrrol-1-yl, lower alkyl-sulfonyl, lower alkyl-sulfanyl, cyano or benzyloxy; or $R^2$ and $R^3$ may be taken together to form —O—$(CH_2)_2$—O—, —O—$CH_2$—O—, —O—$(CH_2)_2$—, —$(CH_2)_3$— or —CH═CH—CH═CH—;

X signifies —N═, —N($R^7$)— or —CH═;
Y signifies —N═, ═N—, —N($R^7$)— or —CH═; wherein at least one of X or Y has to be nitrogen;

$R^5$ and $R^6$ signify independently from each other hydrogen, lower alkyl, —C(O)-lower alkyl, hydroxy-lower alkyl, lower alkenyl, —C(O)$CH_2$OH or $R^5$ and $R^6$ may be taken together with the N-atom to form a substituted or unsubstituted ring structure —$(CH_2)_n$—, —$(CH_2)_2$—O—$(CH_2)_2$—, —$CH_2$—CH[OC(O)$CH_3$]—$(CH_2)_2$, —$CH_2$—CH[NHC(O)$CH_3$]—$(CH_2)_2$, —O—$(CH_2)_3$—, —$CH_2$—CH(O$CH_3$)—$(CH_2)_2$—, —$CH_2$—CH(halogen)—$(CH_2)_2$—, —$(CH_2)_2$—CH(O-phenyl)—$(CH_2)_2$—, —$(CH_2$—N(CHO)—$(CH_2)_2$—, —$CH_2$—N(CO$CH_3$)—$(CH_2)_2$—, —$CH_2$—CH(OH)—$(CH_2)_3$—, —$(CH_2)_2$—CH(OH)—$(CH_2)_2$—, —$(CH_2)_2$—N(benzyl)—$(CH_2)_2$— or —$CH_2$—CH═CH—$CH_2$—;

n signifies 3 to 5; and $R^7$ signifies hydrogen, lower alkyl, lower alkenyl, lower alkinyl, —$(CH_2)_m$—O-lower alkyl, —$(CH_2)_m$OH, —$(CH_2)_m$—$CHF_2$, —$(CH_2)_m$—$CH_2F$, —$(CH_2)_m$—C(O)-lower alkyl, —$(CH_2)_m$—C(O)O-lower alkyl, —$(CH_2)_m$—CH(OH)-lower alkyl, —$(CH_2)_m$—CH(OH)—$(CH_2)_m$OH, —$(CH_2)_m$—$C_6H_5$, which phenyl ring is optionally substituted by lower alkyl, lower alkoxy or hydroxy, —$(CH_2)_m$—C(═$CH_2$)-lower alkyl, —$(CH_2)_m$-cycloalkyl, —$(CH_2)_m$—CN, —$(CH_2)_m$-pyridin-4-yl, —$(CH_2)_m$-pyridin-3-yl or —$(CH_2)_m$-pyridin-2-yl;

m signifies 0 to 4;

and to the pharmaceutically acceptable acid addition salts and tautomers.

Object of the present invention are novel compounds of formular I and their tautomers and pharmaceutically acceptable acid addition salts thereof, the use of the compounds in the treatment or prophylaxis of diseases caused by overaction of respective NMDA receptor subtypes, which include acute forms of neurodegeneration caused, e.g., by stroke or brain trauma; chronic forms of neurodegeneration such as Alzheimer's disease, Parkinson's disease, Huntington's disease or ALS (amyotrophic lateral sclerosis); neurodegeneration associated with bacterial or viral infections, and associated with conditions such as schizophrenia, anxiety, depression and acute/chronic pain, the use of these compounds for manufacture of corresponding medicaments, processes for the manufacture of these novel compounds and medicaments, containing them.

DETAILED DESCRIPTION OF THE INVENTION

The following definitions of the general terms used in the present description apply irrespective of whether the terms in question appear alone or in combination:

As used herein, the term "lower alkyl" denotes a straight or branched-chain alkyl group containing from 1–4 carbon atoms, for example, methyl, ethyl, propyl, isopropyl, butyl and the like. The term "cycloalkyl" means a saturated hydrocarbon ring having from 3 to 10 carbon atoms, preferable from 5 to 7 carbon atoms.

The term "lower alkyl sulfonyl" means a lower alkyl group as defined above bound to the rest of the molecule through the sulfur atom in the sulfonyl group. The term "lower alkyl sulfanyl" means a lower alkyl group as defined above bound to the rest of the molecule through the sulfer atom in the sulfanyl group.

The term "hydroxy lower alkyl" means a lower alkyl group as defined above where one of the hydrogens is replaced by a hydroxyl group.

The term "lower alkoxy" denotes an ether group wherein the alkyl residue is as defined above.

The term "lower alkenyl" means an alkylene group having from 2 to 10 carbon atoms with a double bond located between any two adjacent carbon atoms. The term "lower alkinyl" means an alkylene group having from 2 to 10 carbon atoms with a triple bond located between any two adjacent carbon atoms.

The term "halogen" denotes chlorine, bromine, fluorine or iodine.

The term "pharmaceutically acceptable acid addition salts" embraces salts with inorganic and organic acids, such as hydrochloric acid, nitric acid, sulfuric acid, lactic acid, phosphoric acid, citric acid, formic acid, fumaric acid, maleic acid, acetic acid, succinic acid, trataric acid, methane-sulfonic acid, p-toluenesulfonic acid and the like.

The term "tautomers" embraces the standard meaning of the term, e.g. a type of isomerism in which migration of a hydrogen atom results in two or more structures called tautomers. For example any compound of this invention where X is —N= or —CH= and Y is —N($R^7$)— includes the tautomer where Y is —N= or —CH= and X is —N($R^7$)—, where $R^7$ is a suitable group.

Thus the triazole or imidazole group of compounds of formula I represented by

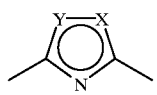

may have the following structure:

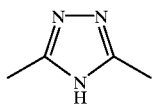
(a)

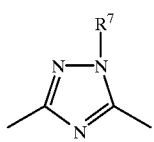
(b)

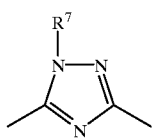
(c)

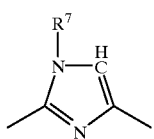
(d)

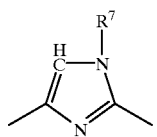
(e)

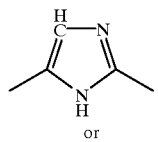
(f)

or

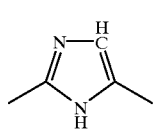
(g)

In preferred compounds of formula I, $R^1$ is hydrogen, lower alkoxy, halogen, or hydroxy; $R^2$ is hydrogen, lower alkoxy, halogen, $CF_3$, —$OCF_3$, $OCHF_2$, or may be taken together with $R^3$ to form —O—$(CH_2)_2$—O—, —O—$CH_2$—O—, —O—$(CH_2)_2$—, —$(CH_2)_3$— or —CH=CH—CH=CH—; —$OCH_3$, $R^4$ is hydrogen, halogen, lower alkoxy, or $CF_3$, and $R^3$, $R^5$, $R^6$ and $R^7$ are all as in formula I. In especially preferred such compounds, $R^1$ is hydrogen, methoxy, ethoxy, chloro, or fluoro; $R^2$ is hydrogen, chioro, or fluoro, $R^3$ is —$OCHF_2$, —$OCH_2F$, —$OCH_3$, —$OCH_2CH_3$, chloro, methyl or methyloxy; $R^4$ is hydrogen or fluoro, and $R^5$ and $R^6$ are hydrogen or lower alkyl or are together —$(CH_2)_4$—, —$CH_2CH(OH)(CH_2)_2$— or —$CH_2CH[NHC(O)CH_3](CH_2)_2$—. Relevant tautoers, are included.

Exemplary especially preferred compounds of formula I, in which X is —N=, Y is —NH—, $R^1$ is hydrogen, $R^2$ is hydrogen or fluoro, $R^3$ is —$OCHF_2$, —$OCH_2F$ or —$OCH_3$, $R^4$ is hydrogen or fluoro and $R^5$ and $R^6$ are methyl, are:

{3-[5-(4-difluoromethoxy-phenyl)-1H-[1,2,4]triazol-3-yl]-benzyl}-dimethyl-amine (mixture of tautomers), {3-[5-(4-fluoromethoxy-phenyl)-1H-[1,2,4]triazol-3-yl]-benzyl}-dimethyl-amine (mixture of tautomers), {3-[5-(3-fluoro-4-methoxy-phenyl)-1H-[1,2,4]triazol-3-yl]-benzyl}-dimethyl-amine (mixture of tautomers), {3-[5-(4-difluoromethoxy-3-fluoro-phenyl)-1H-[1,2,4]triazol-3-yl]-benzyl}-dimethyl-amine (mixture of tautomers), {3-[5-(3,5-difluoro-4-methoxy-phenyl)-1H-[1,2,4]triazol-3-yl]-benzyl}-dimethy-amine (mixture of tautomers) and {3-[5-(3-fluoro-4-fluoromethoxy-phenyl)-1H-[1,2,4]triazol-3-yl]-benzyl}-dimethyl-amine (mixture of tautomers).

Further especially preferred compounds of formula I are those in which X is —N=, Y is —NH—, $R^1$ is hydrogen, $R^2$ is hydrogen or chloro, $R^3$ is —$OCHF_2$, —$OCH_3$ or —$OCH_2CH_3$, $R^4$ is hydrogen or fluoro and $R^5$ and $R^6$ are hydrogen or methyl or are together —$(CH_2)_4$—, —$CH_2CH(OH)(CH_2)_2$— or —$CH_2CH[NHC(O)CH_3](CH_2)_2$—.

Examples of these Compounds are the Following:

5-(4-difluoromethoxy-phenyl)-3-(3-pyrrolidin-1-ylmethyl-phenyl)-1H-[1,2,4]triazole (mixture of tautomers), 5-(3-fluoro-4-methoxy-phenyl)-3-(3-pyrrolidin-1-ylmethyl-phenyl)-1H-[1,2,4]triazole (mixture of tautomers), 5-(4-ethoxy-phenyl)-3-(3-pyrrolidin-1-ylmethyl-phenyl)-1H-[1,2,4]triazole (mixture of tautomers), 5-(3-chloro-4-methoxy-phenyl)-3-(3-pyrrolidin-1-ylmethyl-phenyl)-1H-[1,2,4]triazole (mixture of tautomers), 3-[5-(4-methoxy-phenyl)-1H-[1,2,4]triazol-3-yl]-benzylamine (mixture of tautomers), (RS)-1-{3-[5-(4-methoxy-phenyl)-1H-[1,2,4]triazol-3-yl]-benzyl}-pyrrolidin-3-ol (mixture of tautomers), (S)-N-(1-{3-[5-(4-methoxy-phenyl)-1H-[1,2,4]triazol-3-yl]-benzyl}-pyrrolidin-3-yl)-acetamide (mixture of tautomers) and {3-[5-(4-methoxy-phenyl)-1H-[1,2,4]triazol-3-yl]-benzyl}-methyl-amine (mixture of tautomers).

Especially preferred imidazol derivatives are those of formula I wherein X is —CH= or —NH—, Y is =N— or —CH=, only one of X or Y is nitrogen, $R^1$ is hydrogen, $R^2$ is hydrogen or chloro, $R^3$ is chloro, methyl or methyloxy, $R^4$ is hydrogen and $R^5$ and $R^6$ are hydrogen, methyl or ethyl, for example the following:

3-[2-(3,4-dichloro-phenyl)-3H-imidazol-4-yl]-benzylamine (mixture of tautomers), {3-[2-(3,4-dichloro-phenyl)-3H-imidazol-4-yl]-benzyl}methyl-amine (mixture of tautomers), {3-[2-(3,4-dichloro-phenyl)-3H-imidazol-4-yl]-benzyl}-ethyl-amine (mixture of tautomers), 3-[4-(4-methoxy-phenyl)-1H-imidazol-2-yl]-benzylamine (mixture of tautomers) and 3-(4-p-tolyl-1H-imidazol-2-yl)-benzylamine hydrochloride (mixture of tautomers).

Other especially preferred triazole derivatives are those of formula I wherein X is —($R^7$)— or —N= and Y is —N($R^7$)— or —N= and $R^7$ is lower alkyl, —$CH_2$—O-lower alkyl or —$(CH_2)_2OH$, $R^1$, $R^2$ and $R^4$ are hydrogen, $R^3$ is methyloxy, and $R^5$ and $R^6$ are methyl, for example the following:

{3-[5-(4-methoxy-phenyl)-2-methyl-2H-[1,2,4]triazol-3-yl]-benzyl}-dimethyl-amine, 3-(4-methoxy-phenyl)-1-methyl-5-(3-pyrrolidin-1-ylmethyl-phenyl)-1H-[1,2,4]triazole, 5-[3-(2,5-dihydro-pyrrol-1-ylmethyl)-phenyl]-3-(4-methoxy-phenyl)-1-methyl-1H-[1,2,4]triazole, 1-ethyl-3-(4-methoxy-phenyl)-5-(3-pyrrolidin-1-ylmethyl-phenyl)-1H-[1,2,4]triazole, {3-[2-ethoxymethyl-5-(4-methoxy-phenyl)-2H-[1,2,4]triazol-3-yl]-benzyl}-dimethyl-amine, {3-[2-methoxymethyl-5-(4-methoxy-phenyl)-2H-[1,2,4]triazol-3-yl]-benzyl}-dimethyl-amine, 2-[5-(3-dimethylaminomethyl-phenyl)-3-(4-methoxy-phenyl)-[1,2,4]triazol-1-yl]-ethanol, {3-[5-(4-difluoromethoxy-phenyl)-2-methyl-2H-[1,2,4]triazol-3-yl]-benzyl}-dimethyl-amine, dimethyl-[3-(2-methyl-5-p-tolyl-2H-[1,2,4]triazol-3-yl)-benzyl]-amine and {3-[5-(3-Fluoro-4-methoxy-phenyl)-2-methyl-2H-[1,2,4]triazol-3-yl]-benzyl}-dimethyl-amine.

The novel compounds of formula I and their pharmaceutically acceptable salts can be prepared by techniques known in the art, with the guidance of processes described below, which comprise a) reacting a compound of formula

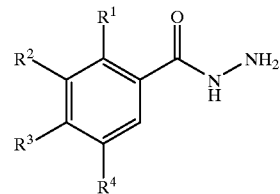

II with a compound of the formula

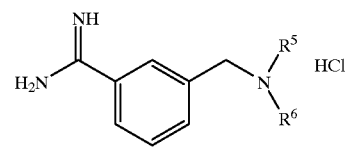

III to a compound of formula

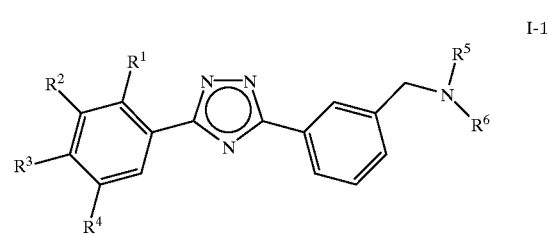

I-1 wherein $R^1$–$R^6$ have the significances given above, or b) reacting a compound of formula II with a compound of formula

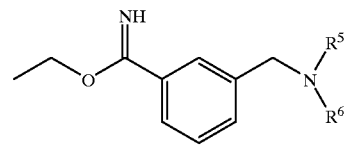

IV to a compound of formula I-1, or c) reacting a compound of formula

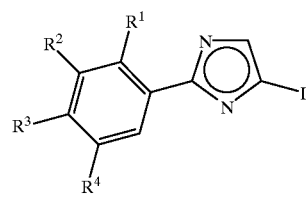

V with a compound of formula

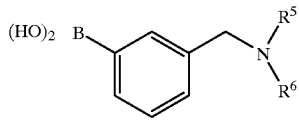
VI in the presence of Pd(PPh$_3$)$_4$ to a compound of formula

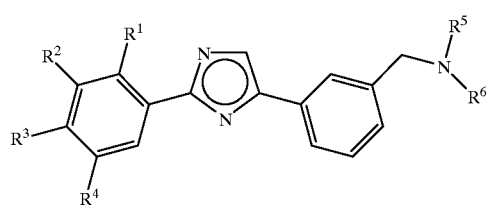
I-2 wherein R$^1$–R$^6$ have the significances given above, or
d) reducing a compound of formula

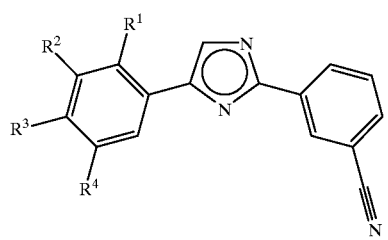
VII to a compound of formula

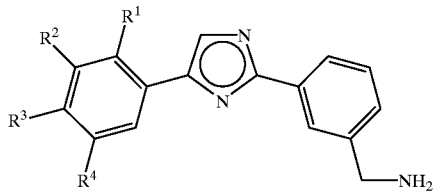
I-3 wherein R$^1$–R$^6$ have the significances given above, or
e) reacting a compound of formula I-3 with R$^{5'}$COCl and LiAlH$_4$ to give a compound of formula

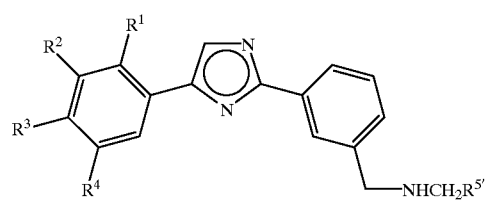
I-4 wherein R$^1$–R$^6$ have the significances given above and R$^{5'}$ is hydrogen, lower alkyl or
f) reacting a compound of formular I-4 with R$^{6'}$ COCl and LiAlH$_4$ to give a compound of formula to give a compound of formula

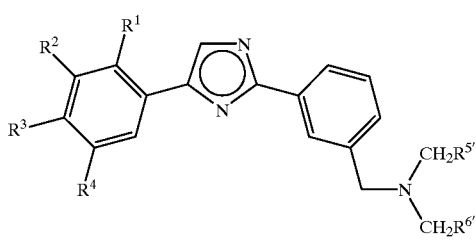
I-5 wherein R$^1$–R$^6$ have the significances given above, R$^{5'}$ and R$^{6'}$ are hydrogen, lower alkyl or hydroxy-lower alkyl, or g) isolating single regioisomers from a mixture of isomers, or h) modifying one or more substituents R$^1$–R$^6$ within the definitions given above, and,
if desired, converting the compound obtained into a pharmaceutically acceptable acid addition salt.

This invention is also directed to specific processes which follow.

A process for preparing a compound of formula I where Y is —N= or =N— and X is —N=, which process comprises:

reacting a compound of formula

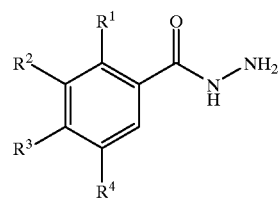
II with a compound of the formula

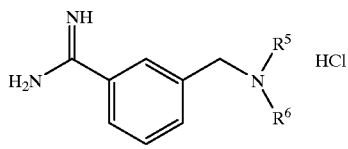
III or

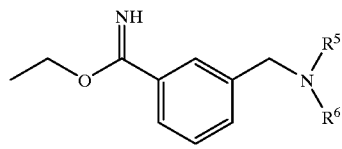
IV to obtain a compound of formula

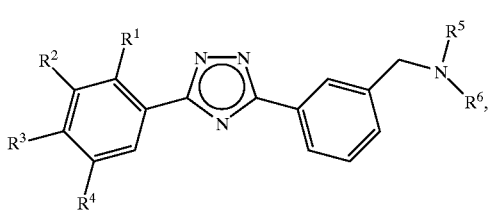

I-1 and isolating single regioisomers from a mixture of isomers, and modifying one or more substituents $R^1$–$R^6$, wherein $R^1$–$R^6$ have the significances given in formula I.

A process for preparing a compound of formula I where Y is —N= or =N— and X is —CH=, which process comprises:

reacting a compound of formula

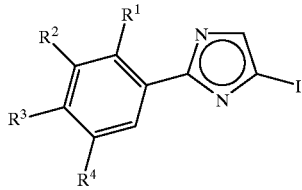

V with a compound of formula

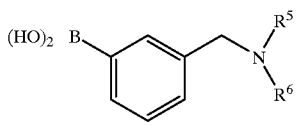

VI in the presence of Pd(PPh$_3$)$_4$ to obtain a compound of formula

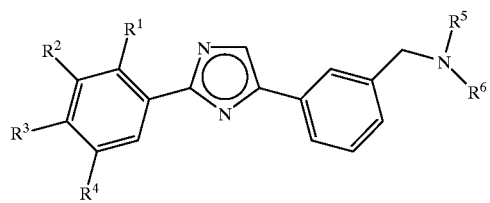

I-2 and isolating single regioisomers from a mixture of isomers, and modifying one or more substituents $R^1$–$R^6$, wherein $R^1$–$R^6$ have the significances given in formula I.

A process for preparing a compound of formula I where Y is —CH= and X is —N=, and $R^5$ and $R^6$ are hydrogen, lower alkyl, or hydroxy lower alkyl which process comprises:

a) reducing a compound of formula

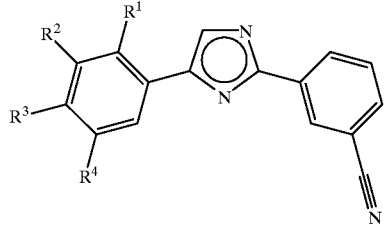

VII to a compound of formula

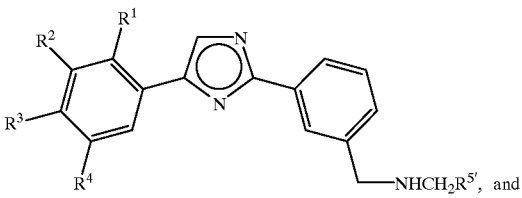

I-3 b) reacting a compound of formula I-3 with $R^{5'}$COCl and LiAlH$_4$ to give a compound of formula

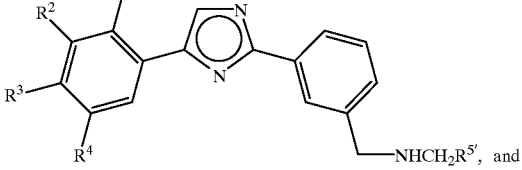

I-4 c) reacting a compound of formula I-4 with $R^{6'}$COCl and LiAlH$_4$ to give a compound of formula

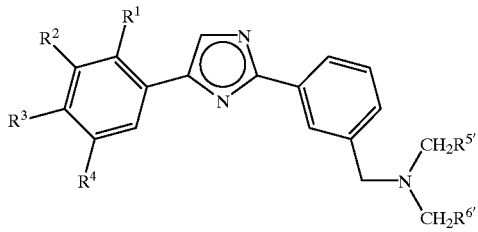

I-5 and isolating single regioisomers from a mixture of isomers, where $R^{5'}$ and $R^{6'}$ are hydrogen, lower alkyl, or hydroxy lower alkyl.

The preparation of compounds of formula I, wherein the nitrogen atom of the triazole or imidazole ring is substituted by $R^7$, is described in more detail in the examples.

In accordance with process variant a) a compound of formula II is reacted with a compound of formula III to afford a compound of formula I-1. This reaction is carried out in the presence of sodium ethoxide in ethanol under reflux.

Furthermore, compounds of formula I-1 may be obtained by reaction of a compound of formula II with a compound of formula IV in the presence of sodium ethoxide in ethanol under reflux in accordance with reaction variant b).

A compound of formula I-2 is obtained in accordance with process variant c) by reaction of a compound of formula V with a compound of formula VI in the presence of Pd(PPh₃)₄ and a base, such as sodium carbonate, in a solvent, for example in toluene.

The reduction of a compound of formula VII to a compound of formula I-3 is carried out with lithium aluminium hydride in a solvent, such as tetrahydrofuran, in conventional manner.

In accordance with reaction variant e) a compound of formula I-3 is reacted with $^{5'}$COCl in a solvent, such as methylene chloride or THF to give a compound of formula I-4, which may be react further with $R^{6'}$COCl to a compound of formula I-1, in accordance with process variant f).

A single regioisomer may be isolated from a mixture of isomers in conventional manner, for example by chromatography by separation on SiO₂.

The salt formation in accordance with the invention is effected according to methods which are generally usual and which are familiar to any person skilled in the art.

The starting materials for the preparation of compounds of formula I are known compounds or can be prepared by known methods, for example in schemes 1–7.

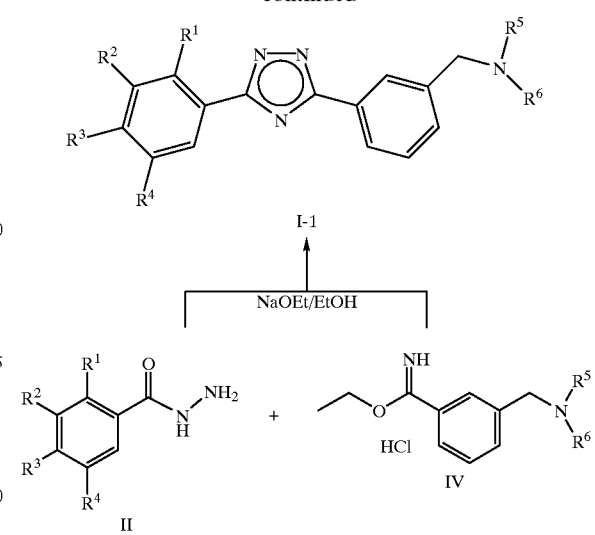

Scheme 1

$R^5$ and $R^6$ have the significance given above.

Scheme 2

$R^1$–$R^4$ have the significance given above.

Scheme 3

$R^1$–$R^6$ have the significances given above.

Scheme 4
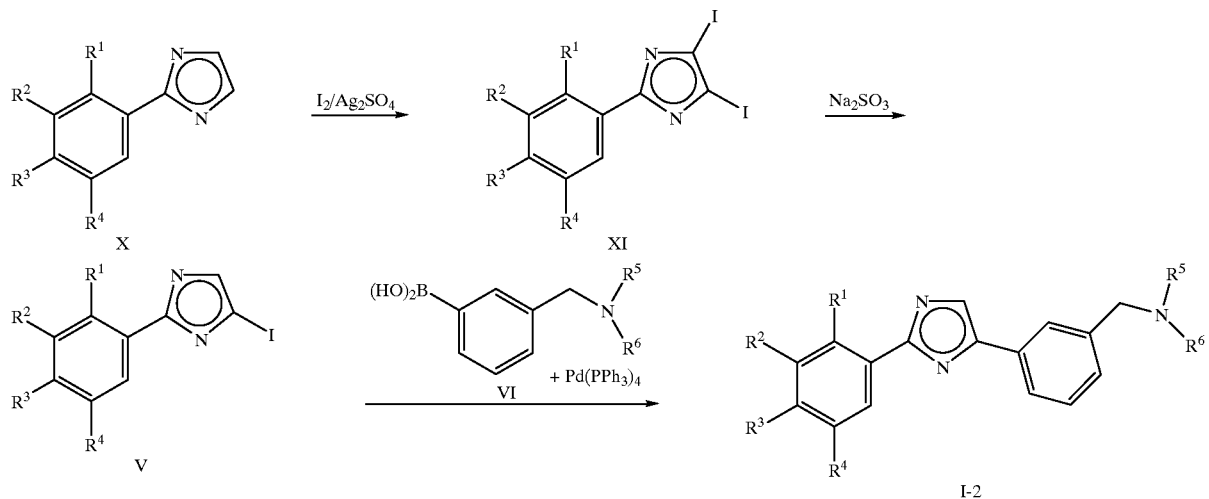
$R^1$–$R^6$ have the significances given above.
Scheme 5
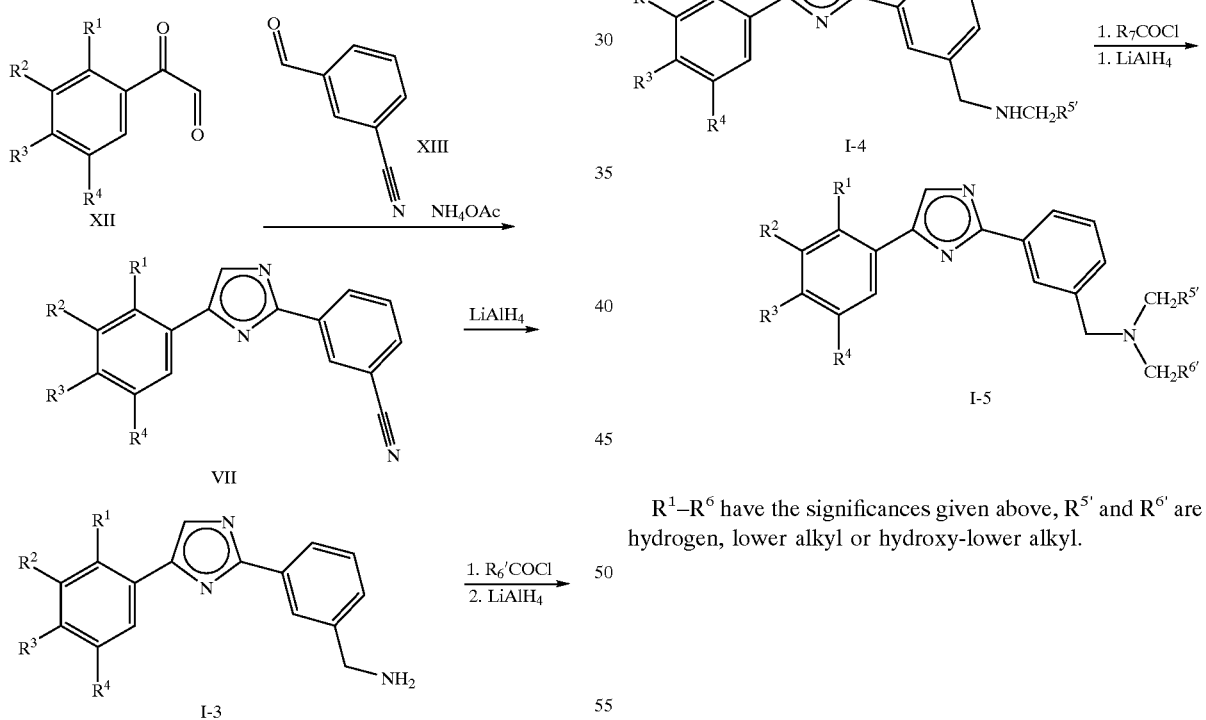
$R^1$–$R^6$ have the significances given above, $R^{5'}$ and $R^{6'}$ are hydrogen, lower alkyl or hydroxy-lower alkyl.

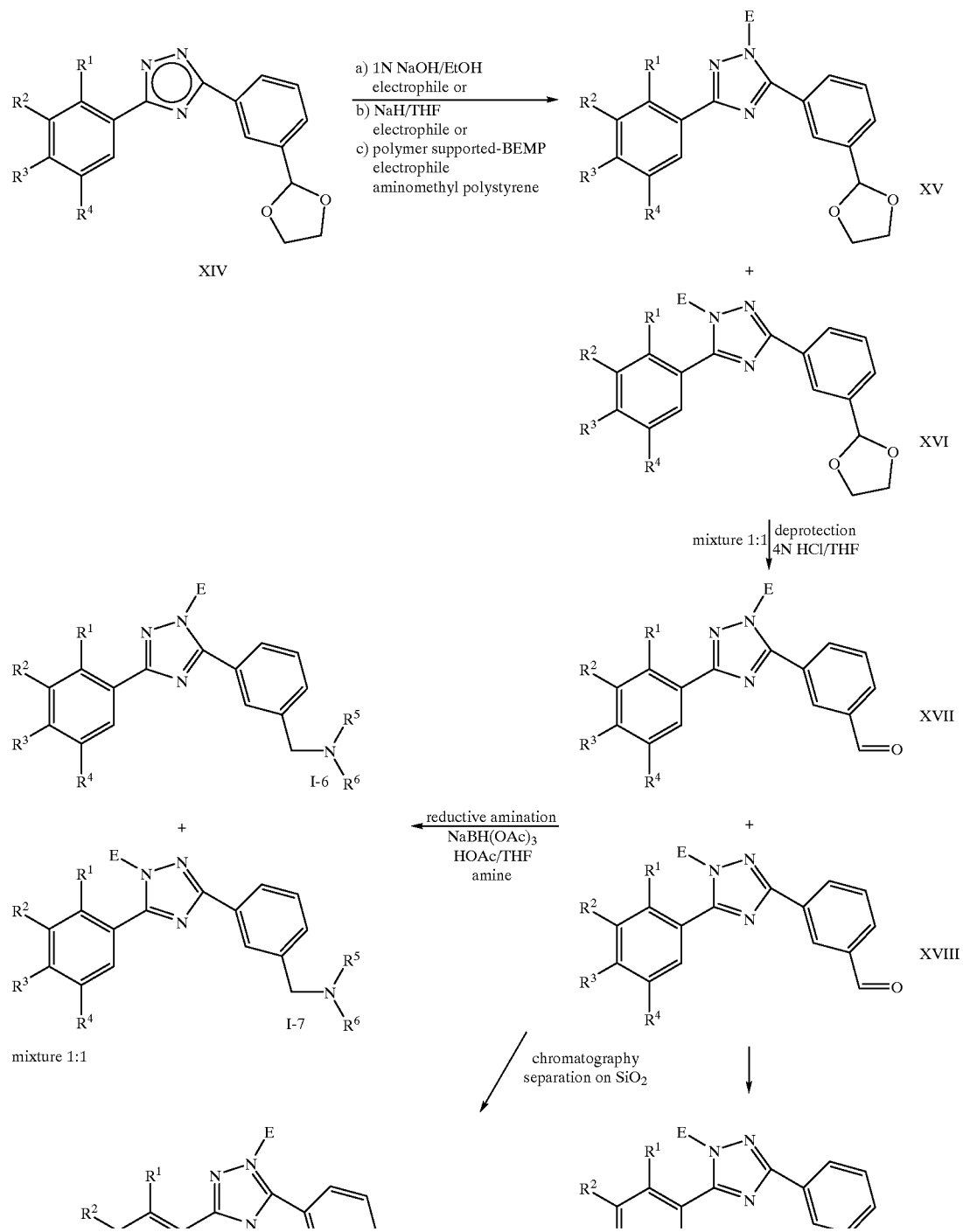

Scheme 7

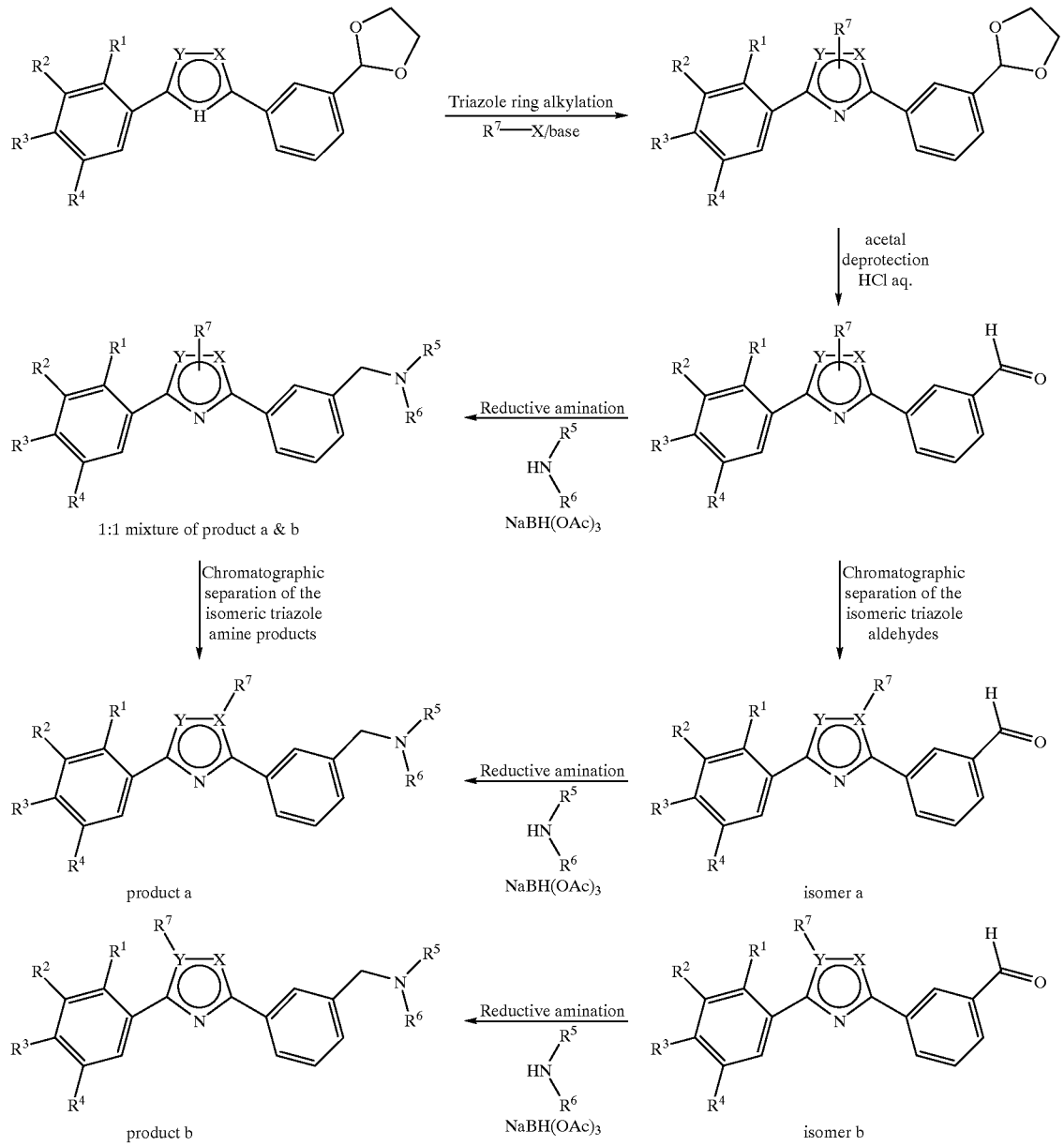

wherein $R^1$ to $R^7$ have the significances given above and X and Y are an nitrogen or carbon atom, wherein one of X or Y has to be nitrogen.

As mentioned earlier, the compounds of formula I and their pharmaceutically usable acid addition salts possess valuable pharmacodynamic properties as NMDA-receptor subtype selective blockers. NMDA receptors have a key function in modulating neuronal activity and plasticity and are key players in mediating processes underlying development of CNS as well as learning and memory formation. However when overactive, NMDA receptors contribute to neurodegeneration. The compounds of this invention are NMDA receptor blockers, thus have activity in reducing neurodegeneration related to NMDA acivity.

The compounds were investigated in accordance with the test given hereinafter.

Method 1

$^3$H R-(R*,S*)]-α-(4-Hydroxy-phenyl)-β-methyl-4-(phenyl-methyl)-1-piperidine propanol (compound A) binding Male Füllinsdorf albino rats weighing between 150–200 g were used. Membranes were prepared by homogenization of the whole brain minus cerebellum and medulla oblongata with a Polytron (10.000 rpm, 30 seconds), in 25 volumes of a cold Tris-HCl 50 mM, EDTA 10 mM, pH 7.1 buffer. The homogenate was centrifuged at 48.000 g for 10 minutes at 4° C. The pellet was resuspended using the Polytron in the same volume of buffer and the homogenate was incubated at 37° C. for 10 minutes. After centrifugation the pellet was homogenized in the same buffer and frozen at −80° C. for at least 16 hours but not more than 10 days. For the binding assay the homogenate was thawed at 37° C., centrifuged and the pellet was washed three times as above in a Tris-HCl 5 mM, pH 7.4 cold buffer. The final pellet was resuspended in the same buffer and used at a final concentration of 200 μg of protein/ml.

Compound A binding experiments were performed using a Tris-HCl 50 mM, pH 7.4 buffer. For displacement experiments 5 nM of Compound A were used and non specific binding was measured using 10 μM of tetrahydroisoquinoline and usually it accounts for 10% of the total. The incubation time was 2 hours at 4° C. and the assay was stopped by filtration on Whatmann GF/B glass fiber filters (Unifilter-96, Packard, Zütrich, Switzerland). The filters were washed 5 times with cold buffer. The radioactivity on the filter was counted on a Packard Top-count microplate scintillation counter after addition of 40 mL of microscint 40 (Canberra Packard S.A., Zürich, Switzerland).

The effects of compounds were measured using a minimum of 8 concentrations and repeated at least once. The pooled normalized values were analyzed using a non-linear regression calculation program which provide $IC_{50}$ with their relative upper and lower 95% confidence limits (RS1, BBN, USA). The $IC_{50}$ value refers to the concentration of a compound needed to give 50% inhibition, i.e., the concentration at which 50% of the ligands bonded to the recept or are displaced. The $IC_{50}$ of compounds of the present invention is in the range of 0.008–1.000 μM.

In table below are shown some specific activity data:

| Example-No. | $IC_{50}$ (μM) |
|---|---|
| 25 | 1.000 |
| 49 | 0.087 |
| 51 | 0.058 |
| 52 | 0.330 |
| 73 | 0.0083 |

Concentrations higher than 10 μM were not tested. If 10 μM of the compound turned out to produce less than 50% effect, $IC_{50}$ was labelled as ">10 μM" and the compound was characterised by the average effect seen at 10 μM.

The compounds of formular I and their salts, as herein described, together with pharmaceutically inert excipients can be incorporated into standerd phermaceutical dosage forms, for example, for oral or perental application with usual pharmaceutical adjuvant materialss, for example, organic or inorganic inert carrier materials, such as, water, gelatin, lactose, starch, magnesium stearate, talc, vegetable oils, gums, polyalkylene-glycols and the like. Examples of pharmaceutical preparations in solid form are tablets, suppositories, capsules, or in liquid form are solutions, suspensions or emulsions. Pharmaceutical adjuvant materials include preservatives, stabilizers, wetting or emulsifying agents, salts to change the osmotic pressure or to act as buffers. The pharmaceutical preparations can also contain other therapeutically active substances. Therefore, this invention is also directed to a pharmaceutical composition comprising any compound of formula 1 and a pharmaceutically acceptable carrier, and optionally other components as provided above. Preferred compositions include the specific compounds of formula I described above.

The daily dose of compounds of formula I to be administered varies with the particular compound employed, the chosen route of administration and the recipient. Representative of a method for administering the compounds of formula I is by the oral and parenteral type administration route. An oral formulation of a compound of formula I is preferably administered to an adult at a dose in the range of 1 mg to 1000 mg per day. A parenteral formulation of a compound of formula I is preferably administered to an adult at a dose in the range of from 5 to 500 mg per day. Therefore, this invention is also directed to a method for treating neurodegeneration by administering a pharmaceutical composition comprising any compound of formula I and a pharmaceutically acceptable carrier, and optionally other components as provided above. The amount of the compound administered is an amount effective to relieve or prevent neurodegeneration, as described above. Preferred methods use specific compounds of formula I described above.

The following Examples illustrate the present invention without limiting it. All temperatures are given in degree Celsius.

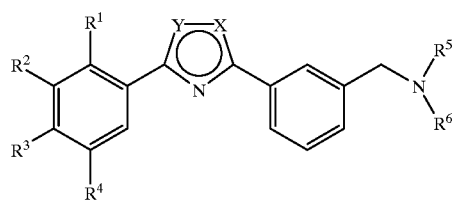

| R¹ | R² | R³ | R⁴ | X | Y | R⁵/R⁶ | Ex. |
|---|---|---|---|---|---|---|---|
| H | H | OCHF₂ | H | —N= | —NH— | ≈N< | 1 |
| H | H | OCH₂F | H | —N= | —NH— | ≈N< | 2 |
| H | F | OCH₃ | H | —N= | —NH— | ≈N< | 3 |
| H | H | OCH₂CH₃ | H | —N= | —NH— | ≈N< | 4 |
| H | F | OCF₂H | H | —N= | —NH— | ≈N< | 5 |
| H | F | OCH₃ | F | —N= | —NH— | ≈N< | 6 |
| H | F | OCH₂CH₃ | H | —N= | —NH— | ≈N< | 7 |
| H | F | OCH₂F | H | —N= | —NH— | ≈N< | 8 |

-continued

| R¹ | R² | R³ | R⁴ | X | Y | R⁵/R⁶ | Ex. |
|---|---|---|---|---|---|---|---|
| H | H | OCH₃ | F | —N= | —NH— | pyrrolidinyl-CH₂-CH₂- | 9 |
| H | H | OCH₂CH₃ | H | —N= | —NH— | pyrrolidinyl-CH₂-CH₂- | 10 |
| H | H | Cl | H | —N= | —NH— | N(CH₃)CH₂-CH₂- | 11 |
| H | OCH₃ | H | CF₃ | —N= | —NH— | pyrrolidinyl-CH₂-CH₂- | 12 |
| H | H | OCF₃ | H | —N= | —NH— | pyrrolidinyl-CH₂-CH₂- | 13 |
| H | H | OCHF₂ | OCH₃ | —N= | —NH— | pyrrolidinyl-CH₂-CH₂- | 14 |
| OCH₃ | H | OCH₃ | H | —N= | —NH— | pyrrolidinyl-CH₂-CH₂- | 15 |
| H | F | F | H | —N= | —NH— | pyrrolidinyl-CH₂-CH₂- | 16 |

-continued

| R¹ | R² | R³ | R⁴ | X | Y | R⁵/R⁶ | Ex. |
|---|---|---|---|---|---|---|---|
| OCH₃ | OCH₃ | H | H | —N= | —NH— | -CH₂-pyrrolidinyl | 17 |
| H | OCH₃ | H | H | —N= | —NH— | -CH₂-pyrrolidinyl | 18 |
| H | OCH₃ | H | H | —N= | —NH— | -CH₂-pyrrolidinyl | 19 |
| H | H | together —O—(CH₂)₂—O— | | —N= | —NH— | -CH₂-pyrrolidinyl | 20 |
| H | H | together —O—CH₂—O— | | —N= | —NH— | -CH₂-pyrrolidinyl | 21 |
| H | H | F | H | —N= | —NH— | -CH₂-pyrrolidinyl | 22 |
| H | H | Br | H | —N= | —NH— | -CH₂-pyrrolidinyl | 23 |
| OCH₃ | H | Cl | Cl | —N= | —NH— | -CH₂-pyrrolidinyl | 24 |
| H | H | Cl | Cl | —N= | —NH— | -CH₂-pyrrolidinyl | 25 |
| H | H | together —HC=CH—CH=CH— | H | —N= | —NH— | -CH₂-pyrrolidinyl | |

-continued

| R¹ | R² | R³ | R⁴ | X | Y | R⁵/R⁶ | Ex. |
|---|---|---|---|---|---|---|---|
| H | H | —N(CH₃)₂ | H | —N= | —NH— | -CH₂-pyrrolidinyl | 26 |
| H | Cl | OCH₃ | H | —N= | —NH— | -CH₂-pyrrolidinyl | 27 |
| H | OCF₃ | H | H | —N= | —NH— | -CH₂-pyrrolidinyl | 28 |
| H | CF₃ | H | H | —N= | —NH— | -CH₂-pyrrolidinyl | 29 |
| H | Cl | H | H | —N= | —NH— | -CH₂-pyrrolidinyl | 30 |
| H | CF₃ | OCH₃ | H | —N= | —NH— | -CH₂-pyrrolidinyl | 31 |
| H | H | NO₂ | H | —N= | —NH— | -CH₂-pyrrolidinyl | 32 |
| H | together —CH₂—CH₂—CH₂— | | H | —N= | —NH— | -CH₂-pyrrolidinyl | 33 |

-continued

| R¹ | R² | R³ | R⁴ | X | Y | R⁵/R⁶ | Ex. |
|---|---|---|---|---|---|---|---|
| H | H | 1-pyrrolyl | H | —N= | —NH— | pyrrolidinylethyl | 34 |
| H | H | —OCH(CH₃)₂ | H | —N= | —NH— | pyrrolidinylethyl | 35 |
| H | H | together —O—CH₂—CH₂— | H | —N= | —NH— | pyrrolidinylethyl | 36 |
| H | OCH₃ | Cl | H | —N= | —NH— | pyrrolidinylethyl | 37 |
| H | OCHF₂ | H | H | —N= | —NH— | pyrrolidinylethyl | 38 |
| H | F | H | H | —N= | —NH— | pyrrolidinylethyl | 39 |
| H | H | CN | H | —N= | —NH— | pyrrolidinylethyl | 40 |
| H | OCH₃ | OCH₃ | H | —N= | —NH— | pyrrolidinylethyl | 41 |

-continued

| R¹ | R² | R³ | R⁴ | X | Y | R⁵/R⁶ | Ex. |
|---|---|---|---|---|---|---|---|
| H | OCH₃ | O-benzyl | H | —N= | —NH— | pyrrolidinyl-CH₂CH₂— | 42 |
| H | H | H | H | —N= | —NH— | dimethylamino-CH₂CH₂— | 43 |
| H | H | H | H | —N= | —NH— | pyrrolidinyl-CH₂CH₂— | 44 |
| F | H | H | H | —N= | —NH— | dimethylamino-CH₂CH₂— | 45 |
| F | H | H | H | —N= | —NH— | pyrrolidinyl-CH₂CH₂— | 46 |
| F | H | H | H | —N= | —NH— | morpholinyl-CH₂CH₂— | 47 |
| H | H | Cl | H | —N= | —NH— | dimethylamino-CH₂CH₂— | 48 |
| H | H | Cl | H | —N= | —NH— | pyrrolidinyl-CH₂CH₂— | 49 |

-continued

| R¹ | R² | R³ | R⁴ | X | Y | R⁵/R⁶ | Ex. |
|---|---|---|---|---|---|---|---|
| H | H | Cl | H | —N= | —NH— | morpholinoethyl | 50 |
| H | H | OCH₃ | H | —N= | —NH— | pyrrolidinoethyl | 51 |
| H | H | OCH₃ | H | —N= | —NH— | diethylaminoethyl | 52 |
| H | H | OCH₃ | H | —N= | —NH— | (3-hydroxypyrrolidino)ethyl | 53 |
| H | H | OCH₃ | H | —N= | —NH— | 2-hydroxyethylaminoethyl | 54 |
| H | H | OCH₃ | H | —N= | —NH— | N-methyl-N-ethylaminoethyl | 55 |
| H | H | OCH₃ | H | —N= | —NH— | N-allylaminoethyl | 56 |

-continued

| R¹ | R² | R³ | R⁴ | X | Y | R⁵/R⁶ | Ex. |
|---|---|---|---|---|---|---|---|
| H | H | OCH₃ | H | —N= | —NH— | piperidinyl-CH₂- | 57 |
| H | H | OCH₃ | H | —N= | —NH— | 3-(NHCOC)-pyrrolidinyl-CH₂- | 58 |
| H | H | OCH₃ | H | —N= | —NH— | CH₃NH-CH₂- | 59 |
| H | H | OCH₃ | H | —N= | —NH— | 3-methoxy-pyrrolidinyl-CH₂- | 60 |
| H | H | OCH₃ | H | —N= | —NH— | 4-benzyl-piperazinyl-CH₂- | 61 |
| H | H | OCH₃ | H | —N= | —NH— | 3-fluoro-pyrrolidinyl-CH₂- | 62 |
| H | H | OCH₃ | H | —N= | —NH— | azetidinyl-CH₂- | 63 |

-continued

| R¹ | R² | R³ | R⁴ | X | Y | R⁵/R⁶ | Ex. |
|---|---|---|---|---|---|---|---|
| H | H | OCH₃ | H | —N= | —NH— | piperidine N-substituted with 4-phenoxy, connected via ethyl | 64 |
| H | H | OCH₃ | H | —N= | —NH— | piperazine N-substituted with formyl, connected via ethyl | 65 |
| H | H | OCH₃ | H | —N= | —NH— | piperazine N-substituted with acetyl, connected via ethyl | 66 |
| H | H | OCH₃ | H | —N= | —NH— | 3-hydroxypiperidine, connected via ethyl | 67 |
| H | H | OCH₃ | H | —N= | —NH— | 4-hydroxypiperidine, connected via ethyl | 68 |

-continued

| R¹ | R² | R³ | R⁴ | X | Y | R⁵/R⁶ | Ex. |
|---|---|---|---|---|---|---|---|
| H | H | OCH₃ | H | —N= | —NH— | CH₂-pyrrolin-1-yl | 69 |
| H | H | CF₃ | H | —N= | —NH— | CH₂CH₂N(CH₃)₂ | 70 |
| H | Cl | Cl | H | —N= | —NH— | CH₂CH₂N(CH₃)₂ | 71 |
| H | H | OCH₃ | H | —N= | —NH— | CH₂CH₂NHCOCH₃ | 72 |
| H | H | OCH₃ | H | —N= | —NH— | CH₂CH₂NH₂ | 73 |
| H | H | OH | H | —N= | —NH— | CH₂CH₂N(CH₃)₂ | 74 |
| H | H | OCH₃ | H | —N= | —NH— | CH₂CH₂N(CH₃)₂ | 75 |
| OH | H | H | H | —N= | —NH— | CH₂-pyrrolidin-1-yl | 76 |

-continued

| R¹ | R² | R³ | R⁴ | X | Y | R⁵/R⁶ | Ex. |
|---|---|---|---|---|---|---|---|
| H | H | SO₂CH₃ | H | —N= | —NH— | pyrrolidinyl-ethyl | 77 |
| H | H | SCH₃ | H | —N= | —NH— | pyrrolidinyl-ethyl | 78 |
| H | OH | OCH₃ | H | —N= | —NH— | pyrrolidinyl-ethyl | 79 |
| H | O-benzyl | OCH₃ | H | —N= | —NH— | pyrrolidinyl-ethyl | 80 |
| H | H | OCH₃ | H | —N= | —NH— | 3-acetoxy-pyrrolidinyl-ethyl | 81 |
| H | Cl | Cl | H | —CH= | =N— | —CH₂CH₂NH₂ | 82 |
| H | Cl | Cl | H | —CH= | =N— | —CH₂CH₂NHCH₃ | 83 |
| H | Cl | Cl | H | —CH= | =N— | —CH₂CH₂N(CH₃)₂ | 84 |

-continued

| R¹ | R² | R³ | R⁴ | X | Y | R⁵/R⁶ | Ex. |
|---|---|---|---|---|---|---|---|
| H | Cl | Cl | H | —CH= | =N— | -CH₂CH₂-N(CH₃)-CH₂CH₂OH | 85 |
| H | Cl | Cl | H | —CH= | =N— | -CH₂CH₂-NH-CH₂CH₃ | 86 |
| H | Cl | Cl | H | —CH= | =N— | -CH₂CH₂-N(CH₃)-CH₂CH₃ | 87 |
| H | Cl | Cl | H | —CH= | =N— | -CH₂CH₂-N(CH₂CH₃)₂ | 88 |
| H | Cl | Cl | H | —CH= | =N— | -CH₂CH₂-NH-(CH₂)₄-O | 89 |
| H | Cl | Cl | H | —CH= | =N— | -CH₂CH₂-(pyrrolidinyl) | 90 |
| H | Cl | Cl | H | —CH= | =N— | -CH₂CH₂-NH-C(O)-CH₂OH | 91 |
| H | H | OCH₃ | H | —NH— | —CH= | -CH₂CH₂-NH₂ | 92 |

-continued

| R¹ | R² | R³ | R⁴ | X | Y | R⁵/R⁶ | Ex. |
|---|---|---|---|---|---|---|---|
| H | H | CH₃ | H | —NH— | —CH= | CH₂CH₂NH₂ | 93 |
| H | Cl | Cl | H | =N— | —CH= | CH₂CH₂NH₂ | 94 |
| H | H | together —CH=CH—CH=CH— | H | —NH— | —CH= | CH₂CH₂NH₂ | 95 |
| H | H | OCH₃ | H | —N(CH₃)— | =N— | CH₂CH₂N(CH₃)₂ | 96 |
| H | H | OCH₃ | H | =N— | —N(CH₃)— | CH₂CH₂N(CH₃)₂ | 97 |
| H | H | OCH₃ | H | —N(CH₃)— | =N— | CH₂CH₂-pyrrolidinyl | 98 |
| H | H | OCH₃ | H | =N— | —N(CH₃)— | CH₂CH₂-pyrrolidinyl | 99 |
| H | H | OCH₃ | H | —N(CH₃)— | =N— | CH₂CH₂-(2,5-dihydropyrrolyl) | 100 |
| H | H | OCH₃ | H | —N(CH₂CH₃)— | =N— | CH₂CH₂-pyrrolidinyl | 101 |

-continued

| R¹ | R² | R³ | R⁴ | X | Y | R⁵/R⁶ | Ex. |
|---|---|---|---|---|---|---|---|
| H | H | OCH₃ | H | —N= | —N(CH₂CH₃)— | pyrrolidinyl-CH₂CH₂- | 102 |
| H | H | OCH₃ | H | N(CH₂OCH₂CH₃)— | =N— | N(CH₃)₂-CH₂CH₂- | 103 |
| H | H | OCH₃ | H | —N(CH₂OCH₃)— | =N— | N(CH₃)₂-CH₂CH₂- | 104 |
| H | H | OCH₃ | H | —N[(CH₂)₂OH]— | =N— | N(CH₃)₂-CH₂CH₂- | 105 |
| H | H | OCH₃ | H | —N(CHF₂)— | =N— | N(CH₃)₂-CH₂CH₂- | 106 |
| H | H | OCH₃ | H | —N= | —N[(CH₂)₂OH]— | N(CH₃)₂-CH₂CH₂- | 107 |
| H | H | OCHF₂ | H | —N(CH₃)— | =N— | N(CH₃)₂-CH₂CH₂- | 108 |
| H | H | CH₃ | H | —N(CH₃)— | =N— | N(CH₃)₂-CH₂CH₂- | 109 |

-continued
| Ex. | R¹ | R² | R³ | R⁴ | X | Y | R⁵/R⁶ |
|---|---|---|---|---|---|---|---|
| 110 | H | Cl | Cl | H | —N= | N(CH₂)₂OH)— | 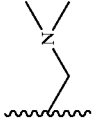 |
| 111 | H | Cl | Cl | H | —N[(CH₂)₂OH]— | =N— |  |
| 112 | H | F | OCH₃ | H | —N(CH₃)— | =N— | 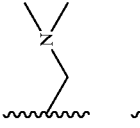 |
| 113 | H | H | OCH₃ | H | —N= | —N(CH₂CH(OH)CH₃)— | 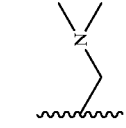 |
| 114 | H | H | OCH₃ | H | —N= | —N(CH₂C(O)CH₃)— |  |
| 115 | H | H | OCH₃ | H | —N(CH₂—CH=CH₂)— | =N— | 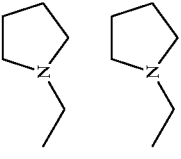 |
| 116 | H | H | OCH₃ | H | —N= | —N(CH₂CH=CH₂)— |  |
| 117 | H | H | OCH₃ | H | —N= | —N(CH₂C₆H₅)— |  |
| 118 | H | H | OCH₃ | H | —N= | —N(CH₃)— |  |

-continued
| R$^1$ | R$^2$ | R$^3$ | R$^4$ | X | Y | R$^5$/R$^6$ | Ex. |
|---|---|---|---|---|---|---|---|
| H | H | OCH$_3$ | H | —N(CH$_3$)— | =N— |  | 119 |
| H | H | OCH$_3$ | H | —N= | —N[(CH$_2$)$_2$C$_6$H$_5$]— |  | |
| H | H | OCH$_3$ | H | —N[(CH$_2$)$_2$C$_6$H$_5$]— | =N— |  | 120 |
| H | H | OCH$_3$ | H | —N(CH$_2$C(O)OCH$_2$CH$_3$)— | =N— |  | |
| H | H | OCH$_3$ | H | —N= | —N(CH$_2$C(O)OCH$_2$CH$_3$)— |  | 121 |
| H | H | OCH$_3$ | H | —N= | —N(CH$_2$—C≡CH)— |  | |
| H | H | OCH$_3$ | H | —N(CH$_2$—C≡CH)— | =N— | 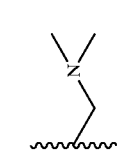 | 122 |
| H | H | OCH$_3$ | H | —N(CH$_2$CH$_3$)— | =N— |  | |

-continued
| R¹ | R² | R³ | R⁴ | X | Y | R⁵/R⁶ | Ex. |
|---|---|---|---|---|---|---|---|
| H | H | OCH₃ | H | —N= | —N(CH₂CH₃)— |  | 123 |
| H | H | OCH₃ | H | —N(CH₂–◁)— | =N— | 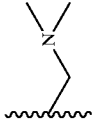 | |
| H | H | OCH₃ | H | —N= | —N(CH₂–◁)— | 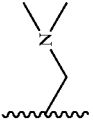 | 124 |
| H | H | OCH₃ | H | —N(CH₂C≡N)— | =N— |  | |
| H | H | OCH₃ | H | —N= | —N(CH₂C≡N)— |  | 125 |
| H | H | OCH₃ | H | —N(CH₂CH₂F)— | =N— |  | |
| H | H | OCH₃ | H | —N= | —N(CH₂CH₂F)— |  | 126 |
| H | H | OCH₃ | H | —N(CH₂–Ph)— | =N— | | |

-continued

| R¹ | R² | R³ | R⁴ | X | Y | R⁵/R⁶ | Ex. |
|---|---|---|---|---|---|---|---|
| H | H | OCH₃ | H | —N= | —N(CH₂–Ph)— | | |
| H | H | OCH₃ | H | —N[(CH₂)₂OH]— | =N— | | 127 |
| H | H | OCH₃ | H | —N= | —N[(CH₂)₂OH]— | | 128 |
| H | H | OCH₃ | H | —N(CH₂C(O)OCH₃)— | =N— | | |
| H | H | OCH₃ | H | —N= | —N(CH₂C(O)OCH₃)— | | 129 |
| H | H | OCH₃ | H | —N(CH₂–2-Py)— | =N— | | |
| H | H | OCH₃ | H | —N= | —N(CH₂–2-Py)— | | 130 |
| H | H | OCH₃ | H | —N(CH₂–3-Py)— | =N— | | |

-continued

| R¹ | R² | R³ | R⁴ | X | Y | R⁵/R⁶ | Ex. |
|---|---|---|---|---|---|---|---|
| H | H | OCH₃ | H | —N= | —N(CH₂)— | | |
| H | H | OCH₃ | H | —N(CH₂CHF₂)— | =N— | | 131 |
| H | H | OCH₃ | H | —N= | —N(CH₂CHF₂)— | | |
| H | H | OCH₃ | H | —N(CH₂)— | =N— | | 132 |
| H | H | OCH₃ | H | —N= | —N(CH₂)— | | |
| H | H | OCH₃ | H | —N[(CH₂)₃C≡N]— | =N— | | 133 |
| H | H | OCH₃ | H | —N= | —N[(CH₂)₃C≡N]— | | |
| H | H | OCH₃ | H | | =N— | | 134 |

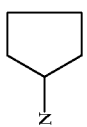

-continued

| R¹ | R² | R³ | R⁴ | X | Y | R⁵/R⁶ | Ex. |
|---|---|---|---|---|---|---|---|
| H | H | OCH₃ | H | —N= | —N(CH₂)—(C₆H₄-4-OCH₃) | -CH₂CH₂-N(CH₃)₂ | |
| H | H | OCH₃ | H | —N(CH₂)—(C₆H₄-4-OH) | =N— | -CH₂CH₂-N(CH₃)₂ | 139 |
| H | H | OCH₃ | H | —N= | —N(CH₂)—(C₆H₄-4-OH) | -CH₂CH₂-N(CH₃)₂ | |
| H | H | OCH₃ | H | —N(CH₂)—(C₆H₄-3-OCH₃) | =N— | -CH₂CH₂-N(CH₃)₂ | 140 |
| H | H | OCH₃ | H | —N= | —N(CH₂)—(C₆H₄-3-OCH₃) | -CH₂CH₂-N(CH₃)₂ | |
| H | H | OCH₃ | H | —N(CH=CH₂)— | =N— | -CH₂CH₂-N(CH₃)₂ | 141 |
| H | H | OCH₃ | H | —N= | —N(CH=CH₂)— | -CH₂CH₂-N(CH₃)₂ | |

EXAMPLE 1
{3-[5-(4-Difluoromethoxy-phenyl)-1H-[1,2,4]triazol-3-yl]-benzyl}dimethyl-amine hydrochloride (1:1)(mixture of tautomers)

To a freshly prepared solution of sodium ethoxide in ethanol (from sodium 0.4 g, 17.5 mmol, 150 ml) at 20° C. under an argon atmosphere was added 3-dimethylaminomethyl-benzamidine hydrochloride salt (1:2), (1.87 g, 7.5 mmol) portionwise and the resulting mixture was stirred at r.t. for 30 min. To this milky yellow suspension 4-difluoromethoxy-benzoic acid hydrazide (1.01 g, 5 mmol) was added and the mixture heated under reflux for 88 hrs. The solvent was evaporated and the crude orange product was chromatographed over $SiO_2$ (Merck 230–400 mesh) with $CH_2Cl_2$-MeOH (2M $NH_3$) 97:3. This afforded the free-base as a light yellow foam which was dissolved in ethanol and cooled to 4° C. HCl in ethanol (1.45M, 1.1 eq.) was added and the solution stirred for 30 min. The resulting precipitate was collected and washed with cold ethanol then dried under high vacuum at 50° C. to afford the title compound (0.4 g, 20% yield) as a white solid. MS: m/e= 345.4 (M+H$^+$)

Lit: J. E. Francis, H. Meckler, *Tetrahedron Lett.*, 1987, 28(43), 5133–6.

Examples 2 to 42 were Prepared According to the General Procedure Described in Example 1

EXAMPLE 2
{3-[5-(4-Fluoromethoxy-phenyl)-1H-[1,2,4]triazol-3-yl]-benzyl}-dimethyl-amine hydrochloride (1:1)(mixture of tautomers)

The title compound, MS: m/e=327.4 (M+H$^+$) was obtained as a light yellow foam by reaction of 3-dimethylaminomethyl-benzamidine hydrochloride salt (1:2) with 4-fluoromethoxy-benzoic acid hydrazide and subsequent preparation of the hydrochloride salt.

EXAMPLE 3
{3-[5-(3-Fluoro-4-methoxy-phenyl)-1H-[1,2,4]triazol-3-yl]-benzyl}-dimethyl-amine hydrochloride (1:1) (mixture of tautomers)

The title compound, MS: m/e=327.4 (M+H$^+$) was obtained as a light yellow solid by reaction of 3-dimethylaminomethyl-benzamidine hydrochloride salt (1:2) with 3-fluoro-4-methoxy-benzoic acid hydrazide and subsequent preparation of the hydrochloride salt.

EXAMPLE 4
{3-[5-(4-Ethoxy-phenyl)-1H-[1,2,4]triazol-3-yl]-benzyl}-dimethyl-amine hydrochloride (1:1) (mixture of tautomers)

The title compound, MS: m/e=323.4 (M+H$^+$) was obtained as a light yellow solid by reaction of 3-dimethylaminomethyl-benzamidine hydrochloride salt (1:2) with 4-ethoxy-benzoic acid hydrazide and subsequent preparation of the hydrochloride salt.

EXAMPLE 5
{3-[5-(4-Difluoromethoxy-3-fluoro-phenyl)-1H-[1,2,4]triazol-3-yl]-benzyl}-dimethyl-amine hydrochloride (1:1) (mixture of tautomers)

The title compound, MS: m/e=363.4 (M+H$^+$) was obtained as a light yellow solid by reaction of 3-dimethylaminomethyl-benzamidine hydrochloride salt (1:2) with 4-difluoromethoxy-3-fluoro-benzoic acid hydrazide and subsequent preparation of the hydrochloride salt.

EXAMPLE 6
{3-[5-(3,5-Difluoro-4-methoxy-phenyl)-1H-[1,2,4]triazol-3-yl]-benzyl}-dimethyl-amine hydrochloride (1:1) (mixture of tautomers)

The title compound, MS: m/e=345.4 (M+H$^+$) was obtained as off-white solid by reaction of 3-dimethylaminomethyl-benzamidine hydrochloride salt (1:2) with 3,5-difluoro-4-methoxy-benzoic acid hydrazide and subsequent preparation of the hydrochloride salt.

EXAMPLE 7
{3-[5-(4-Ethoxy-3-fluoro-phenyl)-1H-[1,2,4]triazol-3-yl]-benzyl}-dimethyl-amine hydrochloride (1:1) (mixture of tautomers)

The title compound, MS: m/e=341.4 (M+H$^+$) was obtained as a light yellow oil by reaction of 3-dimethylaminomethyl-benzamidine hydrochloride salt (1:2) with 4-ethoxy-3-fluoro-benzoic acid hydrazide and subsequent preparation of the hydrochloride salt.

EXAMPLE 8
{3-[5-(3-Fluoro-4-fluoromethoxy-phenyl)-1H-[1,2,4]triazol-3-yl]-benzyl}-dimethyl-amine hydrochloride (1:1) (mixture of tautomers)

The title compound, MS: m/e=345.4 (M+H$^+$) was obtained as a light yellow solid by reaction of 3-dimethylaminomethyl-benzamidine hydrochloride salt (1:2) with 3-fluoro-4-fluoromethoxy-benzoic acid hydrazide and subsequent preparation of the hydrochloride salt.

EXAMPLE 9
5-(3-Fluoro-4-methoxy-phenyl)-3-(3-pyrrolidin-1-ylmethyl-phenyl)-1H-[1,2,4]triazole hydrochloride (1:1) (mixture of tautomers)

The title compound, MS: m/e=353.4 (M+H$^+$) was obtained as a light yellow solid by reaction of 3-dimethylaminomethyl-benzamidine hydrochloride salt (1:2) with 3-fluoro-4-methoxy-benzoic acid hydrazide and subsequent preparation of the hydrochloride salt.

EXAMPLE 10
5-(4-Ethoxy-phenyl)-3-(3-pyrrolidin-1-ylmethyl-phenyl)-1H-[1,2,4]triazole hydrochloride (1:1) (mixture of tautomers)

The title compound, MS: m/e=349.5 (M+H$^+$) was obtained as a yellow foam by reaction of 3-pyrrolidin-1-ylmethyl-benzamidine hydrochloride salt (1:2) with 4-ethoxy-benzoic acid hydrazide and subsequent preparation of the hydrochloride salt.

EXAMPLE 11
{3-[5-(4-Chloro-3-trifluoromethyl-phenyl)-1H-[1,2,4]triazol-3-yl]-benzyl}-dimethyl-amine hydrochloride (1:1) (mixture of tautomers)

The title compound, MS: m/e=381.2 (M+H$^+$) was obtained as a light yellow foam by reaction of 3-dimethylaminomethyl-benzamidine hydrochloride salt (1:2) with 3-chloro-4-trifluoromethyl-benzoic acid hydrazide and subsequent preparation of the hydrochloride salt.

EXAMPLE 12
5-(3,5-Dimethoxy-phenyl)-3-(3-pyrrolidin-1-ylmethyl-phenyl)-1H-[1,2,4]triazole hydrochloride (1:1) (mixture of tautomers)

The title compound, MS: m/e=365.5 (M+H$^+$) was obtained as a light yellow foam by reaction of 3-pyrrolidin-1-ylmethyl-benzamidine hydrochloride salt (1:2) with 3,5-dimethoxybenzoic acid hydrazide and subsequent preparation of the hydrochloride salt.

EXAMPLE 13
3-(3-Pyrrolidin-1-ylmethyl-phenyl)-5-(4-trifluoromethoxy-phenyl)-1H-[1,2,4]triazole hydrochloride (1:1) (mixture of tautomers)

The title compound, MS: m/e=389.4 (M+H⁺) was obtained as a white solid by reaction of 3-pyrrolidin-1-ylmethyl-benzamidine hydrochloride salt (1:2) with 4-trifluoromethoxy-benzoic acid hydrazide and subsequent preparation of the hydrochloride salt.

EXAMPLE 14

5-(4-Difluoromethoxy-phenyl)-3-(3-pyrrolidin-1-ylmethyl-phenyl)-1H-[1,2,4]triazole hydrochloride (1:1) (mixture of tautomers)

The title compound, MS: m/e=371.4 (M+H⁺) was obtained as a light yellow solid by reaction of 3-pyrrolidin-1-ylmethyl-benzamidine hydrochloride salt (1:2) with 4-difluoromethoxy-benzoic acid hydrazide and subsequent preparation of the hydrochloride salt.

EXAMPLE 15

5-(2,4-Dimethoxy-phenyl)-3-(3-pyrrolidin-1-ylmethyl-phenyl)-1H-[1,2,4]triazole hydrochloride (1:1) (mixture of tautomers)

The title compound, MS: m/e=365.5 (M+H⁺) was obtained as a light yellow solid by reaction of 3-pyrrolidin-1-ylmethyl-benzamidine hydrochloride salt (1:2) with 2,4-dimethoxy-benzoic acid hydrazide and subsequent preparation of the hydrochloride salt.

EXAMPLE 16

5-(3,4-Difluoro-phenyl)-3-(3-pyrrolidin-1-ylmethyl-phenyl)-1H-[1,2,4]triazole hydrochloride (1:1) (mixture of tautomers)

The title compound, MS: m/e=341.4 (M+H⁺) was obtained as a light yellow solid by reaction of 3-pyrrolidin-1-ylmethyl-benzamidine hydrochloride salt (1:2) with 3,4-difluoro-benzoic acid hydrazide and subsequent preparation of the hydrochloride salt.

EXAMPLE 17

5-(2,3-Dimethoxy-phenyl)-3-(3-pyrrolidin-1-ylmethyl-phenyl)-1H-[1,2,4]triazole hydrochloride (1:1) (mixture of tautomers)

The title compound, MS: m/e=365.5 (M+H⁺) was obtained as a light yellow foam by reaction of 3-pyrrolidin-1-ylmethyl-benzamidine hydrochloride salt (1:2) with 2,3-dimethoxy-benzoic acid hydraz and subsequent preparation of the hydrochloride salt.

EXAMPLE 18

5-(3-Methoxy-phenyl)-3-(3-pyrrolidin-1-ylmethyl-phenyl)-1H-[1,2,4]triazole hydrochloride (1:1) (mixture of tautomers)

The title compound, MS: m/e=335.4 (M+H⁺) was obtained as a light yellow foam by reaction of 3-pyrrolidin-1-ylmethyl-benzamidine hydrochloride salt (1:2) with 3-methoxy-benzoic acid hydrazide and subsequent preparation of the hydrochloride salt.

EXAMPLE 19

5-(2,3-Dihydro-benzo[1,4]dioxin-6-yl)-3-(3-pyrrolidin-1-ylmethyl-phenyl)-1H-[1,2,4]triazole hydrochloride (1:1) (mixture of tautomers)

The title compound, MS: m/e=363.4 (M+H⁺) was obtained as a light yellow solid by reaction of 3-pyrrolidin-1-ylmethyl-benzamidine hydrochloride salt (1:2) with 2,3-dihydro-benzo[1,4]dioxine-6-carboxylic acid hydrazide and subsequent preparation of the hydrochloride salt.

EXAMPLE 20

5-Benzo[1,3-dioxol-5-yl-3-(3-pyrrolidin-1-ylmethyl-phenyl)-1H-[1,2,4]triazole hydrochloride (1:1) (mixture of tautomers)

The title compound, MS: m/e=349.4 (M+H⁺) was obtained as a light yellow solid by reaction of 3-pyrrolidin-1-ylmethyl-benzamidine hydrochloride salt (1:2) with 3,4-(methylenedioxy)benzo-hydrazide and subsequent preparation of the hydrochloride salt.

EXAMPLE 21

5-(4-Fluoro-phenyl)-3-(3-pyrrolidin-1-ylmethyl-phenyl)-1H-[1,2,4]triazole hydrochloride (1:1) (mixture of tautomers)

The title compound, MS: m/e=323.4 (M+H⁺) was obtained as a light yellow foam by reaction of 3-pyrrolidin-1-ylmethyl-benzamidine hydrochloride salt (1:2) with 4-fluorobenzoic acid hydrazide and subsequent preparation of the hydrochloride salt.

EXAMPLE 22

5-(4-Bromo-phenyl)-3-(3-pyrrolidin-1-ylmethyl-phenyl)-1H-[1,2,4]triazole hydrochloride (1:1) (mixture of tautomers)

The title compound, MS: m/e=384.3 (M+H⁺) was obtained as a light yellow foam by reaction of 3-pyrrolidin-1-ylmethyl-benzamidine hydrochloride salt (1:2) with 4-bromobenzoic acid hydrazide and subsequent preparation of the hydrochloride salt.

EXAMPLE 23

5-(4,5-Dichloro-2-methoxy-phenyl)-3-(3-pyrrolidin-1-ylmethyl-phenyl)-1H-[1,2,4]triazole hydrochloride (1:1) (mixture of tautomers)

The title compound, MS: m/e=403.4 (M+H⁺) was obtained as a light yellow foam by reaction of 3-pyrrolidin-1-ylmethyl-benzamidine hydrochloride salt (1:2) with 4,5-dichloro-2-methoxy-benzoic acid hydrazide and subsequent preparation of the hydrochloride salt.

EXAMPLE 24

5-(3,4-Dichloro-benzyl)-3-(3-pyrrolidin-1-ylmethyl-phenyl)-1H-[1,2,4]triazole hydrochloride (1:1) (mixture of tautomers)

The title compound, MS: m/e=387.2 (M+H⁺) was obtained as a light yellow solid by reaction of 3-pyrrolidin-1-ylmethyl-benzamidine hydrochloride salt (1:2) with (3,4-dichloro-phenyl)-acetic acid hydrazide and subsequent preparation of the hydrochloride salt.

EXAMPLE 25

5-Naphthalen-2-yl-3-(3-pyrrolidin-1-ylmethyl-phenyl)-1H-[1,2,4]triazole hydrochloride (1:1) (mixture of tautomers)

The title compound, MS: m/e=355.5 (M+H⁺) was obtained as a light yellow foam by reaction of 3-pyrrolidin-1-ylmethyl-benzamidine hydrochloride salt (1:2) with naphtalene-2-carboxylic acid hydrazide and subsequent preparation of the hydrochloride salt.

EXAMPLE 26

Dimethyl-{4-[5-(3-pyrrolidin-1-ylmethyl-phenyl)-2H-[1,2,4]triazol-3-yl]-phenyl}-amine hydrochloride (1:2) (mixture of tautomers)

The title compound, MS: m/e=348.5 (M+H⁺) was obtained as a light yellow foam by reaction of 3-pyrrolidin-1-ylmethyl-benzamidine hydrochloride salt (1:2) with 4-dimethylamino-benzoic acid hydrazide and subsequent preparation of the hydrochloride salt.

EXAMPLE 27

5-(3-Chloro-4-methoxy-phenyl)-3-(3-pyrrolidin-1-ylmethyl-phenyl)-1H-[1,2,4]triazole hydrochloride (1:1) (mixture of tautomers)

The title compound, MS: m/e=369.3 (M+H⁺) was obtained as a yellow foam by reaction of 3-pyrrolidin-1-ylmethyl-benzamidine hydrochloride salt (1:2) with 3-chloro-4-methoxy-benzoic acid hydrazide and subsequent preparation of the hydrochloride salt.

EXAMPLE 28

3-(3-Pyrrolidin-1-ylmethyl-phenyl)-5-(3-trifluoromethoxy-phenyl)-1H-[1,2,4]triazole hydrochloride (1:1) (mixture of tautomers)

The title compound, MS: m/e=389.4 (M+H⁺) was obtained as a white solid by reaction of 3-pyrrolidin-1-ylmethyl-benzamidine hydrochloride salt (1:2) with 3-trifluoromethoxy-benzoic acid hydrazide and subsequent preparation of the hydrochloride salt.

EXAMPLE 29

3-(3-Pyrrolidin-1-ylmethyl-phenyl)-5-(3-trifluoromethyl-phenyl)-1H-[1,2,4]triazole hydrochloride (1:1) (mixture of tautomers)

The title compound, MS: m/e=373.4 (M+H⁺) was obtained as a white foam by reaction of 3-pyrrolidin-1-ylmethyl-benzamidine hydrochloride salt (1:2) with 3-trifluoromethoxy-benzoic acid hydrazide and subsequent preparation of the hydrochloride salt.

EXAMPLE 30

5-(3-Chloro-phenyl)-3-(3-pyrrolidin-1-ylmethyl-phenyl)-1H-[1,2,4]triazole hydrochloride (1:1) (mixture of tautomers)

The title compound, MS: m/e=339.2 (M+H⁺) was obtained as a white solid by reaction of 3-pyrrolidin-1-ylmethyl-benzamidine hydrochloride salt (1:2) with 3-chlorobenzoic acid hydrazide and subsequent preparation of the hydrochloride salt.

EXAMPLE 31

5-(4-Methoxy-3-trifluoromethyl-phenyl)-3-(3-pyrrolidin-1-ylmethyl-phenyl)-1H-[1,2,4]triazole hydrochloride (1:1) (mixture of tautomers)

The title compound, MS: m/e=403.4 (M+H⁺) was obtained as a white solid by reaction of 3-pyrrolidin-1-ylmethyl-benzamidine hydrochloride salt (1:2) with 4-methoxy-3-trifluoromethyl-benzoic acid hydrazide and subsequent preparation of the hydrochloride salt.

EXAMPLE 32

5-(4-Nitro-phenyl)-3-(3-pyrrolidin-1-ylmethyl-phenyl)-1H-[1,2,4]triazole hydrochloride (1:1) (mixture of tautomers)

The title compound, MS: m/e=350.4 (M+H⁺) was obtained as a light yellow solid by reaction of 3-pyrrolidin-1-ylmethyl-benzamidine hydrochloride salt (1:2) with 4-nitrobenzoic acid hydrazide and subsequent preparation of the hydrochloride salt.

EXAMPLE 33

5-Indan-5-yl-3-(3-pyrrolidin-1-ylmethyl-phenyl)-1H-[1,2,4]triazole hydrochloride (1:1) (mixture of tautomers)

The title compound, MS: m/e=345.5 (M+H⁺) was obtained as a light yellow foam by reaction of 3-pyrrolidin-1-ylmethyl-benzamidine hydrochloride salt (1:2) with indan-5-carboxylic acid hydrazide and subsequent preparation of the hydrochloride salt.

EXAMPLE 34

3-(3-Pyrrolidin-1-ylmethyl-phenyl)-5-(4-pyrrol-1-yl-phenyl)-1H-[1,2,4]triazole hydrochloride (1:2) (mixture of tautomers)

The title compound, MS: m/e=370.5 (M+H⁺) was obtained as a light yellow foam by reaction of 3-pyrrolidin-1-ylmethyl-benzamidine hydrochloride salt (1:2) with 4-pyrrol-1-yl-benzoic acid hydrazide and subsequent preparation of the hydrochloride salt.

EXAMPLE 35

5-(4-Isopropoxy-phenyl)-3-(3-pyrrolidin-1-ylmethyl-phenyl)-1H-[1,2,4]triazole hydrochloride (1:1) (mixture of tautomers)

The title compound, MS: m/e=363.5 (M+H⁺) was obtained as a light yellow solid by reaction of 3-pyrrolidin-1-ylmethyl-benzamidine hydrochloride salt (1:2) with 4-isopropoxy-benzoic acid hydrazide and subsequent preparation of the hydrochloride salt.

EXAMPLE 36

5-(2,3-Dihydro-benzofuran-5-yl)-3-(3-pyrrolidin-1-ylmethyl-phenyl)-1H-[1,2,4]triazole hydrochloride (1:1) (mixture of tautomers)

The title compound, MS: m/e=347.4 (M+H⁺) was obtained as a light yellow foam by reaction of 3-pyrrolidin-1-ylmethyl-benzamidine hydrochloride salt (1:2) with 2,3-dihydro-benzofuran-5-carboxylic acid hydrazide and subsequent preparation of the hydrochloride salt.

EXAMPLE 37

5-(4-Chloro-3-methoxy-phenyl)-3-(3-pyrrolidin-1-ylmethyl-phenyl)-1H-[1,2,4]triazole hydrochloride (1:1) (mixture of tautomers)

The title compound, MS: m/e=369.3 (M+H⁺) was obtained as a white solid by reaction of 3-pyrrolidin-1-ylmethyl-benzamidine hydrochloride salt (1:2) with 4-chloro-3-methoxy-benzoic acid hydrazide and subsequent preparation of the hydrochloride salt.

EXAMPLE 38

5-(3-Difluoromethoxy-phenyl)-3-(3-pyrrolidin-1-ylmethyl-phenyl)-1H-[1,2,4]triazole hydrochloride (1:1) (mixture of tautomers)

The title compound, MS: m/e=371.4 (M+H⁺) was obtained as a white solid by reaction of 3-pyrrolidin-1-ylmethyl-benzamidine hydrochloride salt (1:2) with 3-difluoromethoxy-benzoic acid hydrazide and subsequent preparation of the hydrochloride salt.

EXAMPLE 39

5-(3-Fluoro-phenyl)-3-(3-pyrrolidin-1-ylmethyl-phenyl)-1H-[1,2,4]triazole hydrochloride (1:1) (mixture of tautomers)

The title compound, MS: m/e=323.4 (M+H⁺) was obtained as a white foam by reaction of 3-pyrrolidin-1-ylmethyl-benzamidine hydrochloride salt (1:2) with 3-fluoro-benzoic acid hydrazide and subsequent preparation of the hydrochloride salt.

EXAMPLE 40

4-[5-(3-Pyrrolidin-1-ylmethyl-phenyl)-2H-[1,2,4]triazol-3-yl]-benzonitrile hydrochloride (1:1) (mixture of tautomers)

The title compound, MS: m/e=330.4 (M+H⁺) was obtained as a light yellow foam by reaction of 3-pyrrolidin-1-ylmethyl-benzamidine hydrochloride salt (1:2) with 4-cyanobenzoic acid hydrazide and subsequent preparation of the hydrochloride salt.

EXAMPLE 41

5-(3,4-Dimethoxy-phenyl)-3-(3-pyrrolidin-1-ylmethyl-phenyl)-1H-[1,2,4]triazole hydrochloride (1:1) (mixture of tautomers)

The title compound, MS: m/e=365.5 (M+H$^+$) was obtained as a light yellow solid by reaction of 3-pyrrolidin-1-ylmethyl-benzamidine hydrochloride salt (1:2) with 3,4-dimethoxybenzoic acid hydrazide and subsequent preparation of the hydrochloride salt.

EXAMPLE 42
5-(4-Benzyloxy-3-methoxy-phenyl)-3-(3-pyrrolidin-1-ylmethyl-phenyl)-1H-[1,2,4]triazole hydrochloride (1:1) (mixture of tautomers)

The title compound, MS: m/e=441.6 (M+H$^+$) was obtained as a light yellow solid by reaction of 3-pyrrolidin-1-ylmethyl-benzamidine hydrochloride salt (1:2) with 4-benzyloxy-3-methoxy-benzoic acid hydrazide and subsequent preparation of the hydrochloride salt.

EXAMPLE 43
Dimethyl-[3-(5-phenyl-1H-[1,2,4]triazol-3-yl)-benzyl]-amine hydrochloride (1:1)

To a stirred ethanolic suspension of benzamidine hydrochloride salt (235 mg, 1.5 mmol, 1.5 eq.), was added 1.2N NaOEt in ethanol (1.7 ml, 2 eq.) over 3 minutes, the mixture was further stirred for 30 min. at r.t. To this was added 3-dimethylaminomethyl-benzoic acid hydrazide (193 mg, 1 mmol) in ethanol at 20° C. and the mixture heated to reflux for 24 hrs. Upon cooling the product mixture was filtered, solvent evaporated and residue subjected to preparative reversed-phase HPLC purification using a YMC ODS-AQ column (20×50 mm) and a (0.1% trifluoroacetic acid) water-acetonitrile gradient (25 ml/min. flow rate). The pure fractions were concentrated and the product obtained was converted to the hydrochloride salt by addition of excess 2N HCl/ether solution (1.0 ml) followed by solvent evaporation and high vacuum drying to afford the title compound (84 mg, 0.27 mmol, 27% yield) as a yellow foam. MS: m/e=279.4 (M+H$^+$).

Examples 44 to 51 were Prepared According to the General Procedure Described in Example 43

EXAMPLE 44
5-Phenyl-3-(3-pyrrolidin-1-ylmethyl-phenyl)-1H-[1,2,4]triazole hydrochloride (1:1)

The title compound, MS: m/e=279.4 (M+H$^+$) was obtained as a yellow foam by reaction of benzamidine hydrochloride salt with 3-pyrrolidin-1-ylmethyl-benzoic acid hydrazide and subsequent preparation of the hydrochloride salt.

EXAMPLE 45
{3-5-(2-Fluoro-phenyl)-1H-[1,2,4]triazol-3-yl 1-benzyl}-dimethyl-amine hydrochloride (1:1) (mixture of tautomers)

The title compound, MS: m/e=297.4 (M+H$^+$) was obtained as a yellow foam by reaction of 2-fluorobenzamidine hydrochloride salt with 3-dimethylaminomethyl-benzoic acid hydrazide and subsequent preparation of the hydrochloride salt.

EXAMPLE 46
5-(2-Fluoro-phenyl)-3-(3-pyrrolidin-1-ylmethyl-phenyl)-1H-[1,2,4]triazole hydrochloride (1:1) (mixture of tautomers)

The title compound, MS: m/e=323.4 (M+H$^+$) was obtained as a yellow foam by reaction of 2-fluorobenzamidine hydrochloride salt with 3-pyrrolidin-1-ylmethyl-benzoic acid hydrazide and subsequent preparation of the hydrochloride salt.

EXAMPLE 47
4-{3-[5-(2-Fluoro-phenyl)-1H-[1,2,4]triazol-3-yl]-benzyl}-morpholine hydrochloride (1:1) (mixture of tautomers)

The title compound, MS: m/e=339.4 (M+H$^+$) was obtained as a yellow foam by reaction of 2-fluorobenzamidine hydrochloride salt with 3-morpholin-4-ylmethyl-benzoic acid hydrazide and subsequent preparation of the hydrochloride salt.

EXAMPLE 48
{3-[5-(4-Chloro-phenyl)-1H-[1,2,4]triazol-3-yl]-benzyl}-dimethyl-amine hydrochloride (1:1) (mixture of tautomers)

The title compound, MS: m/e=313.2 (M+H$^+$) was obtained as a light yellow foam by reaction of 4-chlorobenzamidine hydrochloride salt with 3-dimethylaminomethyl-benzoic acid hydrazide and subsequent preparation of the hydrochloride salt.

EXAMPLE 49
5-(4-Chloro-phenyl)-3-(3-pyrrolidin-1-ylmethyl-phenyl)-1H-[1,2,4]triazole hydrochloride (1:1) (mixture of tautomers)

The title compound, MS: m/e=339.2 (M+H$^+$) was obtained as a light yellow foam by reaction of 4-chlorobenzamidine hydrochloride salt with 3-pyrrolidin-1-ylmethyl-benzoic acid hydrazide and subsequent preparation of the hydrochloride salt.

EXAMPLE 50
4-{3-[5-(4-Chloro-phenyl)-1H-[1,2,4]triazol-3-yl]-benzyl}-morpholine hydrochloride (1:1) (mixture of tautomers)

The title compound, MS: m/e=355.3 (M+H$^+$) was obtained as a light yellow foam by reaction of 4-chlorobenzamidine hydrochloride salt with 3-morpholin-4-ylmethyl-benzoic acid hydrazide and subsequent preparation of the hydrochloride salt.

EXAMPLE 51
5-(4-Methoxy-phenyl)-3-(3-pyrrolidin-1-ylmethyl-phenyl)-1H-[1,2,4]triazole hydrochloride (1:1) (mixture of tautomers)

The title compound, MS: m/e=335.4 (M+H$^+$) was obtained as a white foam by reaction of 4-methoxybenzamidine hydrochloride salt with 3-pyrrolidin-1-ylmethyl-benzoic acid hydrazide and subsequent preparation of the hydrochloride salt.

EXAMPLE 52
Diethyl-{3-[5-(4-methoxy-phenyl)-1H-[1,2,4]triazol-3-yl]-benzyl}-amine hydrochloride (1:1) (mixture of tautomers)

To a stirred solution of 3-[5-(4-methoxy-phenyl)-1H-[1,2,4]triazol-3-yl]-benzaldehyde (200 mg, 0.72 mmol) in THF (20 ml) under argon diethylamine (63 mg, 0.86 mmol, 1.2 eq.), acetic acid (52 mg, 0.86 mmol, 1.2 eq.) and sodium triacetoxyborohydride (228 mg, 1.07 mmol, 1.5 eq.) were added. The resulting suspension was vigorously stirred at r.t. for 24 hrs. under argon, 5% NaHCO$_3$ (10 ml) was then added and the mixture stirred for a further 10–15 min, then extracted with ethylacetate (20 ml). The organic phase was washed with saturated brine then dried with sodium sulfate. After removal of the solvent the residue was chromatographed over 20 g SiO$_2$ (Merck 230–400 mesh) with CH$_2$Cl$_2$-MeOH (2M NH$_3$) 96:4, affording a foam after evaporation. This material was dissolved in methanol at r.t. and an excess of 2N HCl/ether solution (1.0 ml, 2 mmol) was added. After stirring for 5 min. the solvent was evaporated and the residue was dried under high vacuum at 30° C. overnight affording the title compound (205 mg, 77% yield) as a white foam. MS: m/e=337.4 (M+H$^+$)

Examples 53 to 61 were Prepared According to the General Procedure Described in Example 52

EXAMPLE 53

(RS)-1-{3-[5-(4-Methoxy-phenyl)-1H-[1,2,4]triazol-3-yl]-benzyl}-pyrrolidin-3-ol hydrochloride (1:1) (mixture of tautomers)

The title compound, MS: m/e=351.4 (M+H$^+$) was obtained as a white solid by reaction of 3-[5-(4-methoxy-phenyl)-1H-[1,2,4]triazol-3-yl]-benzaldehyde with (RS)3-pyrrolidin and subsequent preparation of the hydrochloride salt.

EXAMPLE 54

2-{3-[5-(4-Methoxy-phenyl)-1H-[1,2,4]triazol-3-yl]-benzylamino}-ethanol hydrochloride (1:1) (mixture of tautomers)

The title compound, MS: m/e=325.4 (M+H$^+$) was obtained as a white solid by reaction of 3-[5-(4-methoxy-phenyl)-1H-[1,2,4]triazol-3-yl]-benzaldehyde with ethanolamine a subsequent preparation of the hydrochloride salt.

EXAMPLE 55

Ethyl-{3-[5-(4-methoxy-phenyl)-1H-[1,2,4]triazol-3-yl]-benzyl}-methyl-amine hydrochloride (1:1) (mixture of tautomers)

The title compound, MS: m/e=323.4 (M+H$^+$) was obtained as a light yellow foam by reaction of 3-[5-(4-methoxy-phenyl)-1H-[1,2,4]triazol-3-yl]-benzaldehyde with N-ethymethylamine and subsequent preparation of the hydrochloride salt.

EXAMPLE 56

Allyl-{3-[5-(4-methoxy-phenyl)-1H-[1,2,4]triazol-3-yl]-benzyl}-amine hydrochloride (1:1) (mixture of tautomers)

The title compound, MS: m/e=321.4 (M+H$^+$) was obtained as a light yellow solid by reaction of 3-[5-(4-methoxy-phenyl)-1H-[1,2,4]triazol-3-yl]-benzaldehyde with allylamine and subsequent preparation of the hydrochloride salt.

EXAMPLE 57

1-{3-[5-(4-Methoxy-phenyl)-1H-[1,2,4]triazol-3-yl]-benzyl}-piperidine hydrochloride (1:1) (mixture of tautomers)

The title compound, MS: m/e=349.5 (M+H$^+$) was obtained as a light yellow foam by reaction of 3-[5-(4-methoxy-phenyl)-1H-[1,2,4]triazol-3-yl]-benzaldehyde with piperidine and subsequent preparation of the hydrochloride salt.

EXAMPLE 58

(S)-N-(1{3-[5-(4-Methoxy-phenyl)-1H-[1,2,4]triazol-3-yl]-benzyl}-pyrrolidin-3-yl)-acetamide hydrochloride (1:1) (mixture of tautomers)

The title compound, MS: m/e=392.5 (M+H$^+$) was obtained as a light yellow foam by reaction of 3-[5-(4-methoxy-phenyl)-1H-[1,2,4]triazol-3-yl]-benzaldehyde with (3S)-(−)-3-acetamidopyrrolidine and subsequent preparation of the hydrochloride salt.

EXAMPLE 59

{3-[5-(4-Methoxy-phenyl)-1H-[1,2,4]triazol-3-yl]-benzyl}-methyl-amine hydrochloride (1:1) (mixture of tautomers)

The title compound, MS: m/e=295.4 (M+H$^+$) was obtained as a white solid by reaction of 3-[5-(4-methoxy-phenyl)-1H-[1,2,4]triazol-3-yl]-benzaldehyde with methylamine hydrochloride (2 eq.) and triethylamine (2 eq.) followed by preparation of the hydrochloride salt.

EXAMPLE 60

(RS)-5-(4-Methoxy-phenyl)-3-[3-(3-methoxy-pyrrolidin-1-ylmethyl)-phenyl]-1H[1,2,4]triazole hydrochloride (1:1) (mixture of tautomers)

The title compound, MS: m/e=365.2 (M+H$^+$) was obtained as a light brown foam by reaction of 3-[5-(4-methoxy-phenyl)-1H-[1,2,4]triazol-3-yl]-benzaldehyde with (RS) 3-methoxy pyrrolidine hydrochloride salt (1.5 eq.) and triethylamine (1.5 eq.) followed by preparation of the hydrochloride salt.

EXAMPLE 61

1-Benzyl-4-{3-[5-(4-methoxy-phenyl)-1H-[1,2,4]triazol-3-yl]-benzyl}-piperazine (mixture of tautomers)

The title compound, MS: m/e=440.5 (M+H$^+$) was obtained as a white foam by reaction of 3-[5-(4-methoxy-phenyl)-1H-[1,2,4]triazol-3-yl]-benzaldehyde with 1-N-benzyl piperazine hydrochloride salt (1:2) (1.2 eq.) and triethylamine (2.5 eq).

EXAMPLE 62

(RS)-3-[3-(3-Fluoro-pyrrolidin-1-ylmethyl)-phenyl]-5-(4-methoxy-phenyl)-1H-[1,2,4]triazole (mixture of tautomers)

To a stirred solution of of 3-[5-(4-methoxy-phenyl)-1H-[1,2,4]triazol-3-yl]-benzaldehyde (150 mg, 0.54 mmol) in THF (5 ml) under argon (RS)3-fluoro-pyrrolidine hydrochloride salt (81 mg, 0.64 mmol, 1.2 eq.), triethylamine (65 mg, 0.64 mmol, 1.2 eq.) were added. After 5 min. acetic acid (39 mg, 0.64 mmol, 1.2 eq.) and sodium triacetoxyborohydride (171 mg, 0.81 mmol, 1.5 eq.) were added. The resulting suspension was vigorously stirred at r.t. for 19 hrs. under argon. 5% NaHCO$_3$ (20 ml) was then added and the mixture stirred for 10–15 min., then extracted with ethylacetate (20 ml). The organic phase was washed with saturated brine then dried with sodium sulfate. After removal of the solvent, the residue was dried under high vacuum at 20° C., affording the title compound (194 mg, 0.50 mmol, 93% yield) as a yellow oil. MS: m/e=353.3 (M+H$^+$)

Examples 63 to 69 were Prepared Following the General Procedure of Example 62

EXAMPLE 63

3-(3-Azetidin-1-ylmethyl-phenyl)-5-(4-methoxy-phenyl)-1H-[1,2,4]triazole (mixture of tautomers)

The title compound, MS: m/e=321.3 (M+H$^+$) was obtained as a light yellow oil by reaction of 3-[5-(4-methoxy-phenyl)-1H-[1,2,4]triazol-3-yl]-benzaldehyde with azetidine (trimethylene imine).

EXAMPLE 64

1-{3-[5-(4-Methoxy-phenyl)-1H-[1,2,4]triazol-3-yl]-benzyl}-4-phenoxy-piperidine (mixture of tautomers)

The title compound, MS: m/e=441.4 (M+H$^+$) was obtained as a light yellow foam by reaction of 3-[5-(4-methoxy-phenyl)-1H-[1,2,4]triazol-3-yl]-benzaldehyde with 4-pheonxy-piperidine hydrochlo-ride (1.2 eq.) and triethylamine (1.2 eq.).

EXAMPLE 65

4-{3-[5-(4-Methoxy-phenyl)-1H-[1,2,4]triazol-3-yl]-benzyl}-piperazine-1-carbaldehyde (mixture of tautomers)

The title compound, MS: m/e=378.4 (M+H$^+$) was obtained as a yellow foam by reaction of 3-[5-(4-methoxy-phenyl)-1H-[1,2,4]triazol-3-yl]-benzaldehyde with 1-formyl piperazine.

EXAMPLE 66

1-(4-{3-[5-(4-Methoxy-phenyl)-1H-[1,2,4]triazol-3-yl]-benzyl}-piperazin-1-yl)-ethanone (mixture of tautomers)

The title compound, MS: m/e=392.5 (M+H$^+$) was obtained as a white foam by reaction of 3-[5-(4-methoxy-phenyl)-1H-[1,2,4]triazol-3-yl]-benzaldehyde with 1-acetyl piperazine.

EXAMPLE 67
(RS)-1-{3-[5-(4-Methoxy-phenyl)-1H-[1,2,4triazol-3-yl]-benzyl}-piperidin-3-ol (mixture of tautomers)

The title compound, MS: m/e=365.3 (M+H$^+$) was obtained as a white foam by reaction of 3-[5-(4-methoxy-phenyl)-1H-[1,2,4]triazol-3-yl]-benzaldehyde with 3-hydroxpiperdine.

EXAMPLE 68
1-{3-[5-(4-Methoxy-phenyl)-1H-[1,2,4]triazol-3-yl]-benzyl}-piperidin-4-ol (mixture of tautomers)

The title compound, MS: m/e=365.3 (M+H$^+$) was obtained as a white foam by reaction of 3-[5-(4-methoxy-phenyl)-1H-[1,2,4]triazol-3-yl]-benzaldehyde with 4-hydroxypipe

EXAMPLE 69
2:1 mixture of 3-[3-(2,5-Dihydro-pyrrol-1-ylmethyl)-phenyl]-5-(4-methoxy-phenyl)-1H-[1,2,4]triazole and 5-(4-Methoxy-phenyl)-3-(3-pyrrolidin-1-ylmethyl-phenyl)-1H-[1,2,4]triazole (mixtures of tautomers)

The title compound, MS: m/e=333.3 (M+H$^+$) was obtained as a yellow foam by reaction of 3-[5-(4-methoxy-phenyl)-1H-[1,2,4]triazol-3-yl]-benzaldehyde with 2,5-dihydro-1H-pyrrole.

EXAMPLE 70
Dimethyl-{3-[5-(4-trifluoromethyl-phenyl)-1H-[1,2,4]triazol-3-yl]-benzyl}-amine hydrochloride (1:1) (mixture of tautomers)

To an ethanolic suspension of 4-trifluoromethyl-benzimidic acid ethyl ester hydrochloride salt (761 mg, 3.0 mmol, 1.5 eq.) was added sodium methoxide (162 mg, 3 mmol) in ethanol (20 ml.) and the resulting mixture stirred for 30 min.at r.t. 3-dimethylaminomethyl-benzoic acid hydrazide (386 mg, 2.0 mmol) in ethanol was then added at 20° C., followed by heating to reflux for 16 hrs. Upon cooling, the product mixture was filtered, solvent was evaporated and the residue subjected to preparative reversed-phase HPLC purification using a YMC ODS-AQ column (20×50 mm) and a (0.1% trifluoroacetic acid) water-acetonitrile gradient (25 ml/min. flow rate). The pure fractions were concentrated and the product obtained was converted to the hydrochloride salt in ether by addition of excess 5N HCl/iPrOH solution (1 ml) followed by solvent evaporation and high vacuum drying to afford the title compound (79 mg, 0.21 mmol, 10% yield) as a white foam. MS: m/e=347.4 (M+H$^+$).

Example 71 was Prepared Following the General Method of Example 70

EXAMPLE 71
{3-[5-(3,4-Dichloro-phenyl)-1H-[1,2,4]triazol-3-yl]-benzyl}-dimethyl-amine hydrochloride (1:1)

The title compound, MS: m/e=347.3 (M+H$^+$) was obtained as a white solid by reaction of 3,4-dichloro-benzimidic acid ethyl ester hydrochloride salt with 3-dimethylaminomethyl-benzoic acid hydrazide and subsequent preparation of the hydrochloride salt.

EXAMPLE 72
N-{3-[5-(4-Methoxy-phenyl)-1H-[1,2,4]triazol-3-yl]-benzyl}-acetamide A solution of 3-[5-(4-methoxy-phenyl)-1H-[1,2,4]triazol-3-yl]-benzylamine hydrochloride (1:1) (50 mg, 0.016 mmol) and triethylamine (32 mg, 0.032 mmol) in CH$_2$Cl$_2$ (5 ml) was stirred at r.t. for 30 min. Acetyl chloride (12 mg, 0.016 mmol) was then added and the mixture stirred for 1.5 hrs. The reaction mixture was evaporated and chromatographed over SiO$_2$ (Merck 230–400 mesh) with CH$_2$Cl$_2$-MeOH (2M NH$_3$) 96:4. This afforded a yellow oil, which was then dried under high vacuum at 50° C. to afford the title compound (41 mg, 72% yield) as a light yellow solid. MS: m/e=323.3 (M+H$^+$).

EXAMPLE 73
3-[5-(4-Methoxy-phenyl)-1H-[1,2,4]triazol-3-yl]-benzylamine hydrochloride (1:1) (mixture of tautomers)

A solution of 3-(3-azidomethyl-phenyl)-5-(4-methoxy-phenyl)-1H-[1,2,4]triazole (980 mg, 3.2 mmol) in acetonitrile (40 ml) was treated with triphenyl phosphine (839 mg, 3.2 mmol) and water (288 mg, 16 mmol) at 20° C. for 20 min, then for 30 min. at 60° C. Upon cooling the product mixture was filtered, the solvent was evaporated and the residue chromatographed over 20 g SiO$_2$ (Merck 230–400 mesh) with CH$_2$Cl$_2$-MeOH (2M NH$_3$) 97:3 affording a solid after evaporation of the solvent. This material was dissolved in ethanol at r.t. and an excess 2N HCl/ether solution (2.0 ml, 4 mmol) was added. After 30 min. the precipitate was filtered off, washed with ether and dried under high vacuum at 60° C. overnight affording the title compound (700 mg, 69% yield) as a white solid. MS: m/e=281.3 (M+H$^+$).

EXAMPLE 74
4-[5-(3-Dimethylaminomethyl-phenyl)-2H-[1,2,4]triazol-3-yl]-phenol hydrochloride salt 1:1 (mixture of tautomers)

A solution of {3-[5-(4-methoxy-phenyl)-1H-[1,2,4]triazol-3-yl]-benzyl}-dimethylamine hydrochloride (1:1) (100 mg, 0.29 mmol) in CH$_2$Cl$_2$ (5 ml) at −78° C. was treated with boron tribromide (1M CH$_2$Cl$_2$ 1.5 ml, 1.5 mmol, 5.2 eq.). Over 16 hrs. the temperature was raised gradually to r.t. After addition of methanol (1 ml) and saturated Na$_2$CO$_3$ (10 ml) the pH was adjusted to 9 with 2N HCl. After extraction with CH$_2$Cl$_2$, then EtOAc, the combined extracts were dried with Na$_2$SO$_4$ and the solvent evaporated. The residue was dissolved in EtOH, 1.45M HCl/EtOH added (0.17 ml, 1.1 eq.) and stirred for 30 min. then evaporated to dryness and the product obtained was dried under high vacuum at 20° C., affording the title compound (70 mg, 73% yield) as a light yellow solid. MS: m/e=295.3 (M+H$^+$).

EXAMPLE 75
{3-[5-(4-Methoxy-phenyl)-1H-[1,2,4]triazol-3-yl]-benzyl}-dimethyl-amine hydrochloride (1:1) (mixture of tautomers)

To a stirred ethanolic suspension of 4-methoxybenzamidine hydrochloride salt (280 mg, 1.5 mmol, 1.5 eq.) was added over 3 minutes 1.2N NaOEt in ethanol (1.7 ml, 2 eq.) and stirring was continued for 30 min. at r.t. 3-Dimethylaminomethyl-benzoic acid hydrazide (193 mg, 1 mmol) in ethanol was then added at 20° C. and the mixture heated at reflux for 24 hrs. Upon cooling the product mixture was filtered, the solvent was evaporated and the residue subjected to preparative reversed phase-HPLC purification using a YMC ODS-AQ column (20×50 mm) and a (0.1% trifluoroacetic acid) water-acetonitrile gradient (25 ml/min.). The pure fractions were concentrated and the product obtained was converted to the hydrochloride salt by addition of excess 2N HCl/ether solution. Solvent evaporation and high vacuum drying afforded the title compound (86 mg, 0.25 mmol, 25% yield) as a white foam. MS: m/e=309.4 (M+H$^+$).

Example 76 was Prepared Following the General Procedure of Example 74

EXAMPLE 76
2-[5-(3-Pyrrolidin-1-ylmethyl-phenyl)-2H-[1,2,4a triazol-3-yl]-phenol hydrochloride salt 1:1 (mixture of tautomers)

The title compound, MS: m/e=321.3 (M+H⁺) was obtained as a light brown foam by reaction of 5-(2-methoxy-phenyl)-3-(3-pyrrolidin-1-ylmethyl-phenyl)-1H-[1,2,4]triazole hydrochloride (1:1) with borontribromide, followed by preparation of the hydrochloride salt.

EXAMPLE 77

5-(4-Methanesulfonyl-phenyl)-3-(3-pyrrolidin-1-ylmethyl-phenyl)-1H-[1,2,4]triazole trifluoroacetate (1:1) (mixture of tautomers)

A solution of 5-(4-methylsulfanyl-phenyl)-3-(3-pyrrolidin-1-ylmethyl-phenyl)-1H-[1,2,4]triazole (75 mg, 0.2 mmol) in methanol (10 ml) was treated with potassium monopersulfate triple salt (Oxone™) (394 mg, 0.64 mmol) at 20° C. for 48 hrs., then for 18 hrs. under reflux. Upon cooling the product mixture was filterd, the solvent was evaporated and the residue was subjected to preparative reversed phase-HPLC purification using a YMC ODS-AQ column (20×50 mm) and a (0.1% trifluoroacetic acid) water-acetonitrile gradient (25 ml/min.). The pure fractions were pooled and concentrated, the solvent was evaporated and the product was dried under high vacuum to afford the title compound (131 mg, 37% yield) as a white foam. MS: m/e=461.1 (M+H⁺).

EXAMPLE 78

5-(4-Methylsulfanyl-phenyl)-3-(3-pyrrolidin-1-ylmethyl-phenyl)-1H-[1,2,4]triazole hydrochloride salt (1:1) (mixture of tautomers)

To a stirred ethanolic suspension of 3-pyrrolidin-1-ylmethyl-benzamidine hydrochloride salt (1:2) (414 mg, 1.5 mmol, 1.5 eq.) in 15 ml ethanol was added over 3 minutes 1.2N NaOEt in ethanol (3.4 ml, 4 eq.) and stirring was continued for 30 min. at r.t. 4-Methylsulfanyl-benzoic acid hydrazide (182 mg, 1 mmol) in ethanol at 20° C. was then added and the mixture heated to reflux for 50 hrs. Upon cooling the product mixture was filtered, solvent evaporated and residue chromatographed over 20 g SiO₂ (Merck 230–400 mesh) with CH₂Cl₂-MeOH (2M NH₃) 96:4, affording a foam after solvent evaporation. This material was dissolved in ethanol at r.t. and an excess 2N HCl/ether solution (1.0 ml, 2 mmol) was added. After 30 min. the solvent was evaporated and the residue was dried overnight under high vacuum at 30° C. affording the title compound (200 mg, 52% yield) as a yellow foam. MS: m/e=351.5 (M+H⁺).

EXAMPLE 79

2-Methoxy-5-[5-(3-pyrrolidin-1-ylmethyl-phenyl)-2H-[1,2,4]triazol-3-yl]-phenol hydrochloride (1:1) (mixture of tautomers)

A solution of 5-(3-benzyloxy-4-methoxy-phenyl)-3-(3-pyrrolidin-1-ylmethyl-phenyl)-1H-[1,2,4]triazole hydrochloride (1:1) (300 mg, 0.63 mmol) in ethanol (80 ml) was hydrogenated (1 atm H₂) with Pd/C (10%, 50 mg) at 20° C. overnight. The catalyst was filtered off, the solvent volume was reduced to ca. 5 ml and the resulting product recrystallized. After drying under high vaccum at 40° C. for 8 hrs. the title compound was obtained (152 mg, 63% yield) as a light yellow solid. MS: m/e=351.4 (M+H⁺).

EXAMPLE 80

5-(3-Benzyloxy-4-methoxy-phenyl)-3-(3-pyrrolidin-1-ylmethyl-phenyl)-1H-[1,2,4]triazole hydrochloride (1:1) (mixture of tautomers)

To a stirred ethanolic suspension of 3-pyrrolidin-1-ylmethyl-benzamidine hydrochloride salt (1:2) (414 mg, 1.5 mmol, 1.5 eq.) in ethanol (15 ml) was added 1.2N NaOEt in ethanol (3.4 ml, 4 eq.) over 3 min. and stirring was then continued for 30 min. at r.t. 3-Benzyloxy-4-methoxy-benzoic acid hydrazide (272 mg, 1 mmol) in ethanol was added at 20° C. and the resulting mixture was heated to reflux for 50 hrs. Upon cooling, the product mixture was filtered, the solvent was evaporated and the residue chromatographed over 20 g SiO₂ (Merck 230–400 mesh) with CH₂Cl₂-MeOH (2M NH₃) 96:4 affording a solid. This material was dissolved in ethanol at r.t. and an excess 2N HCl/ether solution (1.0 ml, 2 mmol) was added. After 30 min. the solvent was evaporated and the residue dried under high vacuum at 30° C. overnight affording the title compound (326 mg, 89% yield) as a yellow solid. MS: m/e= 441.6 (M+H⁺)

EXAMPLE 81

(RS)-Acetic acid 1-{3-[5-(4-methoxy-phenyl)-1H-[1,2,4]triazol-3-yl]-benzyl}-pyrrolidin-3-yl ester hydrochloride salt 1:1 (mixture of tautomers)

A solution of (RS)-1-{3-[5-(4-methoxy-phenyl)-1H-[1,2,4]triazol-3-yl]-benzyl}-pyrrolidin-3-ol hydrochloride (1:1) (mixture of tautomers) (50 mg, 0.13 mmol) in CH₂Cl₂ (5 ml) was treated with triethylamine (26 mg, 0.26 mmol 2 eq.) and stirred for 30 min. at r.t. Acetyl chloride (11 mg, 0.13 mmol, 1 eq.) was added and stirring was continued for 1.5 hrs. After removal of the solvent the residue was chromatographed over 20 g SiO₂ (Merck 230–400 mesh) with CH₂Cl₂-MeOH (2M NH₃) 96:4. The resulting product was dissolved in ethanol at r.t. and an excess 1.45 N HCl/EtOH solution (0.1 ml, 0.14 mmol) was added. After 30 min. stirring the solvent was evaporated and the residue dried under high vacuum at 40° C. overnight affording the title compound (53 mg, 0.12 mmol, 96% yield) as a colorless solid. MS: m/e=393.2 (M+H⁺)

EXAMPLE 82

3-[2-(3,4-Dichloro-phenyl)-3H-imidazol-4-yl]-benzylamine hydrochloride1:1 (mixture of tautomers)

A solution of 3-[2-(3,4-dichloro-phenyl)-3H-imidazol-4-yl]-benzonitrile (4.1 g, 13 mmol), in THF (130 ml) was slowly added to an ice-cooled mixture of lithium aluminum hydride (0.99 g, 26 mmol) in THF (130 ml). The mixture was stirred for 30 min. at r.t., then saturated Seignette-salt solution (5 ml) was added slowly and stirring was continued for 30 min. The precipitate was filtered and the organic phase evaporated and chromatographed over SiO₂ with CH₂Cl₂—CH₃OH—NH₄OH (140:10:1) to obtain 3-[2-(3,4-dichloro-phenyl)-3H-imidazol-4-yl]-benzylamine (1.77 g, 43%) as a foam. The hydrochloride salt was then prepared which was crystallized to an off-white solid. Mp. >250° C. (MeOH/Et₂O), MS: m/e=318 (M+H⁺).

EXAMPLE 83

{3-[2-(3,4-Dichloro-phenyl)-3H-imidazol-4-yl]-benzyl}-methyl-amine hydrochloride1:1 (mixture of tautomers)

A solution of 3-[2-(3,4-dichloro-phenyl)-3H-imidazol-4-yl]-benzylamine (1.59 g, 5.0 mmol) and triethylamine (1.01 g, 10.0 mmol) in THF (32 ml) was cooled in an ice bath and treated with a solution of ethyl chloroformate (1.08 g, 10 mmol) in THF (10 ml). The resulting mixture was stirred at r.t. for 1 hr., filtered, treated with 1.14 g (30 mmol) lithium aluminum hydride and refluxed for 2 hrs. Then saturated Seignette-salt solution (6 ml) was added slowly and stirring was continued for 30 min. The precipitate was filtered and the organic phase evaporated and chromatographed over SiO₂ with CH₂Cl₂—CH₃OH—NH₄OH (200:10:1) to obtain {3-[2-(3,4-dichloro-phenyl)-3H-imidazol-4-yl]-benzyl}-methyl-amine (0.91 g, 55%) as an oil which after HCl/

MeOH addition was crystallized as a light yellow hydrochloride salt. Mp. 145° C. (dec.) (MeOH/Ipr$_2$O), MS: m/e=332 (M+H$^+$).

Following the Method of Example 83 the Compounds of Examples 84–90 were Prepared

EXAMPLE 84

{3-[2-(3,4-Dichloro-phenyl)-3H-imidazol-4-yl]-benzyl}-dimethyl-amine hydrochloride1:1 (mixture of tautomers)

The title compound, Mp. >250° C. (MeOH/Et$_2$O), MS: m/e=346 (M+H$^+$) was obtained as a colorless crystalline material by reaction of {3-[2-(3,4-dichloro-phenyl)-3H-imidazol-4-yl]-benzyl}-methyl-amine with triethylamine and ethyl chloroformate followed by reaction with lithium aluminum hydride and finally addition of HCl/MeOH followed by crystallization of the hydrochloride salt.

EXAMPLE 85

2-({3-[2-(3,4-Dichloro-phenyl)-3H-imidazol-4-yl]-benzyl}-methyl-amino)-ethanol hydrochloride1:1 (mixture of tautomers)

The title compound, Mp. >260° C. (MeOH/Et$_2$O), MS: m/e=376 (M+H$^+$) was obtained as a colorless crystalline material by reaction of {3-[2-(3,4-dichloro-phenyl)-3H-imidazol-4-yl]-benzyl}-methyl-amine with triethylamine and methyl oxalylchloride followed by reaction with lithium aluminum hydride and finally addition of HCl/MeOH followed by crystallization of the hydrochloride salt.

EXAMPLE 86

{3-[2-(3,4-Dichloro-phenyl)-3H-imidazol-4-yl]-benzyll-ethyl-amine hydrochloride1:1 (mixture of tautomers)

The title compound, Mp. 244–245° C. (MeOH/Et$_2$O), MS: m/e=346 (M+H$^+$) was obtained as a colorless crystalline material by reaction of 3-[2-(3,4-dichloro-phenyl)-3H-imidazol-4-yl]-benzylamine with triethylamine and acetyl chloride followed by reaction with lithium aluminum hydride and finally addition of HCl/MeOH followed by crystallization of the hydrochloride salt.

EXAMPLE 87

{3-[2-(3,4-Dichloro-phenyl)-3H-imidazol-4-yl]-benzyl}-ethyl-methyl-amine hydrochloride1:1 (mixture of tautomers)

The title compound, Mp. 197–199° C. (MeOH/Et$_2$O), MS: m/e=359 (M$^+$) was obtained as a colorless crystalline material by reaction of {3-[2-(3,4-dichloro-phenyl)-3H-imidazol-4-yl]-benzyl}-ethyl-amine with triethylamine and ethyl chloroformate followed by reaction with lithium aluminum hydride and finally addition of HCl/MeOH followed by crystallization of the hydrochloride salt.

EXAMPLE 88

{3-[2-(3,4-Dichloro-phenyl)-3H-imidazol-4-yl]-benzyl}-diethyl-amine hydrochloride1:1 (mixture of tautomers)

The title compound, Mp. 198–199° C. (MeOH/Et$_2$O), MS: m/e=373 (M$^+$) was obtained as a colorless crystalline material by reaction of {3-[2-(3,4-dichloro-phenyl)-3H-imidazol-4-yl]-benzyl}-ethyl-amine with triethylamine and acetyl chloride followed by reaction with lithium aluminum hydride and finally addition of HCl/MeOH followed by crystallization of the hydrochloride salt.

EXAMPLE 89

4-{3-[2-(3,4-Dichloro-phenyl)-3H-imidazol-4-yl]-benzylamino}-butan-1-ol hydrochloride1:1 (mixture of tautomers)

The title compound, Mp. 70° C. (dec.) (MeOH/Et$_2$O), MS: m/e=390 (M+H$^+$) was obtained as a colorless crystalline material by reaction of 3-[2-(3,4-dichloro-phenyl)-3H-imidazol-4-yl]-benzylamine with triethylamine and 3-carbomethoxypropionylchloride followed by reaction with lithium aluminum hydride and finally addition of HCl/MeOH followed by crystallization of the hydrochloride salt.

EXAMPLE 90

2-(3,4-Dichloro-phenyl)-5-(3-pyrrolidin-1-ylmethyl-phenyl)-1H-imidazole hydrochloride1:1 (mixture of tautomers)

The title compound, Mp. >250° C. (MeOH/Et$_2$O), MS: m/e=372 (M+H$^+$) was obtained as a colorless crystalline material by reaction of 3-[2-(3,4-dichloro-phenyl)-3H-imidazol-4-yl]-benzylamine with triethylamine and 3-carbomethoxypropionylchloride followed by reaction with lithium aluminum hydride and finally addition of HCl/MeOH followed by crystallization of the hydrochloride salt.

EXAMPLE 91

N-{3-[2-(3,4-Dichloro-phenyl)-3H-imidazol-4-yl]-benzyl}-2-hydroxy-acetamide (mixture of tautomers)

A solution of 3-[2-(3,4-dichloro-phenyl)-3H-imidazol-4-yl]-benzylamine (1.32 g, 4.1 mmol) and triethylamine (0.51 g, 5.0 mmol) in THF (41 ml) was cooled in an ice bath and treated with a solution of ethyl oxalyl chloride (0.68 g, 5 mmol) in THF (5 ml). The resulting mixture was stirred at r.t. for 1 hr, filtered, treated with 0.31 g (8.2 mmol) lithium aluminum hydride and refluxed for 30 min. Then saturated Seignette-salt solution (3 ml) was added slowly and stirring was continued for 30 min. The precipitate was filtered and the organic phase evaporated and chromatographed over SiO$_2$ with CH$_2$Cl$_2$—CH$_3$OH—NH$_4$OH (200:10:1) to obtain N-{3-[2-(3,4-dichloro-phenyl)-3H-imidazol-4-yl]-benzyl}-2-hydroxy-acetamide (0.91 g, 59%) which was crystallised from EtOAc. Mp. 124–125° C. (dec.) (EtOAc), MS: m/e=376 (M+H$^+$).

Following the Method of Example 82 the Compound of Example 92 was Prepared

EXAMPLE 92

3-[4-(4-Methoxy-phenyl)-1H-imidazol-2-yl]-benzylamine hydrochloride1:1 (mixture of tautomers)

The title compound, Mp. 249–250° C. (dec.) (MeOH/Et$_2$O), MS: m/e=280 (M+H$^+$) was obtained as a colorless crystalline material by reaction of 3-[4-(4-methoxy-phenyl)-1H-imidazol-2-yl]-benzonitrile with lithium aluminum hydride and finally addition of HCl/MeOH followed by crystallization of the hydrochloride salt.

Following the Method of Example 163 and 82 the Compound of Example 93 was Prepared

EXAMPLE 93

3-(4-p-Tolyl-1H-imidazol-2-yl)-benzylamine hydrochloride1:1 (mixture of tautomers)

The title compound, Mp. >250° C. (MeOH/Et$_2$O), MS: m/e=263 (M$^+$) was obtained as a colorless crystalline material by reaction of 3-(4-Niodo-1H-imidazol-2-yl)-benzonitrile with 4-tolyl boronic acid in the presence of palladium tetrakis(triphenylphosphine) and 2M K$_2$CO$_3$ solution followed by treatment with lithium aluminum hydride and finally addition of HCl/MeOH followed by crystallization of the hydrochloride salt.

Following the Method of Example 82 the Compounds of Examples 94 and 95 were Prepared

EXAMPLE 94

3-[5-(3,4-Dichloro-phenyl)-1H-imidazol-2-yl]-benzylamine hydrochloride1:1 (mixture of tautomers)

The title compound, Mp. >250° C. (MeOH/Et$_2$O), MS: m/e=318 (M+H$^+$) was obtained as a colorless crystalline material by reaction of 3-[5-(3,4-dichloro-phenyl)-1H-imidazol-2-yl]-benzonitrile with lithium aluminum hydride and finally addition of HCl/MeOH followed by crystallization of the hydrochloride salt.

EXAMPLE 95

3-(4-NNaphthalen-2-yl-1H-imidazol-2-yl)-benzylamine (mixture of tautomers)

The title compound, Mp. 216–217° C. (CH$_2$Cl$_2$/MeOH), MS: m/e =300 (M+H$^+$) was obtained as a colorless crystalline material by reaction of 3-(4-naphthalen-2-yl-1H-imidazol-2-yl)-benzonitrile with lithium aluminum hydride.

EXAMPLE 96

{3-[5-(4-Methoxy-phenyl)-2-methyl-2H-[1,2,4]triazol-3-yl]-benzyl}-dimethyl-amine hydrochloride (1:1)

A solution of 3-[5-(4-methoxy-phenyl)-2-methyl-2H-[1,2,4]triazol-3-yl]-benzaldehyde (130 µg, 0.44 mmol), dimethylamine in EtOH (96 µl, 5.6 N, 0.53 mmol) and acetic acid (30 µl, 0.53 mmol) in THF (5 ml) was stirred for 15 min at r.t then sodium triacetoxyborohydride (141 mg, 0.66 mmol) was added in a single portion. This mixture was allowed to react at r.t. under argon until all the aldehyde had been consumed (ca. 1.5 hr). Saturated aqueous Na$_2$CO$_3$ solution was then added, stirred for 15 min and extracted twice with EtOAc (20 ml). The combined organic phase was dried with Na$_2$SO$_4$ filtered and the solvent evaporated under reduced pressure. The resulting pale yellow oil was dissolved in ethanol then HCl in ethanol (1.45N) 0.34 ml was added and stirred for 60 min, the resulting salt was precipitated with ether at 4° C. to afford a white amorphous solid (130 mg, 0.36 mmol, 81.7%), MS: m/e=323.4 (M+H$^+$).
Following the Method of Example 96 the Compounds of Example 97 to 112 were Prepared

EXAMPLE 97

{5-[3-(4-Methoxy-phenyl)-2-methyl-2H-[1,2,4]triazol-3-yl]-benzyl}-dimethyl-amine hydrochloride (1:1)

Using 3-[5-(4-methoxy-phenyl)-1-methyl-1H-[1,2,4]triazol-3-yl]-benzaldehyde and dimethylamine the title compound was prepared as a white amorphous solid (65% yield), MS: m/e=323.4 (M+H$^+$).

EXAMPLE 98

3-(4-Methoxy-phenyl)-1-methyl-5-(3-pyrrolidin-1-ylmethyl-phenyl)-1H-[1,2,4]triazole hydrochloride (1:1)

Using 3-[5-(4-methoxy-phenyl)-2-methyl-2H-[1,2,4]triazol-3-yl]-benzaldehyde pyrrolidine the title compound was prepared as an amorphous white foam (100% yield) after evaporation of all solvents under reduced pressure followed by drying under high vacuum (0.05 mmHg) at 50° C. for 3 hr, MS: m/e=349.5 (M+H$^+$).

EXAMPLE 99

5-(4-Methoxy-phenyl)-1-methyl-3-(3-pyrrolidin-1-ylmethyl-phenyl)-1H-[1,2,4]triazole hydrochloride (1:1)

Using 3-[5-(4-methoxy-phenyl)-1-methyl-1H-[1,2,4]triazol-3-yl]-benzaldehyde and pyrrolidine the title compound was prepared as an amorphous white solid (99% yield), MS: m/e=349.5 (M+H$^+$).

EXAMPLE 100

5-[3-(2,5-Dihydro-pyrrol-1-ylmethyl)-phenyl]-3-(4-methoxy-phenyl)-1-methyl-1H-[1,2,4]triazole hydrochloride (1:1)

Using dihydropyrrolidine (70%, containing 30% pyrrolidine) the title compound was afforded as a crude product which was chromatographed over SiO$_2$ (Merck 230–400 mesh) using CH$_2$Cl$_2$/(2M NH$_3$ in MeOH) 97:3, before salt preparation. The pure titled compound was obtained as an amorphous white solid (46% yield), MS: m/e=347.3 (M+H$^+$).

EXAMPLE 101

1-Ethyl-3-(4-methoxy-phenyl)-5-(3-pyrrolidin-1-ylmethyl-phenyl)-1H-[1,2,4]triazole hydrochloride (1:1)

Using 3-[2-ethyl-5-(4-methoxy-phenyl)-2H-[1,2,4]triazol-3-yl]-benzaldehyde and pyrrolidine the title compound was prepared as a pale yellow oil (92% yield) after evaporation of all solvents under reduced pressure followed by drying under high vacuum (0.05 mmHg) at 50° C. for 3 hr. MS: m/e=363.3 (M+H$^+$).

EXAMPLE 102

1-Ethyl-5-(4-methoxy-phenyl)-3-(3-pyrrolidin-1-ylmethyl-phenyl)-1H-[1,2,4]triazole hydrochloride (1:1)

Using 3-[1-ethyl-5-(4-methoxy-phenyl)-1H-[1,2,4]triazol-3-yl]-benzaldehyde and pyrrolidine the title compound was prepared as a pale orange foam (87.3% yield) after evaporation of all solvents under reduced pressure followed by drying under high vacuum (0.05 mmHg) at 50° C. for 3 hr. MS: m/e=363.3 (M+H$^+$).

EXAMPLE 103

{3-[2-Ethoxymethyl-5-(4-methoxy-phenyl)-2H-[1,2,4]triazol-3-yl]-benzyl}-dimethyl-amine hydrochloride (1:1)

Using 3-[2-ethoxymethyl-5-(4-methoxy-phenyl)-2H-[1,2,4]triazol-3-yl]-benzaldehyde and dimethylamine the title compound was prepared as a white amorphous solid (73.8% yield), MS: m/e=367.2 (M+H$^+$).

EXAMPLE 104

{3-[2-Methoxymethyl-5-(4-methoxy-phenyl)-2H-[1,2,4]triazol-3-yl]-benzyl}-dimethyl-amine hydrochloride (1:1)

Using 3-[2-methoxymethyl-5-(4-methoxy-phenyl)-2H-[1,2,4]triazol-3-yl]-benzaldehyde and dimethylamine the title compound was prepared as a white amorphous solid (73.7% yield), MS: m/e=353.2 (M+H$^+$).

EXAMPLE 105

2-[5-(3-Dimethylaminomethyl-phenyl)-3-(4-methoxy-phenyl)-[1,2,4]triazol-1-yl]-ethanol hydrochloride (1:1)

Using 3-[2-(2-hydroxy-ethyl)-5-(4-methoxy-phenyl)-2H-[1,2,4]triazol-3-yl]-benzaldehyde and dimethylamine the title compound was prepared as a white amorphous solid (86.4% yield), MS: m/e=353.197 (M+H$^+$).

EXAMPLE 106

{3-[2-Difluoromethyl-5-(4-methoxy-phenyl)-2H-[1,2,4]triazol-3-yl]-benzyl}-dimethyl-amine; hydrochloride salt (1:1)

Using 3-[2-difluoromethyl-5-(4-methoxy-phenyl)-2H-[1,2,4]triazol-3-yl]-benzaldehyde and dimethylamine the title compound was prepared as a white amorphous solid (83.4% yield), MS: m/e=359.168 (M+H$^+$).

EXAMPLE 107

2-[3-(3-Dimethylaminomethyl-phenyl)-5-(4-methoxy-phenyl)-[1,2,4]triazol-1-yl]-ethanol hydrochloride (1:1)

Using 3-[1-(2-hydroxy-ethyl)-5-(4-methoxy-phenyl)-1H-[1,2,4]triazol-3-yl]-benzaldehyde and dimethylamine the title compound was prepared as a white foam (100% yield) after evaporation of all solvents under reduced pressure followed by drying under high vacuum (0.05 mmHg) at 50° C. for 2 h, MS: m/e=353.3 (M+H$^+$).

EXAMPLE 108

{3[-5-(4-Difluoromethoxy-phenyl)-2-methyl-2H-[1,2,4] triazol-3-yl]-benzyl}-dimethyl-amine hydrochloride salt (1:1)

Using 3-[5-(4-difluoromethoxy-phenyl)-2-methyl-2H-[1,2,4]triazol-3-yl]-benzaldehyde and dimethylamine the title compound was prepared as a pale brown amorphous solid (88.9% yield), MS: m/e=359.168 (M+H$^+$).

EXAMPLE 109

Dimethyl-[3-(2-methyl-5-p-tolyl-2H-[1,2,4]triazol-3-yl)-benzyl]-amine hydrochloride salt (1:1)

Using 3-(2-methyl-5-p-tolyl-2H-[1,2,4]triazol-3-yl)-benzaldehyde and dimethylamine the title compound was afforded as a crude product which was chromatographed over SiO$_2$ (Merck 230–400 mesh) using CH$_2$Cl$_2$/(2M NH$_3$ in MeOH) 95:5, before salt preparation. The pure titled compound was obtained as an amorphous white foam (51.2% yield), MS: m/e=307.1923 (M+H$^+$).

EXAMPLE 110

2-[5-(3,4-Dichloro-phenyl)-3-(3-dimethylaminomethyl-phenyl)-[1,2,4]triazol-1-yl]-ethanol hydrochloride (1:1)

Using 3-[5-(3,4-dichloro-phenyl)-1-(2-hydroxy-ethyl)-1H-[1,2,4]triazol-3-yl]-benzaldehyde and dimethylamine the title compound was prepared as a pale yellow amorphous foam (98.4% yield) after evaporation of all solvents under reduced pressure followed by drying under high vacuum (0.05 mmHg) at 50° C. for 2 h, MS: m/e=391.2 (M+H$^+$).

EXAMPLE 111

2-[3-(3,4-Dichloro-phenyl)-5-(3-dimethylaminomethyl-phenyl)-[1,2,4]triazol-1-yl]-ethanol hydrochloride (1:1)

Using 3-[5-(3,4-dichloro-phenyl)-2-(2-hydroxy-ethyl)-2H-[1,2,4]triazol-3-yl]-benzaldehyde and dimethylamine the title compound was afforded as a crude product which was chromatographed over SiO$_2$ (Merck 230–400 mesh) using CH$_2$Cl$_2$/(2M NH$_3$ in MeOH) 95:5, before salt preparation. The pure titled compound was obtained as a off-white amorphous foam (67.7% yield) after evaporation of all solvents under reduced pressure followed by drying under high vacuum (0.05 mmHg) at 50° C. for 2 h, MS: m/e=391.2 (M+H$^+$).

EXAMPLE 112

{3-[5-(3-Fluoro-4-methoxy-phenyl)-2-methyl-2H-[1,2,4] triazol-3-yl]-benzyl}-dimethyl-amine hzdrochloride (1:1)

Using 3-[5-(3-fluoro-4-methoxy-phenyl)-2-methyl-2H-[1,2,4]triazol-3-yl]-benzaldehyde and dimethylamine the title compound was prepared as a pale light brown solid (76.4% yield) after evaporation of all solvents under reduced pressure followed by drying under high vacuum (0.05 mmHg) at 50° C. for 2 h, MS: m/e=341.3 (M+H$^+$).

EXAMPLE 113

1-[5-(3-Dimethylaminomethyl-phenyl)-3-(4-methoxy-phenyl)-[1,2,4]triazol-1-yl]-propan-2-ol hydrochloride salt (1:1)

To a stirred solution of 1-[5-(3-dimethylaminomethyl-phenyl)-3-(4-methoxy-phenyl)-[1,2,4]triazol-1-yl]-propan-2-one hydrochloride (22 mg, 0.05 mmol) in methanol (4 ml), was added Lithium borohydride (1.8 mg, 0.08 mmol) and the mixture stirred for 4 hr at r.t. Saturated Na$_2$CO$_3$ solution was then added and the mixture stirred for 15 min., the aqueous phase was then extracted twice with EtOAc, dried with Na$_2$SO$_4$ filtered and the solvent evaporated to afford a yellow oil. This was dissolved in CHCl$_3$ and 1.45N HCl/EtOH (0.05 ml) was added at 4° C. After 20 min ether was added to precipitate the titled salt as a light brown solid (17 mg, 76.9% yield) MS: m/e=367.3 (M+H$^+$).

EXAMPLE 114

1-[5-(3-Dimethylaminomethyl-phenyl)-3-(4-methoxy-phenyl)-[1,2,4]triazol-1-yl]-propan-2-one hydrochloride salt (1:1)

Using 3-[5-(4-methoxy-phenyl)-2-(2-oxo-propyl)-2H-[1,2,4]triazol-3-yl]-benzaldehyde and dimethylamine the title compound was obtained, quantitatively as a yellow amorphous solid after evaporation of all solvents under reduced pressure followed by drying under high vacuum (0.05 mmHg) at 50° C. for 2 h, MS: m/e=365.3 (M+H$^+$).

EXAMPLE 115

1-Allyl-3-(4-methoxy-phenyl)-5-(3-pyrrolidin-1-ylmethyl-phenyl)-1H-[1,2,4]triazole hydrochloride (1:1)

A solution of mixture of 3-[2-allyl-5-(4-methoxy-phenyl)-2H-[1,2,4]triazol-3-yl]-benzaldehyde and 3-[1-allyl-5-(4-methoxy-phenyl)-1H-[1,2,4]triazol-3-yl]-benzaldehyde (1:1) (60 mg, 0.19 mmol), pyrrolidine (19 µl, 5 0.23 mmol) and acetic acid (13 µl, 0.023 mmol) in THF (5 ml) was stirred for 15 min at r.t then sodium triacetoxyborohydride (59 mg, 0.28 mmol) was added in a single portion. This mixture was allowed to react at r.t. under argon until all the aldehyde had been consumed (ca. 1.5 hr). Saturated aqueous Na$_2$CO$_3$ solution was then added, stirred for 15 min and extracted twice with EtOAc (20 ml). The combined organic phase was dried with Na$_2$SO$_4$ filtered and the solvent evaporated under reduced pressure. The resulting isomeric mixture, obtained as an oil, was chromatographed over SiO$_2$ (Merck 230–400 mesh) using CH$_2$Cl$_2$/(2M NH$_3$ in MeOH) 97:3, to provide the separate regioisomers. The isolated regioisomer was taken up in ethanol and was directly converted to its hydrochloride salt with 1.45N HCl/EtOH at 4° C. Following solvent evaporation the resulting white foam was dried under high vacuum (0.05 mmHg) at 50° C. for 3 h to afford the title compound (25 mg, 0.06 mmol, 32.4%), MS: m/e=375.4 (M+H$^+$). The regiochemistry of alkylation was established by $^1$H-NMR, nOe spectroscopy.

EXAMPLE 116

1-Allyl-5-(4-methoxy-phenyl)-3-(3-pyrrolidin-1-ylmethyl-phenyl)-1H-[1,2,4]triazole hydrochloride (1:1)

A solution of mixture of 3-[2-allyl-5-(4-methoxy-phenyl)-2H-[1,2,4]triazol-3-yl]-benzaldehyde and 3-[-allyl-5-(4-methoxy-phenyl)-1H-[1,2,4]triazol-3-yl]-benzaldehyde (1:1) (60 mg, 0.19 mmol), pyrrolidine (19 µl, 5 0.23 mmol) and acetic acid (13 µl, 0.023 mmol) in THF (5 ml) was stirred for 15 min at r.t then sodium triacetoxyborohydride (59 mg, 0.28 mmol) was added in a single portion. This mixture was allowed to react at r.t. under argon until all the aldehyde had been consumed (ca. 1.5 hr). Saturated aqueous Na$_2$CO$_3$ solution was then added, stirred for 15 min and extracted twice with EtOAc (20 ml). The combined organic phase was dried with Na$_2$SO$_4$ filtered and the solvent evaporated under reduced pressure. The resulting isomeric mixture, obtained as an oil, was chromatographed over SiO$_2$ (Merck 230–400 mesh) using CH$_2$Cl$_2$/(2M NH$_3$ in MeOH) 97:3, to provide the separate regioisomers. The isolated regioisomer was taken up in ethanol and was directly converted to its hydrochloride salt with 1.45N HCl/EtOH at 4° C. Following solvent evaporation the resulting pale yellow foam was dried under high vacuum (0.05 mmHg) at 50° C. for 3 h to afford the title compound (30 mg, 0.07 mmol, 38.8%), MS: m/e=375.5 (M+H$^+$). The regiochemistry of alkylation was established by $^1$H-NMR, nOe spectroscopy.

EXAMPLE 117
1-Benzyl-3-(4-methoxy-phenyl)-5-(3-pyrrolidin-1-ylmethyl-phenyl)-1H-[1,2,4]triazole hydrochloride (1:1) and 1-benzyl-5-(4-methoxy-phenyl)-3-(3-pyrrolidin-1-ylmethyl-phenyl)-1H-[1,2,4]triazole hydrochloride (1:1)

A solution of a mixture of 3-[1-benzyl-5-(4-methoxy-phenyl)-1H-[1,2,4]triazol-3-yl]-benzaldehyde and 3-[2-benzyl-5-(4-methoxy-phenyl)-2H-[1,2,4]triazol-3-yl]-benzaldehyde (1:1) (80 mg, 0.22 mmol), pyrrolidine (21 µl, 0.26 mmol) and acetic acid (15 µl, 0.026 mmol) in THF (5 ml) was stirred for 15 min at r.t then sodium triacetoxyborohydride (69 mg, 0.32 mmol) was added in a single portion. This mixture was allowed to react at r.t. under argon until all the aldehyde had been consumed (ca. 3 hr). Saturated aqueous $Na_2CO_3$ solution was then added, stirred for 15 min and extracted twice with EtOAc (20 ml). The combined organic phase was dried with $Na_2SO_4$ filtered and the solvent evaporated under reduced pressure. The resulting mixture, obtained as an oil, was chromatographed over $SiO_2$ (Merck 230–400 mesh) using $CH_2Cl_2/(2M\ NH_3$ in MeOH) 97:3, to provide an approximately 1:1 mixture of the N1 and N2 regioisomers as determined by C18-reversed-phase HPLC (MeCN/$H_2O$+0.1% TFA) and $^1$H-NMR spectroscopy. The resulting isomeric product mixture was dissolved in ethanol then 1.45N HCl/ethanol (1.1 eq.) was added and the mixture stirred for 30 min at 4° C. The resulting salt was evaporated to dryness and further dried under high vacuum (0.05 mmHg) at 50° C. for 3 h, affording a white foam (63 mg, 0.14 mmol, 63%), MS: m/e=425.5 (M+H$^+$).
Following the Method of Example 117 the Compounds of Example 118 to 141 were Prepared

EXAMPLE 118
3-(4-Methoxy-phenyl)-1-methyl-5-(3-pyrrolidin-1-ylmethyl-phenyl)-1H-[1,2,4]triazole hydrochloride and 5-(4-methoxy-phenyl)-1-methyl-3-(3-pyrrolidin-1-ylmethyl-phenyl)-1H-[1,2,4]triazole hydrochloride (ca. 1:1)

Using a 1:1 mixture of 3-[5-(4-methoxy-phenyl)-2-methyl-2H-[1,2,4]triazol-3-yl]-benzaldehyde and 3-[5-(4-methoxy-phenyl)-1-methyl-1H-[1,2,4]triazol-3-yl]-benzaldehyde and pyrrolidine the title compound was obtained as a light yellow oil (67.7% yield), MS: m/e=349.4 (M+H$^+$).

EXAMPLE 119
3-(4-Methoxy-phenyl)-1-phenethyl-5-(3-pyrrolidin-1-ylmethyl-phenyl)-1H-[1,2,4]triazole hydrochloride and 5-(4-methoxy-phenyl)-1-phenethyl-3-(3-pyrrolidin-1-ylmethyl-phenyl)-1H-[1,2,4]triazole hydrochloride (ca. 1:1)

Using a mixture of 3-[5-(4-methoxy-phenyl)-2-phenethyl-2H-[1,2,4]triazol-3-yl]-benzaldehyde and 3-[5-(4-methoxy-phenyl)-1-phenethyl-1H-[1,2,4]triazol-3-yl]-benzaldehyde (ca. 1:1) and pyrrolidine the title compound was obtained as an amorphous orange foam (88.8% yield), MS: m/e=439.4 (M+H$^+$).

EXAMPLE 120
Mixture of [5-(3-Dimethylaminomethyl-phenyl)-3-(4-methoxy-phenyl)-[1,2,4]triazol-1-yl]-acetic acid ethyl ester hydrochloride and [3-(3-dimethylaminomethyl-phenyl)-5-(4-methoxy-phenyl)-[1,2,4]triazol-1-yl]-acetic acid ethyl ester hydrochloride (1:1)

Using a mixture of [3-(3-formyl-phenyl)-5-(4-methoxy-phenyl)-[1,2,4]triazol-1-yl]-acetic acid ethyl ester and [5-(3-formyl-phenyl)-3-(4-methoxy-phenyl)-[1,2,4]triazol-1-yl]-acetic acid ethyl ester (1:1) and 5.6N dimethylamine in EtOH the title compound was obtained as an amorphous yellow foam (91.7% yield), MS: m/e=394.2 (M+H$^+$).

EXAMPLE 121
{3-[5-(4-Methoxy-phenyl)-2-prop-2-ynyl-2H-[1,2,4]triazol-3-yl]-benzyl}-dimethyl-amine hydrochloride and {3-[5-(4-methoxy-phenyl)-1-prop-2-ynyl-1H-[1,2,4]triazol-3-yl]-benzyl}-dimethyl-amine hydrochloride (ca. 1:1)

Using 3-[5-(4-methoxy-phenyl)-2-prop-2-ynyl-2H-[1,2,4]triazol-3-yl]-benzaldehyde and 3-[5-(4-methoxy-phenyl)-1-prop-2-ynyl-1H-[1,2,4]triazol-3-yl]-benzaldehyde (ca. 1:1) and 5.6N dimethylamine in EtOH the title compound was obtained as an amorphous light yellow foam (77.3% yield), MS: m/e=347.4 (M+H$^+$).

EXAMPLE 122
{3-[5-(4-Methoxy-phenyl)-2-(2-methyl-allyl)-2H-[1,2,4]triazol-3-yl]-benzyl}-dimethyl-amine hydrochloride and {3-[5-(4-methoxy-phenyl)-1-(2-methyl-allyl)-1H-[1,2,4]triazol-3-yl]-benzyl}-dimethyl-amine hydrochloride (ca. 1:1)

Using 3-[5-(4-methoxy-phenyl)-1-(2-methyl-allyl)-1H-[1,2,4]triazol-3-yl]-benzaldehyde and 3-[5-(4-methoxy-phenyl)-2-(2-methyl-allyl)-2H-[1,2,4]triazol-3-benzaldehyde (ca. 1:1) and 5.6N dimethylamine in EtOH the title compound was obtained as an amorphous light yellow foam (100% yield), MS: m/e=363.4 (M+H$^+$).

EXAMPLE 123
{3-[2-Cyclopropylmethyl-5-(4-methoxy-phenyl)-2H-[1,2,4]triazol-3-yl]-benzyl}-dimethyl-amine hydrochloride and {3-[1-cyclopropylmethyl-5-(4-methoxy-phenyl)-1H-[1 1,2,4]triazol-3-yl]-benzyl}-dimethyl-amine hydrochloride (ca. 1:1)

Using 3-[2-cyclopropylmethyl-5-(4-methoxy-phenyl)-2H-[1,2,4]triazol-3-yl]-benzaldehyde and 3-[1-cyclopropylmethyl-5-(4-methoxy-phenyl)-1H-[1,2,4]triazol-3-yl]-benzaldehyde (ca. 1:1) and 5.6N dimethylamine in EtOH the title compound was obtained as an amorphous light yellow foam (78.7% yield), MS: m/e= 363.3 (M+H$^+$).

EXAMPLE 124
[5-(3-Dimethylaminomethyl-phenyl)-3-(4-methoxy-phenyl)-[1,2,4]triazol-1-yl]-acetonitrile hydrochloride and [3-(3-dimethylaminomethyl-phenyl)-5-(4-methoxy-phenyl)-[1,2,4]triazol-1-yl]-acetonitrile hydrochloride (ca. 1:1)

Using [5-(3-formyl-phenyl)-3-(4-methoxy-phenyl)-[1,2,4]triazol-1-yl]-acetonitrile and [3-(3-formyl-phenyl)-5-(4-methoxy-phenyl)-[1,2,4]triazol-1-yl]-acetonitrile (ca. 1:1) and 5.6N dimethylamine in EtOH the title compound was obtained as an amorphous light yellow foam (98.3% yield), MS: m/e=348.3 (M+H$^+$).

EXAMPLE 125
{3-[2-(2-Fluoro-ethyl)-5-(4-methoxy-phenyl)-2H-[1,2,4]triazol-3-yl]-benzyl}-dimethyl-amine hydrochloride and {3-[1-(2-fluoro-ethyl)-5-(4-methoxy-phenyl)-1H-[1,2,4]triazol-3-yl]-benzyl}-dimethyl-amine hydrochloride (ca. 1:1)

Using [3-[2-(2-fluoro-ethyl)-5-(4-methoxy-phenyl)-2H-[1,2,4]triazol-3-yl]-benzaldehyde and 3-[1-(2-fluoro-ethyl)-5-(4-methoxy-phenyl)-1H-[1,2,4]triazol-3-yl]-benzaldehyde(ca. 1:1) and 5.6N dimethylamine in EtOH the title compound was obtained asan amorphous white foam (100% yield), MS: m/e=355.2 (M+H$^+$).

EXAMPLE 126
{3-[5-(4-Methoxy-phenyl)-2-pyridin-4-ylmethyl-2H-[1,2,4]triazol-3-yl]-benzyl}-dimethyl-amine dihydrochloride and {3-[5-(4-methoxy-phenyl)-1-pyridin-4-ylmethyl-1H-[1,2,4]triazol-3-yl]-benzyl}-dimethyl-amine dihydrochloride (ca. 1:2)

Using 3-[5-(4-methoxy-phenyl)-1-pyridin-4-ylmethyl-1H-[1,2,4]triazol-3-yl]-benzaldehyde and 3-[5-(4-methoxy-phenyl)-2-pyridin-4-ylmethyl-2H-[1,2,4]triazol-3-yl]-benzaldehyde(ca. 1:1) and 5.6N dimethylamine in EtOH the title compound was obtained as an amorphous yellow solid (98% yield), MS: m/e=400.3 (M+H$^+$).

EXAMPLE 127

3-[5-(3-Dimethylaminomethyl-phenyl)-3-(4-methoxy-phenyl)-[1,2,4]triazol-1-yl]-propan-1-ol hydrochloride and 3-[3-(3-dimethylaminomethyl-phenyl)-5-(4-methoxy-phenyl)-[1,2,4]triazol-1-yl]-propan-1-ol hydrochloride (ca. 1:1)

Using 3-[1-(3-hydroxy-propyl)-5-(4-methoxy-phenyl)-1H-[1,2,4]triazol-3-yl]-benzaldehyde and 3-[2-(3-hydroxy-propyl)-5-(4-methoxy-phenyl)-2H-[1,2,4]triazol-3benzaldehyde (ca. 1:1) and 5.6N dimethylamine in EtOH the title compound was obtained as an amorphous light yellow foam (88% yield), MS: m/e=367.4 (M+H$^+$).

EXAMPLE 128

[5-(3-Dimethylaminomethyl-phenyl)-3-(4-methoxy-phenyl)-[1,2,4]triazol-1-yl]-acetic acid methyl ester hydrochloride (1:1) and [3-(3-dimethylaminomethyl-phenyl)-5-(4-methoxy-phenyl)-[1,2,4]triazol-1-yl]-acetic acid methyl ester hydrochloride (1:1)

Using [5-(3-formyl-phenyl)-3-(4-methoxy-phenyl)-[1,2,4]triazol-1-yl]-acetic acid methyl ester; compound with [3-(3-formyl-phenyl)-5-(4-methoxy-phenyl)-[1,2,4]triazol-1-yl]-acetic acid methyl ester and 5.6N dimethylamine in EtOH the title compound was obtained as an amorphous light yellow foam (65.3% yield), MS: m/e=381.3 (M+H$^+$).

EXAMPLE 129

{3-[5-(4-Methoxy-phenyl)-2-pyridin-2-ylmethyl-2H-[1,2,4]triazol-3-yl]-benzyl}-dimethyl-amine dihydrochloride and {3-[5-(4-methoxy-phenyl)-1-pyridin-2-ylmethyl-1H-[1,2,4]triazol-3-yl]-benzyl}-dimethyl-amine dihydrochloride (ca. 1:2)

Using 3-[5-(4-methoxy-phenyl)-1-pyridin-2-ylmethyl-1H-[1,2,4]triazol-3-yl]-benzaldehyde; compound with 3-[5-(4-methoxy-phenyl)-2-pyridin-2-ylmethyl-2H-[1,2,4]triazol-3-yl]-benzaldehyde and 5.6N dimethylamine in EtOH the title compound was obtained as an amorphous light yellow foam (100% yield), MS: m/e=400.4 (M+H$^+$).

EXAMPLE 130

{3-[5-(4-Methoxy-phenyl)-2-pyridin-3-ylmethyl-2H-[1,2,4]triazol-3-yl]-benzyl}-dimethyl-amine dihydrochloride and {3-[5-(4-methoxy-phenyl)-1-pyridin-3-ylmethyl-1H-[1,2,4]triazol-3-yl]-benzyl}-dimethyl-amine dihydrochloride (ca. 1:2)

Using 3-[5-(4-methoxy-phenyl)-1-pyridin-3-ylmethyl-1H-[1,2,4]triazol-3-yl]-benzaldehyde; compound with 3-[5-(4-methoxy-phenyl)-2-pyridin-3-ylmethyl-2H-[1,2,4]triazol-3-yl]-benzaldehyde and 5.6N dimethylamine in EtOH the title compound was obtained as an amorphous light yellow foam (100% yield), MS: m/e=400.5 (M+H$^+$).

EXAMPLE 131

{3-[2-(2,2-Difluoro-ethyl)-5-(4-methoxy-phenyl)-2H-[1,2,4]triazol-3-yl]-benzyl}-dimethyl-amine hydrochloride and [3-[1-(2,2-difluoro-ethyl)-5-(4-methoxy-phenyl)-1H-[1,2,4]triazol-3-yl]-benzyl}-dimethyl-amine hydrochloride (ca. 1:1)

Using 3-[1-(2,2-difluoro-ethyl)-5-(4-methoxy-phenyl)-1H-[1,2,4]triazol-3-yl]-benzaldehyde; compound with 3-[2-(2,2-difluoro-ethyl)-5-(4-methoxy-phenphl)-2H-[1,2,4]triazol-3-yl]-benzaldehyde and 5.6N dimethylamine in EtOH the title compound was obtained as an amorphous light yellow foam (95% yield), MS: m/e=373.3 (M+H$^+$).

EXAMPLE 132

{3-[2-Cyclobutylmethyl-5-(4-methoxy-phenyl)-2H-[1,2,4]triazol-3-yl]-benzyl}-dimethyl-amine hydrochloride and [3-[1-cyclobutylmethyl-5-(4-methoxy-phenyl)-1H-[1,2,4]triazol-3-yl]-benzyl}-dimethyl-amine hydrochloride (ca. 1:1)

Using 3-[1-cyclobutylmethyl-5-(4-methoxy-phenyl)-1H-[1,2,4]triazol-3-yl]-benzaldehyde; compound with 3-[2-cyclobutylmethyl-5-(4-methoxy-phenyl)-2H-[1,2,4]triazol-3-yl]-benzaldehyde and 5.6N dimethylamine in EtOH the title compound was obtained as an amorphous light yellow foam (93.9% yield), MS: m/e=377.4 (M+H$^+$).

EXAMPLE 133

3-[5-(3-Dimethylaminomethyl-phenyl)-3-(4-methoxy-phenyl)-[1,2,4]triazol-1-yl]-propionitrile hydrochloride and 3-[3-(3-dimethylaminomethyl-phenyl)-5-(4-methoxy-phenyl)-[1,2,4]triazol-1-yl]-propionitrile hydrochloride (ca. 1:1)

Using 3-[3-(3-formyl-phenyl)-5-(4-methoxy-phenyl)-[1,2,4]triazol-1-yl]-propionitrile; compound with 3-[5-(3-formyl-phenyl)-3-(4-methoxy-phenyl)-[1,2,4]triazol-1-yl]-propionitrile and 5.6N dimethylamine in EtOH the title compound was obtained as an amorphous light yellow foam (100% yield), MS: m/e=362.2 (M+H$^+$).

EXAMPLE 134

{3-[1-Cyclopentyl-5-(4-methoxy-phenyl)-1H-[1,2,4]triazol-3-yl]-benzyl}-dimethyl-amine hydrochloride and {3-[2-cyclopentyl-5-(4-methoxy-phenyl)-2H-[1,2,4]triazol-3-yl]-benzyl}-dimethyl-amine hydrochloride (ca. 1:1)

Using 3-[1-cyclopentyl-5-(4-methoxy-phenyl)-1H-[1,2,4]triazol-3-yl]-benzaldehyde; compound with 3-[2-cyclopentyl-5-(4-methoxy-phenyl)-2H-[1,2,4]triazol-3-yl]-benzaldehyde and 5.6N dimethylamine in EtOH the title compound was obtained as an amorphous light yellow foam (99% yield), MS: m/e=377.4 (M+H$^+$).

EXAMPLE 135

3-[5-(3-Dimethylaminomethyl-phenyl)-3-(4-methoxy-phenyl)-[1,2,4]triazol-1-yl]-propane-1,2-diol hydrochloride and 3-[3-(3-dimethylaminomethyl-phenyl)-5-(4-methoxy-phenyl)-[1,2,4]triazol-1-yl]-propane-1,2-diol hydrochloride (ca. 1:1)

Using 3-[2-(2,3-dihydroxy-propyl)-5-(4-methoxy-phenyl)-2H-[1,2,4]triazol-3-yl]-benzaldehyde; compound with 3-[1-(2,3-dihydroxy-propyl)-5-(4-methoxy-phenyl)-1H-[1,2,4]triazol-3-yl]-benzaldehyde and 5.6N dimethylamine in EtOH the title compound was obtained as an amorphous light yellow solid (84% yield), MS: m/e=383.3 (M+H$^+$).

EXAMPLE 136

{3-[2-Isopropyl-5-(4-methoxy-phenyl)-2H-[1,2,4]triazol-3-yl]-benzyl}-dimethyl-amine hydrochloride and {3-[1-isopropyl-5-(4-methoxy-phenyl)-1H-[1,2,4]triazol-3-yl]-benzyl}-dimethyl-amine hydrochloride (ca. 1:1)

Using 3-[2-iIsopropyl-5-(4-methoxy-phenyl)-2H-[1,2,4]triazol-3-yl]-benzaldehyde; compound with 3-[1-isopropyl-5-(4-methoxy-phenyl)-1H-[1,2,4]triazol-3-yl]-benzaldehyde and 5.6N dimethylamine in EtOH the title compound was obtained as an amorphous light yellow foam (100% yield), MS: m/e=351.4 (M+H⁺).

EXAMPLE 137
{3-[1-(2-Methoxy-ethyl)-5-(4-methoxy-phenyl)-1H-[1,2,4]triazol-3-yl]-benzyl}-dimethyl-amine hydrochloride and {3-[2-(2-methoxy-ethyl)-5-(4-methoxy-phenyl)-2H[-1,2,4]triazol-3-yl]-benzyl}-dimethyl-amine hydrochloride (1:1)

Using 3-[1-(2-methoxy-ethyl)-5-(4-methoxy-phenyl)-1H-[1,2,4]triazol-3-yl]-benzaldehyde; compound with 3-[2-(2-methoxy-ethyl)-5-(4-methoxy-phenyl)-2H-[1,2,4]triazol-3-yl]-benzaldehyde and 5.6N dimethylamine in EtOH the title compound was obtained as an amorphous light brown foam (49% yield), MS: m/e=367.2 (M+H⁺).

EXAMPLE 138
{3-[2-(4-Methoxy-benzyl)-5-(4-methoxy-phenyl)-2H-[1,2,4]triazol-3-yl]-benzyl}-dimethyl-amine hydrochloride and {3-[1-(4-methoxy-benzyl)-5-(4-methoxy-phenyl)-1H-[1,2,4]triazol-3-yl]-benzyl}-dimethyl-amine hydrochloride (ca. 1:1)

Using 3-[1-(4-methoxy-benzyl)-5-(4-methoxy-phenyl)-1H-[1,2,4]triazol-3-yl]-benzaldehyde; compound with 3-[2-(4-methoxy-benzyl)-5-(4-methoxy-phenyl)-2H-[1,2,4]triazol-3-yl]-benzaldehyde and 5.6N dimethylamine in EtOH the title compound was obtained as an amorphous light brown foam (92% yield), MS: m/e=429.5 (M+H⁺).

EXAMPLE 139
4-[5-(3-Dimethylaminomethyl-phenyl)-3-(4-methoxy-phenyl)-[1,2,4]triazol-1-ylmethyl]-phenol hydrochloride and 4-[3-(3-dimethylaminomethyl-phenyl)-5-(4-methoxy-phenyl)-[1,2,4]triazol-1-ylmethyl]-phenol hydrochloride (ca. 1:1)

Using 3-[2-(4-hydroxy-benzyl)-5-(4-methoxy-phenyl)-2H-[1,2,4]triazol-3-yl]-benzaldehyde; compound with 3-[1-(4-hydroxy-benzyl)-5-(4-methoxy-phenyl)-1H-[1,2,4]triazol-3-yl]-benzaldehyde and 5.6N dimethylamine in EtOH the title compound was obtained as an amorphous light yellow foam (63.5% yield), MS: m/e=415.2 (M+H⁺).

EXAMPLE 140
{3-[2-(3-Methoxy-benzyl)-5-(4-methoxy-phenyl)-2H-[1,2,4]triazol-3-yl]-benzyl}-dimethyl-amine hydrochloride and {3-[1-(3-methoxy-benzyl)-5-(4-methoxy-phenyl)-1H-[1,2,4]triazol-3-yl]-benzyl}-dimethyl-amine hydrochloride (ca. 1:1)

Using 3-[1-(3-methoxy-benzyl)-5-(4-methoxy-phenyl)-1H-[1,2,4]triazol-3-yl]-benzaldehyde; compound with 3-[2-(3-methoxy-benzyl)-5-(4-methoxy-phenyl)-2H-[1,2,4]triazol-3-yl]-benzaldehyde and 5.6N dimethylamine in EtOH the title compound was obtained as an amorphous light yellow foam (80.5% yield), MS: m/e=428.2 (M+H⁺).

EXAMPLE 141
{3-[5-(4-Methoxy-phenyl)-2-vinyl-2H-[1,2,4]triazol-3-yl]-benzyl}-dimethyl-amine hydrochloride and {3-[5-(4-methoxy-phenyl)-1-vinyl-1H-[1,2,4]triazol-3-yl]-benzyl}-dimethyl-amine hydrochloride (ca. 1:1)

Using 3-[5-(4-methoxy-phenyl)-1-vinyl-1H-[1,2,4]triazol-3-yl]-benzaldehyde; compound with 3-[5-(4-methoxy-phenyl)-2-vinyl-2H-[1,2,4]triazol-3-yl]-benzaldehyde and 5.6N dimethylamine in EtOH the title compound was obtained as an amorphous white foam (83.5% yield), MS: m/e=334.2 (M+H⁺).

Intermediate Triazoles for Examples 1 to 81

EXAMPLE 142
3-(3-Azidomethyl-phenyl)-5-(4-methoxy-phenyl)-1H-[1,2,4]triazole To an ethanolic suspension of 4-methoxybenzamidine hydrochloride salt (1:1) (2.01 g, 10.8 mmol, 1.5 eq.) was added sodium (331 mg, 14.4 mmol, 2 eq.) in ethanol (60 ml), stirring was then continued for 30 min. at r.t. 3-azidomethyl-benzoic acid hydrazide (1.37 g, 7.2 mmol) in ethanol was then added at 20° C. and the mixture heated at reflux for 18 hrs. Upon cooling the product mixture was filtered, the solvent was evaporated and the residue chromatographed over 20 g SiO₂ (Merck 230–400 mesh) with CH₂Cl₂, affording a solid after evaporation of the solvent. The residue was dried under high vacuum overnight at 20° C. affording the title compound (1.25 g, 57% yield) as a white solid. MS: m/e=306 (M⁺).

EXAMPLE 143
3-[5-(4-Methoxy-phenyl)-1H-[1,2,4]triazol-3-yl]-phenyl-methanol1:1 (mixture of tautomers)

To a solution of 3-[5-(4-methoxy-phenyl)-1H-[1,2,4]triazol-3-yl]-benzaldehyde (120 mg, 0.43 mmol) in THF (10 ml) sodium borohydride (16.3 mg, 0.43 mmol) was added and the mixture stirred for 3 hrs. at r.t. This was followed by addition of water (20 ml) and adjustment of the pH to 1 with 1N HCl, then extraction twice with EtOAc, and drying with Na₂SO₄. Filtration and evaporation of solvent then afforded the title compound (112 mg, 93% yield) as a white solid. MS: m/e=281 (M⁺).

EXAMPLE 144
3-[5-(4-Methoxy-phenyl)-1H-[1,2,4]triazol-3-yl]-benzaldehyde1:1 (mixture of tautomers)

A solution of 3-(3-[1.3-]dioxolan-2-yl-phenyl)-5-(4-methoxy-phenyl)-1H-[1,2,]triazole (7.43 g, 23 mmol) in THF (70 ml) was treated with 4N HCl solution (50 ml) at r.t. for 20 min. The suspension was then filtered and adjusted pH to 8 with 4N NaOH. This was then extracted with EtOAc (250 ml), washed with brine and dried with Na₂SO₄. After solvent evaporation the product was dried overnight under high vacuum to afford the title compound (5.54 g, 86% yield) as a light yellow solid. MS: m/e=279 (M⁺).

EXAMPLE 145
3-(3-[1.3-]Dioxolan-2-yl-phenyl)-5-(4-methoxy-phenyl)-1H-[1,2,]triazole1:1 (mixture of tautomers)

To a stirred ethanolic solution of 4-methoxybenzamidine hydrochloride salt (1:1) (6.8 g, 36.4 mmol, 1.2 eq.), was added sodium (1.04 g, 45.4 mmol) in ethanol (160 ml.) and stirring continued for 30 min. at room temperature 3-[1,3]Dioxolan-2-yl-benzoic acid hydrazide (6.3 g, 30.3 mmol) in ethanol was added and the mixture heated to reflux for 20 hrs. The mixture was cooled, filtered, the solvent was evaporated and the residue chromatographed over 300 g SiO₂ (Merck 230–400 mesh) with CH₂Cl₂—MeOH 99:1. The pure fractions were concentrated and the product obtained was dried under high vacuum to afford the title compound (7.84 g, 80% yield) as a light yellow foam. MS: m/e=323 (M⁺).

Preparation of Hydrazide Intermediates for Examples 1–81

EXAMPLE 146
4-Isopropoxy-benzoic acid hydrazide

A solution of 4-isopropoxy-benzoic acid (2.5 g, 13.8 mmol) in THF (5 ml) was treated with fresh ethereal diazomethane (ca. 20 mg/ml) (0.79 ml, 18.9 mmol, 1.4 eq.) at r.t. and stirred for 15 min. The crude product was then evaporated to dryness, dissolved in ethanol (10 ml) and heated under reflux with hydrazine monohydrate (3.5 ml, 71 mmol, 5 eq.) for 48 hrs. The volatiles were then completely evaporated and the product was dried overnight under high

EXAMPLE 147
2,3-Dihydro-benzofuran-5-carboxylic acid hydrazide

Following the general method of example 146, 2,3-dihydro-benzofuran-5-carboxylic acid was converted to the title compound as a white solid. MS: m/e=178 (M$^+$).

EXAMPLE 148
4-Chloro-3-methoxy-benzoic acid hydrazide

Following the general method of example 146, 4-chloro-3-methoxy-benzoic acid was converted to the title compound as a white solid. MS: m/e=200 (M$^+$).

EXAMPLE 149
Indan-5-carboxylic acid hydrazide

Following the general method of example 146, indan-5-carboxylic acid was converted to the title compound as a beige solid. MS: m/e=176 (M$^+$).

EXAMPLE 150
3-Chloro-4-methoxy-benzoic acid hydrazide

Following the general method of example 146, 3-chloro-4-methoxy-benzoic acid was converted to the title compound as a white solid. MS: m/e=200 (M$^+$).

EXAMPLE 151
4-Methoxy-3-trifluoromethyl-benzoic acid hydrazide

Following the general method of example 146, 4-methoxy-3-trifluoromethyl-benzoic acid was converted to the title compound as a white solid. MS: m/e=234 (M$^+$). Lit: M. Thompson, et al., PCT Int. Appl., WO 9841508 A1 980924. CAN 129:260352

EXAMPLE 152
3-Trifluoromethoxy-benzoic acid hydrazide

Following the general method of example 146, 3-trifluoromethoxy-benzoic acid was converted to the title compound as a white solid. MS: m/e=220 (M$^+$).

EXAMPLE 153
4-Pyrrol-1-yl-benzoic acid hydrazide

Following the general method of example 146, 4-pyrrol-1-yl-benzoic acid was converted to the title compound as a light yellow solid. MS: m/e=201 (M$^+$).

EXAMPLE 154
3-Benzyloxy-4-methoxy-benzoic acid hydrazide

Following the general method of example 146, 3-benzyloxy-4-methoxy-benzoic acid was converted to the title compound as a white solid. MS: m/e=272 (M$^+$).

EXAMPLE 155
4-Benzyloxy-3-methoxy-benzoic acid hydrazide

Following the general method of example 146, 4-benzyloxy-3-methoxy-benzoic acid was converted to the title compound as a white solid. MS: m/e=272 (M$^+$).

EXAMPLE 156
3,5-Difluoro-4-methoxy-benzoic acid hydrazide

Following the general method of example 146, 3,5-difluoro-4-methoxy-benzoic acid was converted to the title compound as a white solid. MS: m/e=202 (M$^+$).

EXAMPLE 157
3,5-Difluoro-benzoic acid hydrazide

Following the general method of example 146, 3,5-difluoro-benzoic acid was converted to the title compound as a white foam. MS: m/e=172 (M$^+$).

EXAMPLE 158
4-Methylsulfanyl-benzoic acid hydrazide

Following the general method of example 146, 4-methylsulfanyl-benzoic acid was converted to the title compound as a white solid. MS: m/e=182 (M$^+$).

EXAMPLE 159
(RS)-1-Methyl-piperidine-3-carboxylic acid hydrazide

Following the general method of example 146, (RS)-1-methyl-piperidine-3-carboxylic acid was converted to the title compound as a light yellow solid. MS: m/e=157 (M$^+$).

EXAMPLE 160
3,5-Bis-trifluoromethyl benzoic acid hydrazide

Following the general method of example 146, 3,5-bis-trifluoromethyl benzoic acid was converted to the title compound as a light yellow solid. MS: m/e=272 (M$^+$).

EXAMPLE 161
3-Chloro-4-trifluoromethyl benzoic acid hydrazide

Following the general method of example 146, 3-chloro-4-trifluoromethyl benzoic acid (*J. Am. Chem. Soc.*, 1956, 78, 1689.) was converted to the title compound as a white solid. MS: m/e=238 (M$^+$).

EXAMPLE 162
(RS)-1,2,3,4-Tetrahydro-naphthalene-2-carboxylic acid hydrazide

Following the general method of example 146, (RS)-1,2,3,4-tetrahydro-naphthalene-2-carboxylic acid was converted to the title compound as a white solid. MS: m/e=190 (M$^+$).

EXAMPLE 163
4-Difluoromethoxy-benzoic acid hydrazide

Following the general method of example 146, 4-difluoromethoxy-benzoic acid was converted to the title compound as a white solid. MS: m/e=202 (M$^+$).

EXAMPLE 164
2,4-Dimethoxy-benzoic acid hydrazide

Following the general method of example 146, 2,4-dimethoxy-benzoic acid was converted to the title compound as a white solid. MS: m/e=196 (M$^+$).

EXAMPLE 165
2,3-Dimethoxy-benzoic acid hydrazide

Following the general method of example 146, 2,3-dimethoxy-benzoic acid was converted to the title compound as a white solid. MS: m/e=196 (M$^+$).

EXAMPLE 166
3-Fluoro-4-methoxy-benzoic acid hydrazide

Following the general method of example 146, 3-fluoro-4-methoxy-benzoic acid was converted to the title compound as a white solid. MS: m/e=184 (M$^+$).

EXAMPLE 167
Thiophene-3-carboxylic acid hydrazide

Following the general method of example 146, thiophene-3-carboxylic acid was converted to the title compound as a white solid. MS: m/e=142 (M$^+$).

EXAMPLE 168
2,3-Dihydro-benzo[1,4]dioxine-6-carboxylic acid hydrazide

Following the general method of example 146, 2,3-dihydro-benzo[1,4]dioxine-6-carboxylic acid was converted to the title compound as a white solid. MS: m/e=194 (M$^+$).

EXAMPLE 169
4-Fluoromethoxy-benzoic acid hydrazide

4-Fluoromethoxy-benzoic acid methyl ester (573 mg, 0.31 mmol) was dissolved in ethanol (10 ml) and heated under reflux with hydrazine monohydrate (0.8 ml, 1.55 mmol, 5 eq.) for 60 hrs. The volatiles were completely evaporated and the product was dried overnight under high vacuum at 40° C., to afford the title compound (577 mg, 100% yield) as a light brown solid. MS: m/e=184 ($M^+$).

EXAMPLE 170
4-Difluoromethoxy-3-fluorobenzoic acid hydrazide

4-Difluoromethoxy-3-fluorobenzoic acid methyl ester was converted to the hydrazide following the conditions described in example 169, affording the title compound as a light brown solid. MS: m/e=220 ($M^+$).

EXAMPLE 171
3-Fluoro-4-fluoromethoxy-benzoic acid hydrazide

3-Fluoro-4-fluoromethoxy-benzoic acid methyl ester was converted to the hydrazide following the conditions described in example 169, affording the title compound as an orange solid. MS: m/e=202 ($M^+$).

EXAMPLE 172
5-Pyrrolidin-1-ylmethyl-thiophene-2-carboxylic acid hydrazide

5-Pyrrolidin-1-ylmethyl-thiophene-2-carboxylic acid methyl ester was converted to the hydrazide following the conditions described in example 169, affording the title compound as a yellow oil. MS: m/e=225 ($M^+$).

EXAMPLE 173
3-[1,3]Dioxolan-2-yl-benzoic acid hydrazide

3-[1,3]Dioxolan-2-yl-benzoic acid methyl ester was converted to the hydrazide following the conditions described in example 169, affording the title compound as a white solid. MS: m/e=208 ($M^+$).

EXAMPLE 174
4-Diethylaminomethyl-benzoic acid hydrazide

4-Diethylaminomethyl-benzoic acid methyl ester was converted to the hydrazide following the conditions described in example 169, affording the title compound as a yellow oil. MS: m/e=221 ($M^+$).

EXAMPLE 175
5-Pyrrolidin-1-ylmethyl-furan-2-carboxylic acid hydrazide

5-Pyrrolidin-1-ylmethyl-furan-2-carboxylic acid methyl ester was converted to the hydrazide following the conditions described in example 169, affording the title compound as a white solid. MS: m/e=209 ($M^+$).

EXAMPLE 176
3-Dimethylaminomethyl-benzoic acid hydrazide

3-Dimethylaminomethyl-benzoic acid methyl ester was converted to the hydrazide following the conditions described in example 169 affording the title compound as a white solid. MS: m/e=193 ($M^+$).

EXAMPLE 177
3-Pyrrolidin-1-ylmethyl-benzoic acid hydrazide

3-Pyrrolidin-1-ylmethyl-benzoic acid methyl ester was converted to the hydrazide following the conditions described in example 169, affording the title compound as a white solid. MS: m/e=219 ($M^+$).

EXAMPLE 178
3-Morpholin-1-ylmethyl-benzoic acid hydrazide

3-Morpholin-1-ylmethyl-benzoic acid methyl ester was converted to the hydrazide following the conditions described in example 169, affording the title compound as a white solid. MS: m/e=235 ($M^+$).

EXAMPLE 179
4,5-Dichloro-2-methoxy-benzoic acid hydrazide 4,5-Dichloro-2-methoxy-benzoic acid ethyl ester was converted to the hydrazide following the conditions described in example 169, affording the title compound as a white solid. MS: m/e=234 ($M^+$).

Lit: Storni, Angelo, et. al., Eur. Pat. Appl., EP 183190 A1 860604. CAN 105:133533

Example 180
3-Azidomethyl-benzoic acid hydrazide

3-Azidomethyl-benzoic acid methyl ester was converted to the hydrazide following the conditions described in example 169 affording the title compound as a white solid. MS: m/e=191 ($M^+$).

EXAMPLE 181
3-Fluoro-4-ethoxy benzoic acid hydrazide

3-Fluoro-4-ethoxy benzoic acid methyl ester was converted to the hydrazide following treatment the conditions described in example 169, affording the title compound as a white solid. MS: m/e=198 ($M^+$).

Precursors of Hydrazides:

EXAMPLE 182

3-[1,3]Dioxolan-2-yl-benzoic acid methyl ester

A solution of 3-formyl-benzoic acid methyl ester (9.48 g, 57.8 mmol), ethylene glycol (8.97 g, 144.5 mmol, 2.5 eq.) and conc. sulfuric acid (0.18 g, 1.8 mmol) in toluene was heated under Dean-Stark reflux for 3 hrs. After cooling, satd. $NaHCO_3$ (100 ml) was added. The aqueous phase was extracted with EtOAc, the combined organic phases were dried over $Na_2SO_4$ and evaporated to afford the title compound (12.1 g, 101% yield) as a yellow liquid. MS: m/e=164 ($M^+$).

EXAMPLE 183
3-Fluoro-4-ethoxy benzoic acid methyl ester

A solution of 3-fluoro-4-hydroxy-benzoic acid methyl ester (1.5 g, 8.82 mmol), $K_2CO_3$ (2.43 g, 17.6 mmol) and ethyliodide (2.75 g, 17.6 mmol) in DMF (15 ml) was heated to 80° C. for 2 hrs. Addition of excess $Na_2CO_3$ and extraction with EtOAc followed by washing with satd. NaCl, then drying with $Na_2SO_4$ and evaporation afforded the title compound (1.76 g, 101% yield) as an orange oil. MS: m/e=170 ($M^+$).

EXAMPLE 184
4-Difluoromethoxy-3-fluoro-benzoic acid methyl ester

A solution of 3-fluoro-4-hydroxy-benzoic acid methyl ester (2 g, 11.75 mmol), chlorodifluoromethane (10.6 g, 122.6 mmol, 10.4 eq.) and $K_2CO_3$ (1.94 g, 14.1 mmol) was heated in an autoclave for 6 hrs. at 160° C. After cooling the mixture was treated with excess $Na_2CO_3$ and extracted with EtOAc. The organic phase was washed twice with satd. NaCl then dried and evaporated to afford the title compound (2.14 g, 83% yield) as an orange oil. MS: m/e=220 ($M^+$).

EXAMPLE 185
3-Fluoro-4-fluoromethoxy-benzoic acid methyl ester

A solution of 4-carboxymethoxy-3-fluoro-benzoic acid methyl ester (2.73 g, 11.9 mmol) in $CH_2Cl_2$ was treated with xenon difluoride (2.23 g 13.1 mmol, 1.1 eq.) at r.t. for 16 hrs. in a teflon reactor vessel. After addition of satd. NaHCO$_3$ solution the organic phase was dried over Na$_2$SO$_4$ and evaporated. The residue was chromatographed over 100 g SiO$_2$ (Merck 230–400 mesh) with EtOAc/nHexane 1:4 affording the title compound (1.24 g, 51% yield) as a white solid. MS: m/e=202 (M$^+$).
Lit: T. B. Patrick, et. al., *Can. J. Chem.* 1986, 64, p138.

EXAMPLE 186
4-Carboxymethoxy-3-fluoro-benzoic acid methyl ester

A solution of 4-tert-butoxycarbonylmethoxy-3-fluoro-benzoic acid methyl ester in CH$_2$Cl$_2$ was treated with trifluoroacetic acid (14.9 ml, 130 mmol, 10.6 eq.) (20 ml) for 3.5 hrs. at r.t. Following evaporation to dryness, the title compound (2.77 g, 99% yield) was obtained as an off-white solid. MS: m/e=228 (M$^+$).

EXAMPLE 187
4-tert-Butoxycarbonylmethoxy-3-fluoro-benzoic acid methyl ester

A mixture of 3-fluoro-4-hydroxy-benzoic acid methyl ester (2.5 g, 14.7 mmol), NaH suspension in oil (55%) (641 mg, 14.7 mmol), KI (244 mg, 14.7 mmol, 0.1 eq.) and tert.butyl bromoacetate (3.44 g, 17.6 mmol 1.2 eq.) in dimethoxyethane (20 ml) was heated to 70° C. for 16 hrs. After evaporation of the solvent the residue was chromatographed over 120 g SiO$_2$ (Merck 230–400 mesh) with EtOAc/nHexane 7:93, affording the title compound (3.53 g, 85% yield) as a colorless liquid. MS: m/e=284 (M$^+$).
Example 188 was Prepared According to the General Procedure Described in Example 185

EXAMPLE 188
4-Fluoromethoxy-benzoic acid methyl ester

The title compound, MS: m/e=184 (M$^+$) was obtained as a yellow solid by reaction of 4-carboxymethoxy-benzoic acid methyl ester with xenon difluoride.
Example 189 was Prepared According to the General Procedure Described in Example 186

EXAMPLE 189
4-Carboxymethoxy-benzoic acid methyl ester

The title compound, MS: m/e=210 (M$^+$) was obtained as an off-white solid by reaction of 4-t.-butoxycarbonylmethoxy-benzoic acid methyl ester with trifluoroacetic acid.
Example 190 was Prepared According to the General Procedure Described in Example 187.

EXAMPLE 190
4-tert-Butoxycarbonylmethoxy-benzoic acid methyl ester

The title compound, MS: m/e=266 (M$^+$) was obtained as a colorless oil by reaction of 4-hydroxy-benzoic acid methyl ester with t.-butyl bromoacetate.

EXAMPLE 191
Methyl-(3-azidomethyl)-benzoate

A mixture of methyl-(3-bromomethyl)-benzoate (12.2 g, 53.2 mmol) and sodium azide (5.2 g, 7.9 mmol, 1.5 eq.) in DMF (40 ml) was stirred at r.t. overnight. Addition of water (150 ml), followed by extraction with ether, drying with Na$_2$SO$_4$ and evaporation afforded the title compound (10.1 g, 99% yield) as a light yellow liquid. MS: m/e=191 (M$^+$).

EXAMPLE 192
3,5-Difluoro-4-methoxy-benzoic acid

At 0° C. a solution of 3,5-difluoro-4-methoxy-propiophenone (1.99 g, 9.96 mmol) in dioxane (8 ml) was added dropwise over 10 min. to a fresh sodium hypobromite solution (prepared at 0° C. from water (25 ml), sodium hydroxide (3.26 g, 81.7 mmol, 8.2 eq.) and bromine (4.77 g, 29.9 mmol, 3 eq). The mixture was stirred and allowed to reach r.t. over 45 min. and then heated at 80° C. for 4 hrs. After cooling, the mixture was extracted twice with ether, then the pH was adjusted to 1–2. The aqueous phase was then extracted twice with EtOAc and these extracts were dried with Na$_2$SO$_4$ and the solvent evaporated to afford the title compound (900 mg, 48% yield) as a light yellow solid. MS: m/e=188 (M$^+$).

EXAMPLE 193
3,5-Difluoro-4-methoxy-propiophenone

A solution of 3,5-difluoro-4-hydroxy-propiophenone (2 g, 10.7 mmol), K$_2$CO$_3$ (2.96 g, 21.5 mmol) in THF/DMF (15 ml, 3 ml) and methyl iodide (6.1 g, 42.9 mmol) was heated to 60° C. for 24 hrs. Following the addition of excess satd. Na$_2$CO$_3$ and extraction of the mixture with EtOAc the organic phase was washed with brine and dried with Na$_2$SO$_4$, the solvent was then evaporated to afford the title compound (2.11 g, 98% yield) as light yellow oil. MS: m/e=200 (M$^+$).

EXAMPLE 194
5-Pyrrolidin-1-ylmethyl-furan-2-carboxylic acid methyl ester

A solution of 5-formyl-furan-2-carboxylic acid (2 g, 14.3 mmol) in THF (5 ml) at r.t. was treated with freshly prepared diazomethane in ether (ca. 20 mg/ml) (0.72 ml, 1.2 eq.). The solvent was evaporated and the crude product (1 g, 6.5 mmol) dissolved in THF (10 ml). AcOH (467 mg, 7.8 mmol, 1.2 eq.) and pyrrolidine (554 mg, 7.8 mmol, 1.2 eq.) were added and the mixture stirred at r.t. for 5 hrs. Sodium triacetoxyborohydride (2.06 g, 9.7 mmol, 1.5 eq.) was then added and stirring continued at r.t. under Ar overnight. Satd. NaHCO$_3$ (50 ml) was then added and the mixture extracted with EtOAc, dried with Na$_2$SO$_4$ and the solvent evaporated. The residue was chromatographed over 90 g SiO$_2$ (Merck 230–400 mesh) with EtOAc/n-hexane 1:1 affording the title compound (426 mg, 31% yield) as an orange oil. MS: m/e=209 (M$^+$).
Example 195 was Prepared According to the General Procedure Described in Example 194

EXAMPLE 195
5-Pyrrolidin-1-ylmethyl-thiophene-2-carboxylic acid methyl ester The title compound, MS: m/e=225 (M$^+$) was obtained as a colorless oil by esterification of 5-formyl-thiophene-2-carboxylic acid with diazomethane in ether and subsequent reaction with pyrrolidine and sodium triacetoxy borohydride.

EXAMPLE 196
Pyrrolidin-1-ylmethyl-benzoic acid methyl ester hydrochloride salt (1:1)

A solution of methyl-3-(bromomethyl)benzoate (7 g, 30.5 mmol) in toluene (170 ml) was heated with pyrrolidine (4.5 g, 64.1 mmol, 2.1 eq.) for at 80° C. for 17 hrs. After addition of Na$_2$CO$_3$, and extraction of the aqueous phase with EtOAc, the organic phase was washed with brine and dried with Na$_2$SO$_4$ Solvent evaporation then afforded the crude product as a yellow oil. This material was dissolved in MeCN and a slight excess of 6N HCl/iPrOH added. After stirring for 30 min. the hydrochloride salt was filtered off and washed with ether to afford the title compound (5 g, 19.5 mmol, 64% yield) as a white solid. MS: m/e=219 (M$^+$).

EXAMPLE 197
3-Dimethylaminomethyl-benzoic acid methyl ester

To a cooled (−10° C.) solution of methyl-3-(bromomethyl)benzoate (22.9 g, 100 mmol) in ether (250 ml) was added dimethylamine hydrochloride salt (17.9 g, 220 mmol) followed by slow addition of triethylamine (30.6 ml, 220 mmol). The mixture was then allowed to warm to r.t. over 48 h, the solids were filtered off and the filter-cake washed with ether. The yellow oil remaining after evaporation of the solvent was distilled over a Vigreux column to afford the title compound (10.7 g, 55% yield) as a colorless oil. MS: m/e=193 ($M^+$).

Amidine and Imidate Preparation

EXAMPLE 198
4-Trifluoromethyl-benzimidic acid ethyl ester hydrochloride salt (1:1)

A solution of 4-trifluoromethyl-benzonitrile (5.16 g, 30.2 mmol) and ethanol (1.39 ml, 30.2 mmol) in chloroform (15 ml) was saturated with a dry stream of HCl gas for 15 min. at −5° C. and the mixture allowed to stand 1 week at 4° C. The product was precipitated with ether, and the suspension stirred for 30 min. at −15°C., then filtered and washed with ether. The solid product was dried at r.t. under high vacuum overnight to afford the title compound (7.1 g, 28 mmol, 93% yield) as a white solid. MS: m/e=217 ($M^+$), 172 ($M^+$-EtOH)

Example 199 was Prepared According to the General Procedure Described in Example 198.

EXAMPLE 199
3,4-Dichloro-benzimidic acid ethyl ester hydrochloride salt (1:1)

The title compound, MS: m/e=217 ($M^+$) was obtained as a white solid by treatment of 3,4-dichloro-benzonitrile with ethanol in chloroform saturated with dry HCl gas.

EXAMPLE 200
2-Fluorobenzamidine hydrochloride salt (1:1)

To a solution of lithium-bis(trimethylsilyl)amide (10 g, 59.8 mmol) in ether (200 ml) in a flame-dried flask, was added 2-fluorobenzonitrile (7.26 g, 59.8 mmol) dropwise over 45 min. at r.t. The mixture was stirred for a further 4 h. at r.t. then cooled to −10° C. and 6N HCl in ethanol (40 ml) added dropwise over 30 min. (exothermic). After allowing the reaction mixture to warm to r.t. overnight the precipitate was filtered and washed with ether then dried under high vacuum at 40° C. overnight. To remove LiCl the dried solid was re-suspended in ethanol (200 ml) and filtered, then the volume reduce volume to ca. 30 ml. The solution was filtered then triturated with ether, and stirred 30 min. at 4° C. Filtration of the precipitate, washing with ether and high vacuum drying overnight at 40° C., afforded the title compound (7.8 g, 44.7 mmol, 75% yield) as a white solid. MS: m/e=138 ($M^+$).

Lit: R. T. Boere, R. T. Oakley and R. W. Reed, *J. Organomet. Chem.*, 1987, 331(2), 161–7.

Example 201 was Prepared According to the General Procedure Described in Example 200

EXAMPLE 201
3-Pyrrolidin-1-ylmethyl-benzamidine hydrochloride salt (1:2)

The title compound, MS: m/e=204.3 ($M+H^+$) was obtained as a white solid by treatment of 3-pyrrolidin-1-ylmethyl-benzonitrile with lithium-bis(trimethylsilyl)amide followed by excess 6N HCl in ethanol.

Example 202 was Prepared According to the General Procedure Described in Example 200

EXAMPLE 202
3-Dimethylaminomethyl-benzamidine hydrochloride salt (1:2)

The title compound, MS: m/e=178.1 ($M+H^+$) was obtained as white hygroscopic foam (contaminated with 30% LiCl) by treatment of 3-dimethylaminomethyl-benzonitrile with lithium-bis(trimethylsilyl)amide followed by excess 6N HCl in ethanol.

Precursors for Benzamidines

EXAMPLE 203
3-Pyrrolidin-1-ylmethyl-benzonitrile

To a stirred solution of of 3-cyanobenzaldehyde (15 g, 114.4 mmol) in THF (150 ml) was added pyrrolidine (9.76 g, 137.2 mmol, 1.2 eq.), acetic acid (8,24 g, 137.2 mmol, 1.2 eq.) and sodium triacetoxyborohydride (36.3 g, 171.6 mmol, 1.5 eq.). The resulting suspension was vigorously stirred at r.t. for 24 hrs. under Ar. 5% $NaHCO_3$ was then added and the mixture stirred for a further 10–15 min. The mixture was then extracted with ethylacetate. The organic phase was washed with brine, then dried with $Na_2SO_4$. After removal of the solvent the yellow liquid was distilled over a Vigreux column to afford the title compound as a colorless liquid (19 g, 102 mmol, 89% yield). MS: m/e=186 ($M^+$)

EXAMPLE 204
3-Dimethylaminomethyl-benzonitrile

A mixture of 3-(bromomethyl)-benzonitrile (3 g, 15.3 mmol) and a solution of 40% dimethylamine in water was heated in a sealed teflon vessel under microwave irradiation (7 min, 600 watts, 150° C., 11 bar). After cooling the resulting mixture was partioned between water and ether, the aqueous phase was extracted three times with ether, washed with satd. NaCl then dried with $Na_2SO_4$ and the solvent evaporated. The resulting yellow oil was distilled in a Kugelrohr apparatus at 60–80° C. and 0.002 mbar affording the title compound (1.53 g, 9.55 mmol, 62% yield) as a pale yellow oil. MS: m/e=160 ($M^+$).

EXAMPLE 205
(RS)3-Fluoro-pyrrolidine hydrochloride (1:1)

To a solution of (RS)-N-benzyl-3-pyrrolidinol (354 mg, 2.0 mmol) in $CH_2Cl_2$ (6 ml) was added diethylaminosulfur tetrafluoride (DAST) (0, 52 ml, 4.0 mmol) over 5 min. at 0–5° C. The mixture was stirred for a further 1.5 hrs. at r.t., then satd. $NaHCO_3$ was added and the oragnic phase was further washed with $NaHCO_3$ (10 ml). After drying the organic phase with $Na_2SO_4$ the residue was chromatographed over $SiO_2$ (Merck 230–400 mesh) with nhexane/EtOAc (4:1) gradient to (1:1). The product was treated with HCl/ether to afford (RS)N-benzy-3-fluoropyrrolidine hydrochloride salt (190 mg, 1.06 mmol, 53% yield) as off-white crystals. This product (250 mg, 1.16 mmol) was then hydrogenated (1 atm. $H_2$) in acetic acid (4 ml) at 100° C. with Pd/C (10%, 25 mg) for 24 hrs. The mixture was then evaporated and dissolved in MeOH, filtered though a celite pad and finally recrystallised from EtOAc/ether to afford the title compound (117 mg, 81% yield) as off-white crystals after drying under high vacuum. MS: m/e=89 ($M^+$)

Lit: G. Giardina et. al., *Synlett*, 1995, 55–7.

EXAMPLE 206
(RS)-3-Methoxy-pyrrolidine hydrobromide (1:1)

To a solution of (RS)-3-hydroxy-pyrrolidine (1 g, 11.5 mmol) in THF (10 ml) and ether (30 ml), was added t.-butylcarbonate (BOC) anhydride (2.7 g, 12.6 mmol) and the mixture stirred overnight at r.t. Evaporation of the solvent afforded the crude product (2.1 g) as an orange oil.

This material (2 g, 10.7 mmol) was dissolved in THF and added to a suspension of sodium hydride (1.8 mmol, 1.2 eq) in THF (20 ml) at −5° C. Then methyl iodide (1.5 g, 10.68 mmol) was added and the mixture stirred for 24 hrs. at r.t. Following aqueous work-up and $SiO_2$ column chromatography (EtOAc/nHexane 1:4) N-tertbutyl-3-methoxy-pyrrolidine (760 mg, 3.8 mmol) was obtained as a yellow oil. A solution of this product (296 mg, 1.4 mmol) was dissolved in acetic acid (10 ml) and treated with HBr/acetic acid (37%, 2 ml) at r.t. for 3 hrs. Following evaporation a brown oil was obtained which was dried under high vacuum to afford the title compound (150 mg, 56% yield). MS: m/e=101 ($M^+$)

Intermediates for Imidazoles

EXAMPLE 207

2-(3,4-Dichloro-phenyl)-4,5-diiodo-1H-imidazole

A mixture of 2-(3,4-dichloro-phenyl)-1H-imidazole (2.13 g, 10.0 mmol) (J. J. Baldwin et al., *J. Heterocycl. Chem.*, 1977, 14, 889), iodine (2.53 g, 10.0 mmol) and silver(I)-sulfate (3.11 g, 10.0 mmol) in ethanol (50 ml) was stirred at r.t. for 17 h. The mixture was filtered, then evaporated, and finally chromatographed over $SiO_2$ with EtOAc-hexane (4:1) and crystallized to obtain 2-(3,4-dichloro-phenyl)-4,5-diiodo-1H-imidazole (1.86 g, 80%) as colorless crystals. Mp. 193° C. (dec.) (EtOAc/pentane), MS: m/e=465 ($M+H^+$).

EXAMPLE 208

2-(3,4-Dichloro-phenyl)-4-iodo-1H-imidazole 1:1 (mixture of tautomers)

A mixture of 2-(3,4-dichloro-phenyl)-4,5-diiodo-lH-imidazole (0.93 g, 2.0 mmol) and sodium sulfite (1.01 g, 8.0 mmol) in ethanol (33 ml) and water (8 ml) was refluxed for 24 h. After addition of EtOAc (200 ml) and brine (20 ml) the organic layer was separated, then dried with $Na_2SO_4$, evaporated and chromatographed over $SiO_2$ with EtOAc-hexane (6:1) to obtain 2-(3,4-dichloro-phenyl)-4-iodo-1H-imidazole (0.57 g, 84%) as a solid mass. Mp. 206–207° C. (EtOAc/hexane), MS: m/e=338 ($M^+$).

EXAMPLE 209

3-[2-(3,4-Dichloro-phenyl)-3H-imidazol-4-yl]-benzonitrile 1:1 (mixture of tautomers)

A solution of 2-(3,4-dichloro-phenyl)-4-iodo-1H-imidazole (1.69 g, 5 mmol) and palladium tetrakis (triphenylphosphine) (0.29 g, 0.25 mmol) in toluene (25 ml) was stirred at r.t. for 15 min. 3-cyanophenylboronic acid (0.74 g, 5 mmol) and 2M $K_2CO_3$ solution (5 ml) was then added and the resulting mixture refluxed for 24 h. EtOAc (200 ml) was added and the organic phase was dried ($Na_2SO_4$), solvent eaporated and the residue chromatographed over $SiO_2$ with EtOAc-hexane=1:1 to give 3-[2-(3,4-dichloro-phenyl)-3H-imidazol-4-yl]-benzonitrile (0.14 g, 9%) as a colorless mass. MS: m/e=313 ($M^+$).

EXAMPLE 210

3-(3H-Imidazol-4-yl)-benzonitrile 1:1 (mixture of tautomers)

An aqueous 40% solution of glyoxal (160 ml) was added dropwise to a solution of 3-cyano-benzaldehyde (17.7 g, 135 mmol) in methanol (320 ml) and aqueous ammonia (160 ml). The mixture was stirred at r.t. for 36 h. A first crop of the title compound was filtered then all volatiles of the filtrate were distilled off and the residue was partitioned between 3N HCl (300 ml) and EtOAc (300 ml). The aqueous phase was neutralized with NaOH (28%) and then extracted with EtOAc. The organic phase was dried ($Na_2SO_4$), concentrated and combined with the first crop to yield 3-(3H-imidazol-4-yl)-benzonitrile (22.0 g, 96%) as a semi-solid mass. MS: m/e=169 ($M^+$).

Following the Method of Example 207 and 208 the Compound of Example 211 was Prepared

EXAMPLE 211

3-(4-Iodo-1H-imidazol-2-yl)-benzonitrile1:1 (mixture of tautomers)

The title compound, Mp. 186–187° C. (EtOAc/hexane), MS: m/e=295 ($M^+$) was obtained as a light red crystalline material by reaction of 3-(3H-imidazol-4-yl)-benzonitrile with iodine and silver sulfate followed by treatment with sodium sulfite.

Following the Method of Example 209 the Compound of Example 212 was Prepared

EXAMPLE 212

3-[4-(4-Methoxy-phenyl)-1H-imidazol-2-yl]-benzonitrile1:1 (mixture of tautomers)

The title compound, MS: m/e=275 ($M^+$) was obtained as a colorless oil by reaction of 3-(4-iodo-1H-imidazol-2-yl)-benzonitrile with 4-methoxybenzene boronic acid in the presence of palladium tetrakis(triphenylphosphine) and 2M $K_2CO_3$ solution.

EXAMPLE 213

3-[5-(3,4-Dichloro-phenyl)-1H-imidazol-2-yl]-benzonitrile1:1 (mixture of tautomers)

A mixture of (3,4-dichloro-phenyl)-oxo-acetaldehyde (9.76 g, 48.1 mmol) (A. J. Saggiomo et al., *J. Med. Chem.*, 1972, 15, 989), 3-cyanobenzaldehyde (6.32 g, 48.1 mmol), ammonium acetate (37.1 g, 481 mmol) and acetic acid (100 ml) was stirred at 110° C. After 3 hrs. the mixture was poured on $H_2O$ (500 ml) and the precipitate chromatographed over $SiO_2$ with EtOAc-hexane (3:1 to2:1) to obtain 3-[5-(3,4-dichloro-phenyl)-1H-imidazol-2-yl]-benzonitrile (2.10 g, 14%) as a yellow oil. MS: m/e=313 ($M^+$).

Following the Method of Example 209 the Compound of Example 214 was Prepared

EXAMPLE 214

3-(4-Phenyl-1H-imidazol-2-yl)-benzonitrile1:1 (mixture of tautomers)

The title compound, MS: m/e=246 ($M+H^+$) was obtained as a light red oil by reaction of 3-(4-iodo-1H-imidazol-2-yl)-benzonitrile with phenylboronic acid in the presence of palladium tetrakis-(triphenylphosphine) and 2M $K_2CO_3$ solution.

Following the Method of Example 209 the Compound of Example 215 was Prepared

EXAMPLE 215

3-(4-Naphthalen-2-yl-1H-imidazol-2-yl)-benzonitrile (mixture of tautomers)

The title compound, Mp. 172–173° C. (EtOAc/hexane), MS: m/e=295 ($M^+$), was obtained as a light red crystalline material by reaction of 3-(4-iodo-1H-imidazol-2-yl)-benzonitrile with 2-naphtylboronic acid in the presence of palladium tetrakis(triphenylphosphine) and 2M $K_2CO_3$ solution.

Aldehyde Intermediates for Examples 118 to 141

EXAMPLE 216

Mixture of 3-[1-Benzyl-5-(4-methoxy-phenyl)-1H-[1,2,4]triazol-3-yl]-benzaldehyde and 3-[2-benzyl-5-(4-methoxy-phenyl)-2H-[1,2,4]triazol-3-yl]-benzaldehyde 1:1

A solution of 3-(3-[1.3-]dioxolan-2-yl-phenyl)-5-(4-methoxy-phenyl)-1H-[1,2,]triazole (210 mg, 0.65 mmol)

and benzyl bromide (400 μl, 3.3 mmol, 5 eq.) in EtOH (0.5 ml) and 1N NaOH (3 ml) were vigorously stirred together at r.t. until all the starting material had been consumed (16 h). The phases were separated and the aqueous phase was extracted with twice with EtOAc, the organic phases were then combined, dried with $Na_2SO_4$ filtered and evaporated. The residue was taken up in THF (5 ml) and treated with 4N HCl (3 ml) at r.t. for 20 min The aqueous phase was then extracted twice with EtOAc, the organic phases were combined, dried, filtered and evaporated. The resulting crude isomeric aldehydes were chromatographed over $SiO_2$ (Merck 230–400 Mesh) eluting with $Et_2O/CH_2Cl_2$ (99:1) to afford the title isomeric aldehydes as a light yellow oil (227 mg, 94% yield), MS: m/e=370.3 (M+H$^+$).

Lit: M. Uda, Y. Hisazumi, K. Sato; *Chem. Pharm. Bull.*, 1976, 24(12), 3103–8.

Following the Method of Example 216 the Compounds of Example 217 to 218 were Prepared

EXAMPLE 217

Mixture of 3-[5-(4-Methoxy-phenyl)-2-phenethyl-2H-[1,2,4]triazol-3-yl]-benzaldehyde and 3-[5-(4-methoxy-phenyl)-1-phenethyl-1H-[1,2,4]triazol-3-yl]-benzaldehyde (ca. 1:1)

Using (2-iodoethyl)benzene the title compound was obtained as yellow oil (22% yield), MS: m/e=383 (M+).

EXAMPLE 218

Mixture of 3-[2-Allyl-5-(4-methoxy-phenyl)-2H-[1,2,4]triazol-3-yl]-benzaldehyde and 3-[1-allyl-5-(4-methoxy-phenyl)-1H-[1,2,4]triazol-3-yl]-benzaldehyde 1:1

Using allyl bromide the title compound was obtained as pale yellow oil (74% yield), MS: m/e=319 (M$^+$).

EXAMPLE 219

3-[5-(4-Methoxy-phenyl)-1-methyl-1H-[1,2,4]triazol-3-yl]-benzaldehyde

A solution of 3-(3-[1.3-]dioxolan-2-yl-phenyl)-5-(4-methoxy-phenyl)-1H-[1,2,]triazole (760 mg, 2.35 mmol) and methyl iodide (750 μl, 12 mmol, 5.1 eq.) in EtOH (1.5 ml) and 1N NaOH (11 ml) were vigorously stirred together at r.t. until all the starting material had been consumed (21 h). The phases were separated and the aqueous phase was extracted with twice with EtOAc, the organic phases were then combined, dried with $Na_2SO_4$ filtered and evaporated. The residue was taken up in THF (5 ml) and treated with 4N HCl (20 ml) at r.t. for 1 h. The aqueous phase was extracted twice with EtOAc, the organic phases were combined, dried, filtered and evaporated. The resulting crude isomeric aldehydes were chromatographed over 70 g of $SiO_2$ (Merck 230–400 Mesh) eluting with $Et_2O/CH_2Cl_2$ (99:1) to afford the title aldehyde as a light yellow solid (190 mg, 28% yield), MS: m/e=293 (M$^+$). The position of methylation on the triazole ring was assigned as $^1$H-NMR, nOe spectroscopy.

Following the Method of Example 219 the Compounds of Example 220 to 225 were Prepared

EXAMPLE 220

3-[5-(4-Methoxy-phenyl)-2-methyl-2H-[1,2,4]triazol-3-yl]-benzaldehyde

A solution of 3-(3-[1.3-]dioxolan-2-yl-phenyl)-5-(4-methoxy-phenyl)-1H-[1,2,]triazole (760 mg, 2.35 mmol) and methyl iodide (750 μl, 12 mmol, 5.1 eq.) in EtOH (1.5 ml) and 1N NaOH (11 ml) were vigorously stirred together at r.t. until all the starting material had been consumed (21 h). The phases were separated and the aqueous phase was extracted with twice with EtOAc, the organic phases were then combined, dried with $Na_2SO_4$ filtered and evaporated. The residue was taken up in THF (5 ml) and treated with 4N HCl (20 ml) at r.t. for 1 h. The aqueous phase was extracted twice with EtOAc, the organic phases were combined, dried, filtered and evaporated. The resulting crude isomeric aldehydes were chromatographed over 70 g of $SiO_2$ (Merck 230–400 Mesh) eluting with $Et_2O/CH_2Cl_2$ (99:1) to afford the title aldehyde as a light yellow solid (118 mg, 17% yield), MS: m/e=283 (M$^+$). The position of methylation on the triazole ring was assigned by $^1$H-NMR, nOe spectroscopy.

EXAMPLE 221

3-[1-Ethyl-5-(4-methoxy-phenyl)-1H-[1,2,4]triazol-3-yl]-benzaldehyde

Using ethyl iodide the title compound was obtained as pale brown oil (32% yield), MS: m/e=307 (M$^+$).

EXAMPLE 222

3-[2-Ethyl-5-(4-methoxy-phenyl)-2H-[1,2,4]triazol-3-yl]-benzaldehyde

Using ethyl iodide the title compound was obtained as pale brown oil (23% yield), MS: m/e=307 (M$^+$).

EXAMPLE 223

3-[5-(4-Difluoromethoxn-phenyl)-2-methyl-2H-[1,2,4]triazol-3-yl]-benzaldehyde

Using 5-(4-difluoromethoxy-phenyl)-3-(3-[1,3]dioxolan-2-yl-phenyl)-1H-[1,2,4]triazole and methyl iodide the title compound was obtained as pale yellow solid (31% yield), MS: m/e=329.1 (M$^+$).

EXAMPLE 224

3-(2-Methyl-5-p-tolyl-2H-[1,2,4]triazol-3-yl)-benzaldehyde

Using 3-(3-[1,3]dioxolan-2-yl-phenyl)-5-p-tolyl-1H-[1,2,4]triazole (mixture of tautomers) and methyl iodide the title compound was obtained as white solid (41% yield), MS: m/e=277.1 (M$^+$).

EXAMPLE 225

3-[5-(3-Fluoro-4-methoxy-phenyl)-2-methyl-2H-[1,2,4]triazol-3-yl]-benzaldehyde

Using 3-(3-[1,3]dioxolan-2-yl-phenyl)-5-(3-fluoro-4-methoxy-phenyl)-1H-[1,2,4]triazole (mixture of tautomers) and methyl iodide the title compound was obtained as an orange solid (34% yield), MS: m/e=311.1 (M$^+$).

EXAMPLE 226

3-[2-Methoxymethyl-5-(4-methoxy-phenyl)-2H-[1,2,4]triazol-3-yl]-benzaldehyde

To a stirred suspension of NaH (55% in oil), (148 mg, 0.34 mmol) at 0° C. in THF (5 ml) was added 3-(3-[1.3-]dioxolan-2-yl-phenyl)-5-(4-methoxy-phenyl)-1H-[1,2,]triazole (1 g, 3 mmol) dropwise in THF (5 ml) over 10 min. The mixture was allowed to stir for a further 30 min then chloromethyl methylether (350 ml, 0.46 mmol) was added and the reaction mixture allowed to warm to r.t. during 1 h. After consumption of the starting material treated 4N HCl (20 ml) was added and the mixture stirred vigorously at r.t. for 3 h. The mixture was then neutralised with $Na_2CO_3$, the organic phase separated and the aqueous phase was extracted twice with EtOAc, the combined organic phases were combined, dried, filtered and evaporated. The resulting crude isomeric aldehydes were chromatographed over 60 g of $SiO_2$ (Merck 230–400 Mesh) eluting with EtOAc/nHexane (1:9) to afford the title aldehyde as a light yellow oil (360 mg, 33% yield), MS: m/e=324.3 (M+H$^+$). The position of alkylation on the triazole ring was assigned as N2 by $^1$H-NMR, nOe spectroscopy.

Following the Method of Example 226 the Compounds of Example 227 to 231 were Prepared

EXAMPLE 227
3-[2-Ethoxymethyl-5-(4-methoxy-phenyl)-2H-[1,2,4]triazol-3-yl]-benzaldehyde Using chloromethyl ethylether title compound was obtained as a pale yellow solid (360 mg, 33% yield), MS: m/e=337.1 (M+).

EXAMPLE 228
3-[1-(2-Hydroxy-ethyl)-5-(4-methoxy-phenyl)-1H-[1,2,4]triazol-3-yl]-benzaldehyde Using bromoethanol title compound was obtained as a white solid (18% yield), MS: m/e=324.3 (M+H+). The position of alkylation on the triazole ring was assigned by $^1$H-NMR, nOe spectroscopy

EXAMPLE 229
3-[2-(2-Hydroxy-ethyl)-5-(4-methoxy-phenyl)-2H-[1,2,4]triazol-3-yl]-benzaldehyde Using bromoethanol title compound was obtained as a white solid (13% yield), MS: m/e=324.3 (M+H+).

EXAMPLE 230
3-[2-Difluoromethyl-5-(4-methoxy-phenyl)-2H-[1,2,4]triazol-3-yl]-benzaldehyde Using chlorodifluoromethane in DMF the title compound was obtained as a pale yellow solid (30% yield), MS: m/e=329.1 (M+).

EXAMPLE 231
3-[5-(4-Methoxy-phenyl)-2-(2-oxo-propyl)-2H-[1,2,4]triazol-3-yl]-benzaldehyde Using chloracetone, the title compound was obtained as a pale yellow solid (3% yield), MS: m/e=335.0 (M+).

EXAMPLE 232
3-[5-(3,4-Dichloro-phenyl)-1-(2-hydroxy-ethyl)-1H-[1,2,4]triazol-3-yl]-benzaldehyde To a solution of 5-(3,4-Dichloro-phenyl)-3-(3-[1,3]dioxolan-2-yl-phenyl)-1H-[1,2,4]triazole mixture of tautomers) (400 mg, 0.31 mmol) in acetonitrile (5 ml) was added 2-bromoethanol (156 μl, 2.21 mmol) and BEMP on poystyrene resin support (2.3 mmol/g, 960 mg). This mixture was shaken at r.t. until the starting material had been consumed (5 d), then aminomethyl polystyrene (1.1 mmol/g, 147 mg) was added and the mixture shaken for a further 2 h at r.t. The mixture was then filtered, washed with acetonitrile and evaporated to afford an isomeric mixture of alkylated acetals which were chromatographically separated over SiO$_2$ (Merck 230–400 Mesh) eluting with EiOAc/nHexane (1:4). The purified isomer was dissolved in THF (3 ml) and treated with 4N HCl (0.3 ml) at r.t. for 3 h, then the mixture was adjusted to pH 9 with NaHCO$_3$, and the aqueous phase extracted twice with EtOAc. The organic phases were combined, dried, filtered and evaporated to afford the title aldehyde as a light yellow solid (45 mg, 11% yield), MS: m/e=362.2 (M+H+). The position of alkylation on the triazole ring was assigned by $^1$H-NMR, nOe spectroscopy.

Abreviations: BEMP=2-tert-butylimino-2-diethylamino-1,3 dimethyl perhydro 1,3,2 diazaphosphorine (comercially available)

EXAMPLE 233
3-[5-(3,4-Dichloro-phenyl)-2-(2-hydroxy-ethyl)-2H-[1,2,4]triazol-3-yl]-benzaldehyde To a solution of 5-(3,4-Dichloro-phenyl)-3-(3-[1,3]dioxolan-2-yl-phenyl)-1H-[1,2,4]triazole (mixture of tautomers) (400 mg, 0.31 mmol) in acetonitrile (5 ml) was added 2-bromoethanol (156 μl, 2.21 mmol) and BEMP on poystyrene resin support (2.3 mmol/g, 960 mg). This mixture was shaken at r.t. until the starting material had been consumed (5 d), then aminomethyl polystyrene (1.1 mmol/g, 147 mg) was added and the mixture shaken for a further 2 h at r.t. The mixture was then filtere, washed with acetonitrile and evaporated to afford an isomeric mixture of alkylated acetals which were chromatographically separated over SiO$_2$ (Merck 230–400 Mesh) eluting with EiOAc/nHexane (1:4). The purified isomer was dissolved in THF (3 ml) and treated with 4N HCl (0.3 ml) at r.t. for 3 h, then the mixture was adjusted to pH 9 with NaHCO$_3$, and the aqueous phase extracted twice with EtOAc. The organic phases were combined, dried, filtered and evaporated to afford the title aldehyde as a off white semi-solid (33 mg, 9% yield), MS: m/e=361 (M+H+). The position of alkylation on the triazole ring was assigned by $^1$H-NMR, nOe spectroscopy.

EXAMPLE 234
Mixture of [3-(3-Formyl-phenyl)-5-(4-methoxy-phenyl)-[1,2,4]triazol-1-yl]-acetic acid ethyl ester and [5-(3-formyl-phenyl)-3-(4-methoxy-phenyl)-[1,2,4]triazol-1-yl]-acetic acid ethyl ester (1:1)

To a solution of 3-(3-[1.3-]dioxolan-2-yl-phenyl)-5-(4-methoxy-phenyl)-1H-[1,2,]triazole (100 mg, 0.31 mmol) in acetonitrile (2 ml) was added ethylbromoacetate (41 μL, 0.37 mmol) and BEMP on poystyrene resin support (2.3 mmol/g, 336 mg). This mixture was shaken at r.t. until the starting material had been consumed (1.5 h), then aminomethyl polystyrene (1.1 mmol/g, 280 mg) was added and the mixture shaken for a further 3 h at r.t. The mixture was then filtered and evaporated to afford an isomeric mixture of alkylated acetals. This material was directly dissolved in THF (5 ml) and treated with 4N HCl (0.3 ml, 4 eq.) at r.t. for 3 h, then the mixture was adjusted to pH 9 with NaHCO$_3$, and the aqueous phase extracted twice with EtOAc. The organic phases were combined, dried, filtered and evaporated to afford the title isomeric aldehydes as a light yellow oil (98 mg, 86% yield), MS: m/e=365.1 (M+H+).

Lit: W. Xu, R. Mohon, M. M. Morrissey; *Bioorg. Med. Chem. Letts.*, 1998, 1089–92. Abreviations: BEMP=2-tert-butylimino-2-diethylamino-1,3 dimethyl perhydro 1,3,2 diazaphosphorine (comercially available)

Following the Method of Example 234 the Compounds of Example 235 to 254 were Prepared

EXAMPLE 235
3-5-(4-Methoxy-phenyl)-2-prop-2-ynyl-2H-[1,2,4]triazol-3-yl]-benzaldehyde and 3-[5-(4-methoxy-phenyl)-1-prop-2-ynyl-1H-[1,2,4]triazol-3-yl]-benzaldehyde (ca. 1:1)

Using propargyl bromide the title compound was obtained as yellow oil (91% yield), MS: m/e=317.1 (M+).

EXAMPLE 236
3-[5-(4-Methoxy-phenyl)-1-(2-methyl-allyl)-1H-[1,2,4]triazol-3-yl]-benzaldehyde and 3-[5-(4-methoxy-phenyl)-2-(2-methyl-allyl)-2H-[1,2,4]triazol-3-yl]-benzaldehyde (ca. 1:1)

Using 3-bromopropyl-2-methylpropene the title compound was obtained as yellow oil (76% yield), MS: m/e=333.1 (M+).

EXAMPLE 237
3-[2-Cyclopropylmethyl-5-(4-methoxy-phenyl)-2H-[1,2,4]triazol-3-yl]-benzaldehyde and 3-[1-cyclopropylmethyl-5-(4-methoxy-phenyl)-1H-[1,2,4]triazol-3-yl]-benzaldehyde (ca. 1:1)

Using (bromomethyl)cyclopropane the title compound was obtained as colorless oil (87% yield), MS: m/e=333.1 (M⁺).

EXAMPLE 238
[5-(3-Formyl-phenyl)-3-(4-methoxy-phenyl)-[1,2,4]triazol-1-yl]-acetonitrile and [3-(3-formyl-phenyl)-5-(4-methoxy-phenyl)-[1,2,4]triazol-1-yl]-acetonitrile (ca. 1:1)

Using bromoacetonitrile the title compound was obtained as light yellow oil (35% yield), MS: m/e=318.0 (M⁺).

EXAMPLE 239
3-[2-(2-Fluoro-ethyl)-5-(4-methoxy-phenyl)-2H-[1,2,4]triazol-3-yl]-benzaldehyde and 3-[1-(2-fluoro-ethyl)-5-(4-methoxy-phenyl)-1H-[1,2,4]triazol-3-yl]-benzaldehyde(ca. 1:1)

Using 1-bromo-2-fluoroethane the title compound was obtained as colorless oil (32% yield), MS: m/e=325.2 (M⁺).

EXAMPLE 240
3-[5-(4-Methoxy-phenyl)-1-pyridin-4-ylmethyl-1H-[1,2,4]triazol-3-yl]-benzaldehyde and 3-[5-(4-methoxy-phenyl)-2-pyridin-4-ylmethyl-2H-[1,2,4]triazol-3-yl]-benzaldehyde (ca. 1:1)

Using 4-(chloromethyl)pyridine the title compound was obtained as brown oil (33% yield), MS: m/e=370.3 (M⁺).

EXAMPLE 241
3-[1-(3-Hydroxy-propyl)-5-(4-methoxy-phenyl)-1H-[1,2,4]triazol-3-yl]-benzaldehyde and 3-[2-(3-hydroxy-propyl)-5-(4-methoxy-phenyl)-2H-[1,2,4]triazol-3-yl]-benzaldehyde (ca. 1:1)

Using 4-(chloromethyl)pyridine the title compound was obtained as colorless oil (40% yield), MS: m/e=337.1 (M⁺).

EXAMPLE 242
[5-(3-Formyl-phenyl)-3-(4-methoxy-phenyl)-[1,2,4]triazol-1-yl]-acetic acid methyl ester and [3-(3-formyl-phenyl)-5-(4-methoxy-phenyl)-[1,2,4]triazol-1-yl]-acetic acid methyl ester 1:1

Using methyl bromoacetate the title compound was obtained as yellow oil (80% yield), MS: m/e=351.1 (M⁺).

EXAMPLE 243
3-[5-(4-Methoxy-phenyl)-1-pyridin-2-ylmethyl-1H-[1,2,4]triazol-3-yl]-benzaldehyde; and 3-[5-(4-methoxy-phenyl)-2-pyridin-2-ylmethyl-2H-[1,2,4]triazol-3-yl]-benzaldehyde Using 2-(chloromethyl)pyridine the title compound was obtained as yellow oil (37% yield), MS: m/e=370.0 (M⁺).

EXAMPLE 244
3-[5-(4-Methoxy-phenyl)-1-pyridin-3-ylmethyl-1H-[1,2,4]triazol-3-yl]-benzaldehyde; and 3-[5-(4-methoxy-phenyl)-2-pyridin-3-ylmethyl-2H-[1,2,4]triazol-3-yl]-benzaldehyde Using 3-(chloromethyl)pyridine the title compound was obtained as yellow oil (66% yield), MS: m/e=370.1 (M⁺).

EXAMPLE 245
3-[1-(2,2-Difluoro-ethyl)-5-(4-methoxy-phenyl)-1H-[1,2,4]triazol-3-yl]-benzaldehyde; and 3-[2-(2,2-difluoro-ethyl)-5-(4-methoxy-phenyl)-2H-[1,2,4]triazol-3-yl]-benzaldehyde Using 2-bromo-1,1-difluoroethane the title compound was obtained as yellow oil (36% yield), MS: m/e=343.1 (M⁺).

EXAMPLE 246
3-[1-Cyclobutylmethyl-5-(4-methoxy-phenyl)-1H-[1,2,4]triazol-3-yl]-benzaldehyde; and 3-[2-cyclobutylmethyl-5-(4-methoxy-phenyl)-2H-[1,2,4]triazol-3-yl]-benzaldehyde Using (bromomethyl)cyclobutane the title compound was obtained as yellow oil (58% yield), MS: m/e=347.1 (M⁺).

EXAMPLE 247
3-[3-(3-Formyl-phenyl)-5-(4-methoxy-phenyl)-[1,2,4]triazol-1-yl]-propionitrile; and 3-[5-(3-formyl-phenyl)-3-(4-methoxy-phenyl)-[1,2,4]triazol-1-yl]-propionitrile Using acrylonitrile the title compound was obtained as yellow oil (73% yield), MS: m/e=332.1 (M⁺).

EXAMPLE 248
3-[1-Cyclopentyl-5-(4-methoxy-phenyl)-1H-[1,2,4]triazol-3-yl]-benzaldehyde; and 3-[2-cyclopentyl-5-(4-methoxy-phenyl)-2H-[1,2,4]triazol-3-yl]-benzaldehyde Using bromocyclopentane the title compound was obtained as yellow oil (52% yield), MS: m/e=347.2 (M⁺).

EXAMPLE 249
3-[2-Isopropyl-5-(4-methoxy-phenyl)-2H-[1,2,4]triazol-3-yl]-benzaldehyde; and 3-[1-isopropyl-5-(4-methoxy-phenyl)-1H-[1,2,4]triazol-3-yl]-benzaldehyde Using 2-bromopropane the title compound was obtained as yellow oil (49% yield), MS: m/e=321.3 (M⁺).

EXAMPLE 250
3-[2-(2,3-Dihydroxy-propyl)-5-(4-methoxy-phenyl)-2H-[1,2,4]triazol-3-yl]-benzaldehyde; and 3-[1-(2,3-dihydroxy-propyl)-5-(4-methoxy-phenyl)-1H-[1,2,4]triazol-3-yl]-benzaldehyde Using 3-chloro-1,2-propanediol the title compound was obtained as yellow oil (18% yield), MS: m/e=353.1 (M⁺).

EXAMPLE 251
3-[1-(2-Methoxy-ethyl)-5-(4-methoxy-phenyl)-1H-[1,2,4]triazol-3-yl]-benzaldehyde; and 3-[2-(2-methoxy-ethyl)-5-(4-methoxy-phenyl)-2H-[1,2,4]triazol-3-yl]-benzaldehyde Using 4-(chloromethyl)pyridine the title compound was obtained as yellow oil (88% yield), MS: m/e=337.1 (M⁺).

EXAMPLE 252
3-[1-(4-Methoxy-benzyl)-5-(4-methoxy-phenyl)-1H-[1,2,4]triazol-3-yl]-benzaldehyd; and 3-[2-(4-methoxy-benzyl)-5-(4-methoxy-phenyl)-2H-[1,2,4]triazol-3-yl]-benzaldehyde Using 4-methoxybenzylchloride the title compound was obtained as yellow oil (97% yield), MS: m/e=400.4 (M⁺).

EXAMPLE 253
3-[2-(4-Hydroxy-benzyl)-5-(4-methoxy-phenyl)-2H-[1,2,4]triazol-3-yl]-benzaldehyde; and 3-[1-(4-hydroxy-benzyl)-5-(4-methoxy-phenyl)-1H-[1,2,4]triazol-3-yl]-benzaldehyde Using 4-(chloromethyl)phenylacetate the title compound was obtained as yellow oil (96% yield), MS: m/e=386.3 (M⁺).

EXAMPLE 254
3-[1-(3-Methoxy-benzyl)-5-(4-methoxy-phenyl)-1H-[1,2,4]triazol-3-yl]-benzaldehyde; and 3-[2-(3-methoxy-benzyl)-5-(4-methoxy-phenyl)-2H-[1,2,4]triazol-3-yl]-benzaldehyde Using 3-methoxybenzylchloride the title compound was obtained as yellow oil (87% yield), MS: m/e=400.4 (M⁺).

EXAMPLE 255
3-[5-(4-Methoxy-phenyl)-1-vinyl-1H-[1,2,4]triazol-3-yl]-benzaldehyde; and 3-[5-(4-methoxy-phenyl)-2-vinyl-2H-[1,2,4]triazol-3-yl]-benzaldehyde To a solution of 3-(3-[1.3-]dioxolan-2-yl-phenyl)-5-(4-methoxy-phenyl)-1H-[1,2]triazole (250 mg, 0.77 mmol) in triethylamine (2.5 ml) was added 1,2-dibromoethane (0.5 ml, 5.8 mmol) and the mixture heated at reflux for 24 h. 4N NaOH (5 ml) was then added and the mixture heated for a further 2 h. The mixture was then extracted with 3 x with $CH_2Cl_2$, washed with saturated NaCl solution and dried with $Na_2SO_4$, filtered and evaporated to afford a isomeric mixture of alkylated acetals. The resulting crude brown oil was then chromatographed over $SiO_2$ (Merck 230–400 mesh) eluting with EtOAc/nHexane (2:3), the product fractions were combined and evaporated to afford a pale yellow oil which was dissolved in THF (5 ml) and treated with 4N HCl (0.2 ml, 4 eq.) at r.t. for 1 h, then the mixture was adjusted to pH 9 with $NaHCO_3$, and the aqueous phase extracted twice with EtOAc. The organic phases were combined, dried, filtered and evaporated to afford the title isomeric aldehydes as a light yellow oil (69 mg, 29% yield), MS: m/e=305.1 $(M+H^+)$.

Lit: *Tetrahedron Letters*, Vol 38, No. 26, pp. 4647–4650, 1997

Intermediates for Examples 223 to 233

EXAMPLE 256

5-(4-Difluoromethoxy-phenyl)-3-(3-[1,3]dioxolan-2-yl-phenyl)-1H-[1,2,4]triazole

To a solution of 4-(difluoromethoxy)benzonitrile (5 g, 30 mmol) in ethanol at 4° C. was bubbled dry HCl(g) for 3 h. The resulting mixture was stoppered and kept at 4° C. for 65 h. Ether (40 ml) was then added with ultrasonication to precipitate the imidate hydrochloride salt, which was washed twice with dry ether (40 ml) and then dried under vacuum (0.05 mmHg) at 20° C. To a solution of imidate hydrochloride salt (1 g, 4 mmol) in ethanol (15 ml) was added sodium ethoxide solution dropwise (sodium: 98 mg, 4 mmol in 5 ml of dry ethanol) at room temperature. The reaction was allowed to stir for a further 30 min then 3-[1,3]Dioxolan-2-yl-benzoic acid hydrazide was added (824 mg, 4 mmol) and the mixture was heated to reflux for 22 h until the starting materials were consumed. The reaction mixture was evaporated to dryness and chromatographed over $SiO_2$ (Merck 230–400 mesh) eluting with EtOAc/nHexane (3:7), the product fractions were combined and evaporated to afford the title compound as a white solid (885 mg, 62% yield), MS: m/e=359.1 $(M^+)$.

Following the Method of Example 256 the Compounds of Example 257 to 259 were Prepared

EXAMPLE 257

5-(3,4-Dichloro-phenyl)-3-(3-[1,3]dioxolan-2-yl-phenyl)-1H-[1,2,4]triazole (mixture of tautomers)

Using 3,4-dichloro-benzonitrile the title compound was obtained as an off-white solid (27% yield), MS: m/e=362.1 $(M^+)$.

EXAMPLE 258

3-(3-[1,3]Dioxolan-2-yl-phenyl)-5-p-tolyl-1H-[1,2,4]triazole (mixture of tautomers)

Using 4-methyl-benzonitrile the title compound was obtained as a white foam (263% yield), MS: m/e=307.1 $(M^+)$.

EXAMPLE 259

3-(3-[1,3]Dioxolan-2-yl-phenyl)-5-(3-fluoro-4-methoxy-phenyl)-1H-[1,2,4]triazole (mixture of tautomers)

Using 3-fluoro-4-methoxy-benzonitrile the title compound was obtained as a light brown foam (39% yield), MS: m/e=341.1 $(M^+)$.

EXAMPLE A

| Tablet Formulation (Wet Granulation) | | | | |
|---|---|---|---|---|
| ingredients | mg/tablet | | | |
| 1. Active compound | 5 | 25 | 100 | 500 |
| 2. Lactose Anhydrous DTG | 125 | 105 | 30 | 150 |
| 3. Sta-Rx 1500 | 6 | 6 | 6 | 30 |
| 4. Microcrystalline Cellulose | 30 | 30 | 30 | 150 |
| 5. Magnesium Stearate | 1 | 1 | 1 | 1 |
| TOTAL | 167 | 167 | 167 | 831 |

Manufacturing Procedure:

1. Mix Items 1, 2, 3 and 4 and granulate with purified water.
2. Dry the granulation at 50° C.
3. Pass the granulation through suitable milling equipment.
4. Add Item 5 and mix for three minutes; compress on a suitable press.

| Capsule Formulation | | | | |
|---|---|---|---|---|
| Ingredients | mg/capsule | | | |
| 1. Active compound | 5 | 25 | 100 | 500 |
| 2. Hydrous Lactose | 159 | 123 | 148 | — |
| 3. Corn Starch | 25 | 35 | 40 | 70 |
| 4. Talc | 10 | 15 | 10 | 25 |
| 5. Magnesium Stearate | 1 | 2 | 2 | 5 |
| TOTAL | 200 | 200 | 300 | 600 |

Manufacturing Procedure:

1. Mix Items 1, 2, and 3 in a suitable mixer for 30 minutes.
2. Add Items 4 and 5 and mix for 3 minutes.
3. Fill into a suitable capsule.

| Tablet Formulation (Wet Granulation) | | | | |
|---|---|---|---|---|
| Ingredients | mg/tablet | | | |
| 1. Active compound | 5 | 25 | 100 | 500 |
| 2. Lactose Anhydrous | 125 | 105 | 30 | 150 |
| 3. Sta-Rx 1500 | 6 | 6 | 6 | 30 |
| 4. Microcrystalline Cellulose | 30 | 30 | 30 | 150 |
| 5. Magnesium Stearate | 1 | 2 | 2 | 5 |
| TOTAL | 167 | 168 | 168 | 835 |

Manufacturing Procedure:

1. Mix Items 1, 2, 3 and 4 and granulate with purified water.
2. Dry the granulation at 50° C.
3. Pass the granulation through suitable milling equipment.
4. Add Item 5 and mix for three minutes; compress on a suitable press.

What is claimed is:

1. A compound of the formula

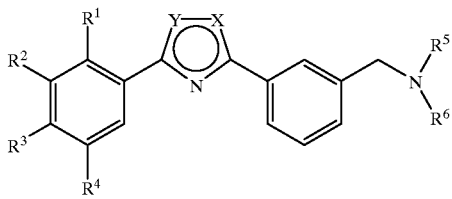

I wherein
  $R^1$–$R^4$ signify independently hydrogen, —$CF_3$, —$OCF_3$, $OCHF_2$, —$OCH_2F$, lower alkyl, lower alkoxy, halogen, hydroxy, phenyl, benzyl, amino, nitro, pyrrol-1-yl, lower alkyl-sulfonyl, lower alkyl-sulfanyl, cyano or benzyloxy; or
  $R^2$ and $R^3$ when taken together form —O—$(CH_2)_2$—O—, —O—$CH_2$—O—, —O—$(CH_2)_2$—, —$(CH_2)_3$— or —CH=CH—CH=CH—;
  X signifies —N=, or —N($R^7$)—;
  Y signifies —N=, or =N—, —N($R^7$)—;
  $R^5$ and $R^6$ signify independently from each other hydrogen, lower alkyl, —C(O)-lower alkyl, hydroxy-lower alkyl, lower alkenyl, —C(O)$CH_2$OH or
  $R^5$ and $R^6$ when taken together with the N-atom form a substituted or unsubstituted ring structure —$(CH_2)_n$—, —$(CH_2)_2$—O—$(CH_2)_2$—, —$CH_2$—CH[OC(O)$CH_3$]—$(CH_2)_2$—, —$CH_2$—CH[NHC(O)$CH_3$]—$(CH_2)_2$, —O—$(CH_2)_3$—, —$CH_2$—CH($OCH_3$)—$(CH_2)_2$—, —$CH_2$—CH(halogen)—$(CH_2)_2$—, —$(CH_2)_2$—CH(O-phenyl)—$(CH_2)_2$—, —$(CH_2)_2$—N(CHO)—$(CH_2)_2$—, —$(CH_2)_2$—N($COCH_3$)—$(CH_2)_2$—, —$CH_2$—CH(OH)—$(CH_2)_3$—, —$(CH_2)_2$—CH(OH)—$(CH_2)_2$—, —$(CH_2)_2$—N(benzyl)—$(CH_2)_2$— or —$CH_2$—CH=CH—$CH_2$—;
  n signifies 3 to 5; and
  $R^7$ signifies hydrogen, lower alkyl, lower alkenyl, lower alkinyl, —$(CH_2)_m$—O-lower alkyl, —$(CH_2)_m$—OH, —$(CH_2)_m$—$CHF_2$, —$(CH_2)_m$—$CH_2F$, —$(CH_2)_m$—C(O)-lower alkyl, —$(CH_2)_m$—C(O)O-lower alkyl, —$(CH_2)_m$—CH(OH)-lower alkyl, —$(CH_2)_m$—CH(OH)—$(CH_2)_m$OH, —$(CH_2)_m$—$C_6H_5$, which phenyl ring is optionally substituted by lower alkyl, lower alkoxy or hydroxy, —$(CH_2)_m$—C(=$CH_2$)-lower alkyl, —$(CH_2)_m$-cycloalkyl, —$(CH_2)_m$—CN, —$(CH_2)_m$-pyridin-4-yl, —$(CH_2)_m$-pyridin-3-yl or —$(CH_2)_m$-pyridin-2-yl;
  m signifies 0 to 4;
  or its pharmaceutically acceptable acid addition salts and tautomers.

2. A compound of claim 1 wherein $R^1$ is hydrogen, lower alkoxy, halogen, or hydroxy; $R^2$ is hydrogen, lower alkoxy, halogen, —$CF_3$, —$OCF_3$ or —$OCHF_2$, or may be taken together with $R^3$ to form —O—$(CH_2)_2$—O—, —O—$CH_2$—O—, —O—$(CH_2)_2$—, —$(CH_2)_3$— or —CH=CH—CH=CH—; $R^4$ is hydrogen, halogen, lower alkoxy, or $CF_3$, and $R^3$, $R^5$, $R^6$ and $R^7$ are as in claim 1.

3. A compound of claim 2 wherein $R^1$ is hydrogen, methoxy, ethoxy, chloro, or fluoro; $R^2$ is hydrogen, chloro, or fluoro, $R^3$ is —$OCHF_2$, —$OCH_2F$, —$OCH_3$, —$OCH_2CH_3$, chloro or methyl; $R^4$ is hydrogen or fluoro, and $R^5$ and $R^6$ are hydrogen or lower alkyl or are together —$(CH_2)_4$—, —$CH_2CH(OH)(CH_2)_2$— or —$CH_2CH[NHC(O)CH_3](CH_2)_2$—.

4. A compound of claim 3, wherein X is —N=, Y is —NH—, $R^1$ is hydrogen, $R^2$ is hydrogen or fluoro, $R^3$ is —$OCHF_2$, —$OCH_2F$, or —$OCH_3$, $R^4$ is hydrogen or fluoro and $R^5$ and $R^6$ are methyl.

5. A compound of 4, which is
  {3-[5-(4-difluoromethoxy-phenyl)-1H-[1,2,4]triazol-3-yl]-benzyl}-dimethyl-amine
  {3-[5-(4-fluoromethoxy-phenyl)-1H-[1,2,4]triazol-3-yl]-benzyl}-dimethyl-amine
  {3-[5-(3-fluoro-4-methoxy-phenyl)-1H-[1,2,4]triazol-3-yl]-benzyl}-dimethyl-amine
  {3-[5-(4-difluoromethoxy-3-fluoro-phenyl)-1H-[1,2,4]triazol-3-yl]-benzyl}-dimrthyl-amine
  {3-[5-(3,5-difluoro-4-methoxy-phenyl)-1H-[1,2,4]triazol-3-yl]-benzyl}-dimethyl-amine or
  {3-[5-(3-fluoro-4-fluoromethoxy-phenyl)-1H-[1,2,4]triazol-3-yl]-benzyl}-dimethyl-amine; and tautomers thereof.

6. A compound of claim 3, wherein X is —N=, Y is —NH—, $R^1$ is hydrogen, $R^2$ is hydrogen or chloro, $R^3$ is —$OCHF_2$, —$OCH_3$ or —$OCH_2CH_3$, $R^4$ is hydrogen or fluoro and $R^5$ and $R^6$ are hydrogen or methyl or are together —$(CH_2)_4$—, —$CH_2CH(OH)(CH_2)_2$— or —$CH_2CH[NHC(O)CH_3](CH_2)_2$—.

7. A compound of claim 6 which is
  5-(4-difluoromethoxy-phenyl)-3-(3-pyrrolidin-1-ylmethyl-phenyl)-1H-[1,2,4]triazole
  5-(3-fluoro-4-methoxy-phenyl)-3-(3-pyrrolidin-1-ylmethyl-phenyl)-1H-[1,2,4]triazole
  5-(4-ethoxy-phenyl)-3-(3-pyrrolidin-1-ylmethyl-phenyl)-1H-[1,2,4]triazole
  5-(3-chloro-4-methoxy-phenyl)-3-(3-pyrrolidin-1-ylmethyl-phenyl)-1H-[1,2,4]triazole
  3-[5-(4-methoxy-phenyl)-1H-[1,2,4]triazol-3-yl]-benzylamine
  (RS)-1-{3-[5-(4-methoxy-phenyl)-1H-[1,2,4]triazol-3-yl]-benzyl}-pyrrolidin-3-ol
  (S)—N—(1-{3-[5-(4-methoxy-phenyl)-1H-[1,2,4]triazol-3-yl]-benzyl}-pyrrolidin-3-yl)-acetamide or
  {3-[5-(4-methoxy-phenyl)-1H-[1,2,4]triazol-3-yl]-benzyl}-methyl-amine; and tautomers thereof.

8. A compound of claim 3, wherein X is —N($R^7$)— or —N= and Y is —N($R^7$)— or —N= and $R^7$ is lower alkyl, —$CH_2$—O-lower alkyl or —$(CH_2)_2$OH, $R^1$, $R^2$ and $R^4$ are hydrogen, $R^3$ is methyloxy, and $R^5$ and $R^6$ are methyl.

9. A compound of claim 8, which is
  {3-[5-(4-methoxy-phenyl)-2-methyl-2H-[1,2,4]triazol-3-yl]-benzyl}-dimethyl-amine,
  3-(4-methoxy-phenyl)-1-methyl-5-(3-pyrrolidin-1-ylmethyl-phenyl)-1H-[1,2,4]triazol,
  5-[3-(2,5-dihydro-pyrrol-1-ylmethyl)-phenyl]-3-(4-methoxy-phenyl)-1-methyl-1H-[1,2,4]triazole,
  1-ethyl-3-(4-methoxy-phenyl)-5-(3-pyrrolidin-1-ylmethyl-phenyl)-1H-[1,2,4]triazole,
  {3-[2-ethoxymethyl-5-(4-methoxy-phenyl)-2H-[1,2,4]triazol-3-yl]-benzyl}-dimethyl-amine,
  {3-[2-methoxymethyl-5-(4-methoxy-phenyl)-2H-[1,2,4]triazol-3-yl]-benzyl}-dimethyl-amine,
  2-[5-(3-dimethylaminomethyl-phenyl)-3-(4-methoxy-phenyl)-[1,2,4]triazol-1-yl]-ethanol,
  {3-[5-(4-difluoromethoxy-phenyl)-2-methyl-2H-[1,2,4]triazol-3-yl]-benzyl}-dimethyl-amine, dimethyl-[3-(2-methyl-5-p-tolyl-2H-[1,2,4]triazol-3-yl)-benzyl]-amine and {3-[5-(3-Fluoro-4-methoxy-phenyl)-2-methyl-2H-[1,2,4]triazol-3-yl]-benzyl}-dimethyl-amine.

10. A process for preparing a compound of formula I where Y is —N= or =N— and X is —N=, which process comprises:

reacting a compound of formula

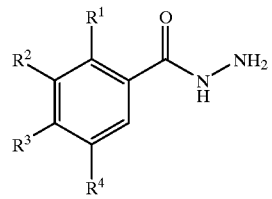

II with a compound of the formula

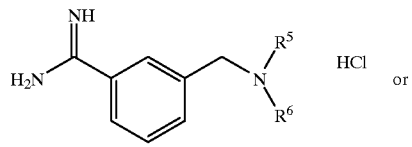

III or

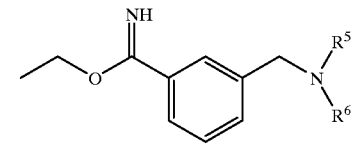

IV to obtain a compound of formula

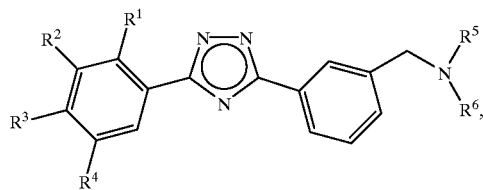

I-1 and isolating single regioisomers from a mixture of isomers to obtain a compound of formula I.

11. A process for preparing a compound of formula I where Y is —N= or =N— and X is —CH=, which process comprises:

reacting a compound of formula

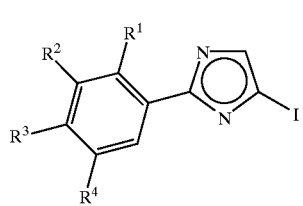

V with a compound of formula

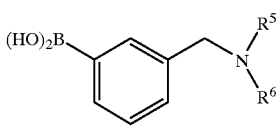

VI in the presence of Pd(PPh$_3$)$_4$ to obtain a compound of formula

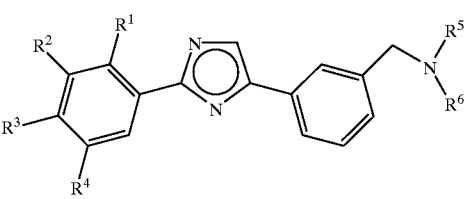

I-2 and isolating single regioisomers from a mixture of isomers to obtain a compound of formula I.

12. A process for preparing a compound of formula I where Y is —CH= and X is —N=, and R$^5$ and R$^6$ are hydrogen, lower alkyl, or hydroxy lower alkyl which process comprises:

a) reducing a compound of formula

VII to a compound of formula

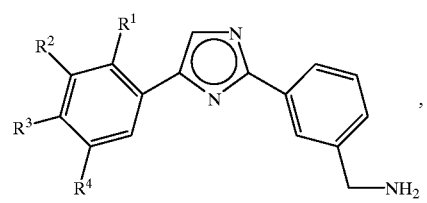

I-3 b) reacting a compound of formula I-3 with R$^{5'}$COCl and LiAlH$_4$ to give a compound of formula

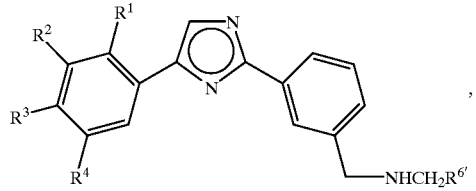

I-4

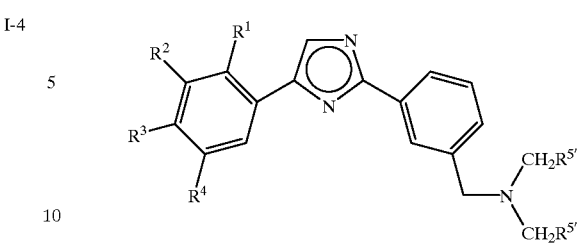

I-5 c) reacting a compound of formula I-4 with $R^{6'}$COCl and LiAlH$_4$ to give a compound of formula and isolating single regiosomers from a mixture of isomers, where $R^{5'}$ and $R^{6'}$ are hydrogen, lower alkyl, or hydroxy lower alkyl.

13. A pharmaceutical composition comprising a compound of claim 1 and a pharmaceutically acceptable carrier.

14. A method for the treatment or reduction of neurodegeneration caused by overactivation of NMDA receptor subtypes by administering an amount of a compound of formula I effective to alleviate the neurodegeneration.

* * * * *

UNITED STATES PATENT AND TRADEMARK OFFICE
CERTIFICATE OF CORRECTION

PATENT NO. : 6,265,426 B1
DATED : July 24, 2001
INVENTOR(S) : Alexander Alanine et al.

It is certified that error appears in the above-identified patent and that said Letters Patent is hereby corrected as shown below:

Column 112, claim 12,
Lines 1-12, replace the present formula with

--

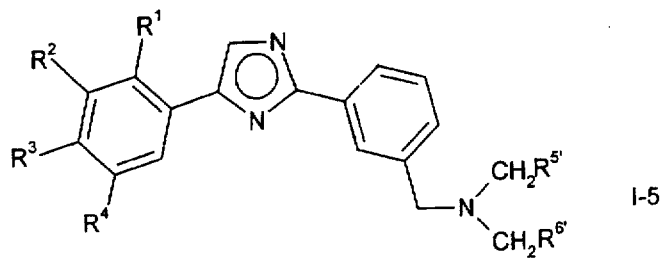

I-5

--

Column 111, claim 12,
Lines 1-12, replace the present formula with

-

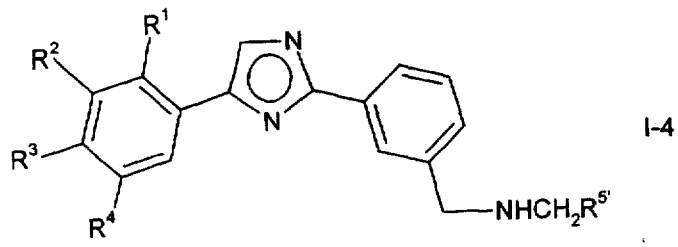

I-4

--

UNITED STATES PATENT AND TRADEMARK OFFICE
CERTIFICATE OF CORRECTION

PATENT NO. : 6,265,426 B1
DATED : July 24, 2001
INVENTOR(S) : Alexander Alanine et al.

Page 2 of 2

It is certified that error appears in the above-identified patent and that said Letters Patent is hereby corrected as shown below:

<u>Columns 15 and 16,</u>
Replace Scheme 6 with:

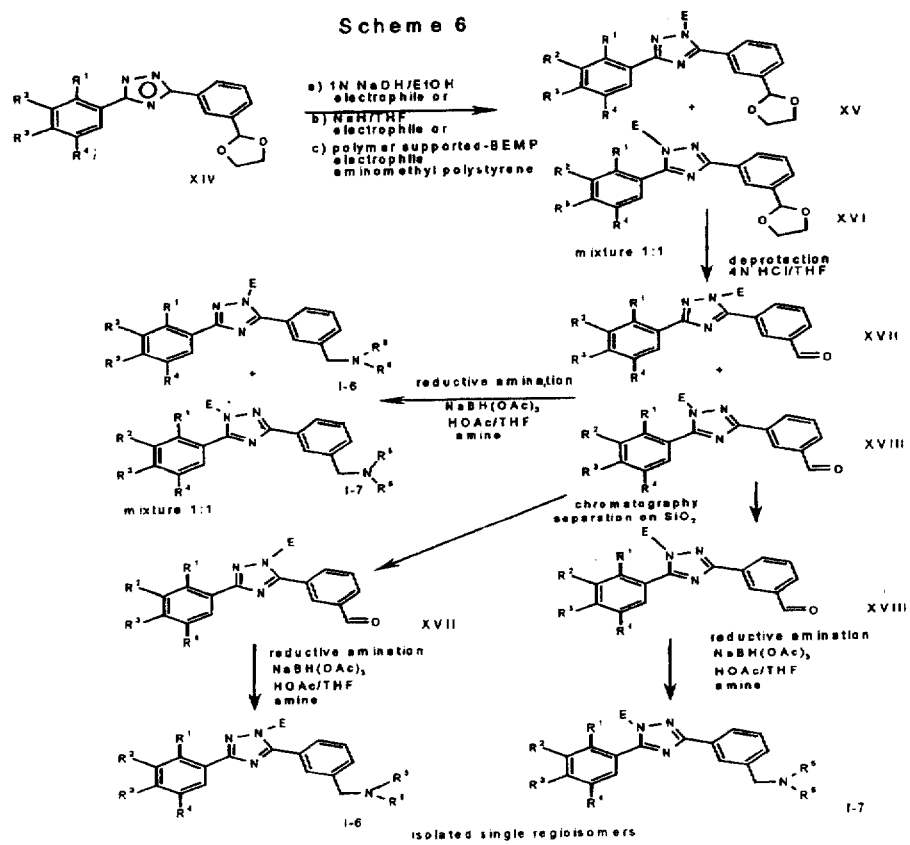

Signed and Sealed this

Sixteenth Day of April, 2002

Attest:

JAMES E. ROGAN
Attesting Officer
Director of the United States Patent and Trademark Office